US007713942B2

(12) United States Patent
Dalsgaard et al.

(10) Patent No.: US 7,713,942 B2
(45) Date of Patent: May 11, 2010

(54) CAGE-LIKE MICROPARTICLE COMPLEXES COMPRISING STEROLS AND SAPONINS FOR DELIVERY OF POLYNUCLEOTIDES

(75) Inventors: Kristian Dalsgaard, Kalvehave (DK); Nikolai Søren Kirkby, Copenhagen (DK)

(73) Assignee: Nordic Vaccine Technology A/S, Bagsvaerd (DK)

(*) Notice: Subject to any disclaimer, the term of this patent is extended or adjusted under 35 U.S.C. 154(b) by 630 days.

(21) Appl. No.: 10/114,957

(22) Filed: Apr. 4, 2002

(65) Prior Publication Data

US 2003/0118635 A1 Jun. 26, 2003

Related U.S. Application Data

(60) Provisional application No. 60/308,609, filed on Jul. 31, 2001.

(30) Foreign Application Priority Data

Apr. 4, 2001 (DK) .............................. 2001 00560

(51) Int. Cl.
*A01N 43/04* (2006.01)
*A61K 31/70* (2006.01)
*A61K 9/14* (2006.01)
*A61K 45/00* (2006.01)
*A61K 47/44* (2006.01)

(52) U.S. Cl. .................... 514/44 R; 424/484; 424/283.1

(58) Field of Classification Search .................... 514/44, 514/2; 424/450; 435/320.1, 455, 458
See application file for complete search history.

(56) References Cited

U.S. PATENT DOCUMENTS

| 4,578,269 | A | | 3/1986 | Morein |
| 4,900,549 | A | | 2/1990 | De Vries et al. |
| 5,254,339 | A | | 10/1993 | Morein |
| 5,567,434 | A | * | 10/1996 | Szoka, Jr. .................... 424/450 |
| 5,679,354 | A | | 10/1997 | Morein et al. |
| 5,981,505 | A | * | 11/1999 | Weiner et al. ................. 514/44 |
| 6,027,732 | A | * | 2/2000 | Morein et al. ............. 424/241.1 |
| 6,080,725 | A | | 6/2000 | Marciani |
| 6,352,697 | B1 | | 3/2002 | Cox et al. |
| 6,395,302 | B1 | * | 5/2002 | Hennink et al. ............. 424/489 |
| 6,500,432 | B1 | * | 12/2002 | Dalemans et al. ........ 424/184.1 |
| 6,506,386 | B1 | | 1/2003 | Friede et al. |
| 6,544,518 | B1 | | 4/2003 | Friede et al. |
| 6,607,732 | B2 | | 8/2003 | Morein et al. |
| 6,780,421 | B1 | | 8/2004 | Haensler et al. |
| 6,846,489 | B1 | * | 1/2005 | Garcon et al. ............. 424/278.1 |
| 7,105,164 | B1 | * | 9/2006 | Sia et al. .................... 424/188.1 |
| 2001/0053365 | A1 | * | 12/2001 | Friede et al. ............. 424/187.1 |
| 2002/0098200 | A1 | * | 7/2002 | Campos-Neto et al. .. 424/190.1 |

FOREIGN PATENT DOCUMENTS

| DE | 19740092 A1 | 3/1999 |
| EP | 0109942 A2 * | 10/1983 |
| EP | 0884056 A1 * | 12/1998 |
| JP | 10067688 | 3/1998 |
| WO | WO 92/06710 A1 | 4/1992 |
| WO | WO 92/21331 | 12/1992 |
| WO | WO 92/21331 A1 | 12/1992 |
| WO | 95/27508 | 10/1995 |
| WO | WO 97/28817 | 8/1997 |
| WO | WO 98/36772 A1 | 8/1998 |
| WO | WO 98/56420 A1 | 12/1998 |
| WO | WO 99/18995 | 4/1999 |
| WO | WO-9930733 A * | 6/1999 |
| WO | WO 00/48630 | 8/2000 |
| WO | WO 00/51565 | 9/2000 |
| WO | 0062800 | 10/2000 |

OTHER PUBLICATIONS

Eglimez, et al. (1996) Biochem. Biophys. Res. Comm., 221: 169-73.*
Jacobsen, et al. (1996) Carbohydrate Research, 280(1): 1-14.*
Teng, et al. (2002) Journal of Virology, 76(12): 6164-71.*
(Abstract) Bjorkman et al., "Application of iscom antigen preparations in ELISAs for diagnosis of Neospora and toxoplasma infestions", International Journal for Parasitology, Jan. 1998, vol. 28, pp. 187-193.
Chanas, et al., "Sucrose density gradient formation by freezing and thawing", *Med. Lab. Sci.*, vol. 37, pp. 89-90, 1980.
Classen, et al., "Antigen detection in vivo after immunization with different presentation forms of rabies virus antigen: involvement of marginal metallophillic macrophages in the uptake of immune-stimulating complexes", *Eur. J. Immunol.*, vol. 25, pp. 1446-1452, 1995.
Dalsgaard, "Saponin adjuvants. III Isolation of a substance from Quillaja saponaria Molina with adjuvant activity in food-and-mouth disease vaccines", *Arch. Gesamte Virusforsch*, vol. 44, pp. 243, 254, 1974.

(Continued)

*Primary Examiner*—Robert M Kelly
(74) *Attorney, Agent, or Firm*—Sterne, Kessler, Goldstein & Fox, P.L.L.C.

(57) ABSTRACT

The present invention pertains to complexes comprising sterols and saponins. The complexes are capable of binding a genetic determinant including a polynucleotide. The complexes may further comprise a lipophilic moiety, optionally a lipophilic moiety comprising a contacting group and/or a targeting ligand, and/or a saccharide moiety. The complexes may further comprise an immunogenic determinant and/or an antigenic determinant and/or a medicament and/or a diagnostic compound. The complexes may in even further embodiments be encapsulated by an encapsulation agent including a biodegradable microsphere. The present invention also pertains to pharmaceutical compositions and methods of treatment of an individual by therapy and/or surgery, methods of cosmetic treatment, and diagnostic methods practised on the human or animal body.

32 Claims, 12 Drawing Sheets

OTHER PUBLICATIONS

Heeg, et al., "Vaccination of class I major histocompatibility complex (MHC)-restricted murine CD8+ cytotoxic T lymphocytes towards soluble antigens: immunostimulating-ovalbumin complexes enter the class I MHC-restricted antigen pathway and allow sensitization against the immunodominant peptide", *Eur. J. Immunol.*, vol. 21, pp. 1523-1527, 1991.

Lovgren, et al., "The requirement of lipids for the formation of immunostimulating complexes (iscoms)", *Biotechnol. Appl. Biochem.* vol. 10, pp. 167-172, 1988.

Lovgren, et al., "Conjugation of synthetic peptides to carrier iscoms: factors affecting the immunogenicity of the conjugate", *J. Immunol. Methods*, vol. 173, pp. 237-243, 1994.

Morein, et al., "Increased immunogenicity of a non-amphiphatic protein (BSA) after inclusion into iscoms", *J. Immunol. Methods*, vol. 128, pp. 177-181, 1990.

Villacres, et al., "Internalization of iscom-borne antigens and presentation under MHC class I or class II restriction", *Cell Immunol.*, vol. 185, pp. 30-38, 1998.

Watson, et al., "Inflammatory response and antigen localization following immunization with influenza virus ISCOMs", *Inflammation*, vol. 13, pp. 641-649, 1989.

Björkman and Lundén. Application of iscom antigen preparations in ELISAs for diagnosis of neospora and toxoplasma infections. International Journal for Parasitology, vol. 28, 1998, pp. 187-193.

Sasaki et al. Induction of systemic and mucosal immune responses to human immunodeficiency virus type 1 by a DNA vaccine formulated with QS-21 saponin adjuvant via intramuscular and intranasal routes. Journal of Virology, Jun. 1998. vol. 72, No. 6, pp. 4931-4939.

* cited by examiner

Triterpene class

Steroid class        Steroid alkaloid class

A
(Oleanane)

B
(Ursane)

C
(Lupane)

D
(Hopane)

E
(Dammarane)

F
(Lanostane)

G
(Cycloartane)
(9,19-Cyclolanostane)

H

I

X

-OOC(CH₂)₃N⁺(CH₃)₃      ChoTB

-OOC(CH₂)₂COO(CH₂)₂N⁺(CH₃)₃      ChoSC

-OCONH(CH₂)₂N(CH₃)₂      DC-Chol

-OCONH(CH₂)₂N⁺(CH₃)₃ Cl⁻      TC-Chol

Lipid 67

BGTC

BGSC

DOTIM

DODAC

GAP-DLRIE

SEQUENCE LISTING

```
<160> NUMBER OF SEQ ID NOS: 3

<210> SEQ ID NO 1
<211> LENGTH: 5
<212> TYPE: PRT
<213> ORGANISM: Unknown
<220> FEATURE:
<223> OTHER INFORMATION: Core sequence of AF12198, a IL-1 binding
      peptide
<220> FEATURE:
<221> NAME/KEY: misc_feature
<222> LOCATION: (4)..(4)
<223> OTHER INFORMATION: Xaa = Azetidine

<400> SEQUENCE: 1

Trp Tyr Gln Xaa Tyr
1               5

<210> SEQ ID NO 2
<211> LENGTH: 12
<212> TYPE: PRT
<213> ORGANISM: Unknown
<220> FEATURE:
<223> OTHER INFORMATION: Il-1 antagonist peptide sequence
<220> FEATURE:
<221> NAME/KEY: misc_feature
<222> LOCATION: (7)..(7)
<223> OTHER INFORMATION: Xaa = Azetidine

<400> SEQUENCE: 2

Trp Pro Gly Trp Tyr Gln Xaa Tyr Ala Leu Pro Leu
1               5                   10

<210> SEQ ID NO 3
<211> LENGTH: 14
<212> TYPE: PRT
<213> ORGANISM: Unknown
<220> FEATURE:
<223> OTHER INFORMATION: Il-1 antagonist peptide sequence
<220> FEATURE:
<221> NAME/KEY: misc_feature
<222> LOCATION: (9)..(9)
<223> OTHER INFORMATION: Xaa = Azetidine

<400> SEQUENCE: 3

Phe Glu Trp Pro Gly Trp Tyr Gln Xaa Tyr Ala Leu Pro Leu
1               5                   10
```

CAGE-LIKE MICROPARTICLE COMPLEXES COMPRISING STEROLS AND SAPONINS FOR DELIVERY OF POLYNUCLEOTIDES

This application is a nonprovisional of U.S. provisional application Ser. No. 60/308,609 filed on Jul. 31, 2001, which is hereby incorporated by reference in its entirety. All patent and nonpatent references cited in the application, or in the present application, are also hereby incorporated by reference in their entirety.

FIELD OF THE INVENTION

The present invention relates to complexes of sterols and saponin glycosides. The complexes are capable of interacting with bioactive agents including genetic determinants, such as e.g. polynucleotides. The complexes pertaining to the present invention can be used to facilitate the transport of polynucleotides, including DNA and derivatives thereof, across cellular membranes.

Acting as carriers of various bioactive agents and genetic determinants, the complexes provide a means for introducing e.g. a polynucleotide into a patient, a predetermined region of the patient, or a predetermined biological cell of the patient, in order e.g. to express a gene comprised by the polynucleotide and/or to regulate the expression of genes being expressed in the biological cell in vivo and/or in vitro.

More particularly, the present invention relates to novel methods for transfecting a biological cell, to complexes involved in such methods, and to diagnostic methods and therapeutic methods for treating a patient by e.g. gene therapy and DNA-vaccination.

BACKGROUND OF THE INVENTION

Several medical applications utilizing genetic determinants have evolved in recent years. In such applications, the introduction of whole genes or specific nucleic acids into cells is of central importance. This process is often referred to as gene transfection independently of the origin of the cells, the sequence and character of the nucleic acid, and irrespective of whether the transfer is performed in vivo or ex vivo.

To facilitate the process of gene transfection several different approaches have been developed. Such approaches include among others i) using biological vectors (including viral vectors), ii) associating a nucleic acid with a cationic liposome, iii) associating a nucleic acid with peptides covalently linked to a transfection agent, and iv) coating minute gold particles by nucleic acids and using the coated particles for a bio-ballistic transfer.

The major iscom constituents are quillaja saponins and cholesterol. The procedure for preparation of iscoms comprises solubilization of amphipathic polypeptides in preferably nonionic detergents, addition of Quillaja saponins, cholesterol, and possibly also phosphatidylcholine. In the presence of amphipathic proteins, iscom particles are formed on removal of the detergent.

Morein (see e.g. U.S. Pat. No. 4,578,269) was the first to describe that iscoms not only formed a very characteristic structural complex, but also possessed significant immunogenic properties when amphipathic antigens were inserted into this complex by hydrophobic interaction. Conventional iscoms (immunostimulating complexes) have since been used for vaccine formulations and combine a multimeric presentation of an antigen with an adjuvant functionality. (see e.g. U.S. Pat. No. 6,080,725 to Marciani).

SUMMARY OF THE INVENTION

The present invention is one aspect relates to a complex comprising at least one sterol and/or at least one saponin, wherein the at least one sterol or the at least one saponin is capable of forming an electrostatic interaction or hydrophobic interaction with at least one bioactive agent, including a genetic determinant, including a polynucleotide, including DNA and derivatives thereof. When the at least one sterol and the at least one saponin is incapable of forming an electrostatic interaction or a hydrophobic interaction with the at least one bioactive agent as described herein above, the complex comprises at least one contacting group capable of contacting the at least one bioactive agent, including a genetic determinant, including a polynucleotide, including DNA and derivatives thereof, by means of an interaction selected from an electrostatic interaction and a hydrophobic interaction and an interaction resulting from intercalation of the genetic determinant by the contacting group.

According, in one aspect of the invention there is provided a complex comprising i) at least one first sterol and/or at least one second sterol, wherein the at least one second sterol is capable of contacting a genetic determinant by means of an interaction selected from an electrostatic interaction and a hydrophobic interaction, and
wherein the at least one first sterol and/or the at least one second sterol is capable of forming a complex with at least one first saponin and/or at least one second saponin, and ii) at least one first saponin and/or at least one second saponin,
wherein the at least one second saponin is capable of contacting a genetic determinant by means of an interaction selected from an electrostatic interaction and a hydrophobic interaction, and
wherein the at least one first saponin and/or the at least one second saponin is capable of forming a complex with at least one first sterol and/or at least one second sterol, and optionally iii) at least one contacting group for contacting a genetic determinant by means of an interaction selected from an electrostatic interaction and a hydrophobic interaction,
with the proviso that the at least one contacting group is present when no second sterol and no second saponin is present in the complex.

The complexes according to the invention are useful for binding polynucleotides including naturally occurring nucleic acids including DNA and RNA, and derivatives thereof, including, but not limited to peptide nucleic acids (PNA) and locked nucleic acids (LNA). The bound polynucleotide can subsequently be transferred into a biological cell including any animal cell or human cell.

The complexes according to the present invention may in one preferred embodiment adopt a micro-particle structure in the form of a cage-like matrix similar to that known as an immune stimulating complex (iscom). Beside iscom structures, the interaction between sterols and saponins have been reported to result in a variety of different structural entities, including entities such as e.g. lattices, honeycombes, rods, and amorphic particles, all of which structural entities are covered by the present invention. However, other structures and matrix formations are also envisaged by the present invention which is in no way limited to iscom-like structures or matrixes.

In the case where the complexes according to the present invention do form iscoms, or iscom-like structures, such iscoms or structures may be prepared e.g. essentially as described in European patent EP 0 109 942 B1.

Accordingly, a glycoside solution, containing fx cholesterol, phospholipid, and one or more glycosides (fx Quillaja components) with hydrophobic and hydrophilic domains in a concentration of at least a critical micelle-binding concentration, is formed and a complex is generated. The complex may subsequently be isolated and/or purified.

Optionally, as a first step, the component to be inserted into the complex, fx a bioactive agent, including a polynucleotide, such as DNA and derivatives thereof, an immunogenic agent, an antigenic agent, a therapeutic agent, a diagnostic agent, and the like, can be mixed with one or more solubilizing agents, whereby complexes are formed between the component and solubilizing agents, after which the components are separated from the solubilizing agent and e.g. transferred directly to the glycoside solution.

In line with the present invention, the glycoside solution may initially be mixed with a polynucleotide. It is possible to proceed from a matrix that can be made by solubilizing at least one sterol in a solution agent, adding at least one glycoside or at least one saponin, and optionally the other lipophilic moieties, after which addition the solution agent may be removed, if it is proving unacceptable to the final product.

The matrix may be transferred to a water solution in which its separate parts are not soluble. The solubilizing agent can be removed through eg gel filtration, ultra filtration, dialysis, or electrophores. The matrix can then be purified from surplus of first sterol and saponin e.g. by ultracentrifugation, through a density gradient, or through gel filtration. The solubilizing agent may be any one of those mentioned in U.S. Pat. No. 5,679,354, which is incorporated herein by reference.

In one preferred embodiment, the complexes according to the invention are formed essentially as described in Example 1 herein.

Accordingly, in one preferred embodiment, there is provided a method for preparation of a complex comprising i) at least one first sterol and/or at least one second sterol,
wherein the at least one second sterol is capable of contacting a genetic determinant by means of an interaction selected from an electrostatic interaction and a hydrophobic interaction, and
wherein the at least one first sterol and/or the at least one second sterol is capable of forming a complex with at least one first saponin and/or at least one second saponin, and ii) at least one first saponin and/or at least one second saponin,
wherein the at least one second saponin is capable of contacting a genetic determinant by means of an interaction selected from an electrostatic interaction and a hydrophobic interaction, and
wherein the at least one first saponin and/or the at least one second saponin is capable of forming a complex with at least one first sterol and/or at least one second sterol, and optionally iii) at least one contacting group for contacting a genetic determinant by means of an interaction selected from an electrostatic interaction and a hydrophobic interaction, with the proviso that the at least one contacting group is present when no second sterol and no second saponin is present in the complex, and further optionally iv) at least one lipophilic moiety,
wherein said method comprises the steps of a) mixing a sterol composition comprising at least one first sterol and/or at least one second sterol, with b) a saponin composition comprising at least one first saponin and/or at least one second saponin, and c) at least one lipophilic moiety, and d) at least one organic solvent,
wherein the steps a) to d) may be carried out simultaneously, or sequentially, in any order, and optionally e) removing surplus reactants and/or purifying the prepared complexes.

The organic solvent is preferably selected from ethanol, DMSO, and DMF, and the solvent is preferably present in an amount of at the most 25% (vol/vol), such as at the most 20% (vol/vol), for example at the most 15% (vol/vol), such as at the most 10% (vol/vol), for example at the most 8% (vol/vol), such as at the most 6% (vol/vol), for example at the most 4% (vol/vol), such as at the most 2% (vol/vol), for example at the most 1% (vol/vol), such as at the most 0.5% (vol/vol), for example at the most 0.1% (vol/vol).

First and Second Sterols and Saponins

The following general distinction is made between first and second sterols. First and/or second sterols can be naturally occurring sterols synthesised as secondary metabolites by many organisms. They may also be synthetic, or they may be made by chemical synthesis or enzymatic synthesis either in vitro or in vivo. First sterols are generally incapable of forming an association with a genetic determinant as defined herein, whereas such an association is formed between second sterols and the genetic determinant.

Similarly, first and/or second saponins can be any saponin as defined herein comprising as an aglycone part either i) a triterpene part, ii) a steroid part, or iii) a steroid alkaloid part. The saponins may be naturally occurring or synthetic, or they may be made by chemical synthesis or enzymatic synthesis either in vitro or in vivo. First saponins are generally incapable of forming an association with a genetic determinant as defined herein, whereas such an association is formed between second saponins and the genetic determinant.

Consequently, any sterol will either be a first sterol, or a second sterol, and any saponin will either be a first saponin, or a second saponin. In principle, first and/or second sterols, as well as first and/or second saponins, may be either anionic, neutral, or cationic. The terms cationic sterols and cationic saponins shall denote sterols and saponins, respectively, carrying a net positive charge at pH 7.0. Second sterols and second saponins are preferably cationic sterols and cationic saponins, respectively, whereas first sterols and first saponins are preferably anionic or neutral sterols and saponins, respectively.

Accordingly, the second sterols and/or second saponins preferably comprise at least one positively charged moiety or reactive group at pH=7.0, and this positively charged moiety or reactive group is according to one preferred embodiment of the invention capable of contacting a bioactive agent, including a genetic determinant, by means of an electrostatic interaction.

In another embodiment, the second sterols and/or second saponins preferably comprise an uncharged moiety or non-polar reactive group, and this uncharged moiety or non-polar reactive group is according to another preferred embodiment of the invention capable of contacting a bioactive group, including a genetic determinant, by means of a hydrophobic interaction.

A combination of electrostatic interactions and hydrophobic interactions can also be used for generating an association between bioactive agents and second sterols and/or saponins.

When the complexes according to the present invention comprise no second sterol and no second saponin, the complexes comprise at least one contacting group capable of contacting a genetic determinant by means either of an electrostatic interaction, or a hydrophobic interaction.

The contacting group is necessary in order for such complexes to form the desired association with the genetic determinant. However, the contacting group may also be present in complexes comprising a second sterol and/or a second saponin. The term "contacting group" as used herein will also refer to any moiety of a second sterol and/or a second saponin capable of forming an association with a genetic determinant, including an association generated by an electrostatic interaction and/or a hydrophobic interaction.

Preferred contacting groups comprise at least one lipophilic moiety capable of forming an association with the complex according to the invention made up by sterols (first and/or second) and/or saponins (first and/or second).

In addition to acting as a "docking group" or "anchor" for contacting groups according to the invention, lipophilic moieties may also serve to facilitate a saponin-sterol complex formation essentially without serving, during or after complex formation, as a "docking group" for a contacting group or any other functional group forming part of the saponin-sterol complex. The purpose of using lipophilic moieties may thus be two-fold: The lipophilic moieties according to the invention may act—during or after saponin-sterol complex formation, preferably during saponin-sterol complex formation—as a facilitator of complex formation, and they may, independently of this action, also act as a "docking group" for any functional group including contacting groups for contacting a genetic determinant and/or targeting ligands for targeting the complexes according to the invention.

Lipophilic moieties such as phospholipids are preferably present during the process of forming the complexes according to the invention. The presence of e.g. phospholipids facilitates complex formation over a broad concentration range. Accordingly, phosphatidyl choline may be added when mixing saponins and sterols during complex formation.

It is preferred to use a phospholipid with a positively charged headgroup such as phosphatidyl ethanolamine. One reason for this is the inclusion into the complex of an overall positive charge capable of facilitating or resulting in an interaction with negatively charged polynucleotides including ribonucleic acids. This interaction will facilitate the uptake of the polynucleotides across a cellular membrane and into a biological cell for subsequent integration and/or translation and/or polypeptide expression. Phosphatidyl choline is an example of another phospholipid capable of being used in connection with the present invention.

Additional moieties of a contacting group may be either lipophilic or hydrophilic, depending on the nature of the association formed with the genetic determinant. One preferred additional moiety of the contacting group is a ionic group, or a charged group, preferably a positively charged group, including a group comprising a positve charge at pH=7.0. Examples of such groups are illustrated for lipophilic moieties in FIGS. 6, 7 and 8. Such lipophilic moieties can be obtained from, among others, Avanti Polar Lipids, Inc. Alabaster, Ala.

It is thus possible to imagine a series of different compositions of the complexes according to the invention. The invention in preferred embodiments relates to i) complexes comprises at least one first sterol and at least one first saponin and at least one contacting group,
ii) complexes comprising at least one first sterol and at least one second saponin,
iii) complexes comprising at least one first sterol and at least one second saponin and at least one contacting group,
iv) complexes comprising at least one first sterol and at least one first saponin and at least one second saponin,
v) complexes comprising at least one first sterol and at least one first saponin and at least one second saponin and at least one contacting group,
vi) complexes comprising at least one second sterol and at least one first saponin,
vii) complexes comprising at least one second sterol and at least one first saponin and at least one contacting group,
viii) complexes comprising at least one second sterol and at least one second saponin,
ix) complexes comprising at least one second sterol and at least one second saponin and at least one contacting group,
x) complexes comprising at least one second sterol and at least one first saponin and at least one second saponin,
xi) complexes comprising at least one second sterol and at least one first saponin and at least one second saponin and at least one contacting group,
xii) complexes comprising at least one first sterol and at least one second sterol and at least one first saponin,
xiii) complexes comprising at least one first sterol and at least one second sterol and at least one first saponin and at least one contacting group,
xiv) complexes comprising at least one first sterol and at least one second sterol and at least one second saponin,
xv) complexes comprising at least one first sterol and at least one second sterol and at least one second saponin and at least one contacting group,
xvi) complexes comprising at least one first sterol and at least one second sterol and at least one first saponin and at least one second saponin,
xvii) complexes comprising at least one first sterol and at least one second sterol and at least one first saponin and at least one second saponin and at least one contacting group, including any composition comprising any combination of the complexes listed herein immediately above, i.e. any combination of complexes i) to xvii) Such combinations may be of value when attempting to direct or target different complexes to different regions of a patient.

The mechanism by which the contacting group interacts with nucleic acid depends upon the character of the contacting group in question. One example of a contacting group is a cationic (positively charged) derivative of a cholesterol which is capable of forming an interaction with a genetic determinant by e.g. forming an electrostatic interaction with the backbone of a polynucleotide including any DNA-backbone. Another example is a lipid-tailed acridin-compound that intercalates with double stranded DNA.

In addition to sterols (first and/or second), saponins (first and/or second), and contacting groups comprising a lipophilic moiety, the complexes according to the present invention may further comprise a targeting ligand for targeting a particular polynucletide, including a nucleic acid, to a specific cell surface or tissue. This may be accomplished by incorporation of specific targeting ligands and/or receptor binding molecules and/or ligands into the structure of the complexes according to the invention.

Accordingly, two different methods for the formation of the complexes according to the invention are provided, in one method the contacting group are incorporated during the formation of the particles, and in another method the contacting group is added to preformed particles, optionally in the form of iscom-matrices.

One principal aspect of the invention is thus the provision of a novel system that enhances the uptake of polynucleotides including nucleic acids by combining—in one preferred embodiment—i) the ability of iscom-structures to associate with, and penetrate into or through membranes containing cholesterol, with ii) the property of contacting or associating with polynucleotides including nucleic acids. In particular for the application of vaccination with naked DNA the complexes according to the invention is likely to reduce the required amount of DNA.

It should be noted that the invention is not limited to complexes capable of forming an association with polynucleotides. The complexes according to the invention in other preferred embodiments are capable of contacting or forming an association with polypeptides and/or polynucleotides.

Accordingly, the present invention in one embodiment pertains to complexes comprising components also forming a part of traditional iscoms. However, the complexes according to the present invention are different from conventional iscoms in a number of ways. Firstly, the complexes according to the present invention are capable of binding a bioactive agent including a genetic determinant in the form of e.g. a polynucleotide. Secondly, the complexes in one preferred embodiment are characterised by a zeta-potential which is less negative—or more positive—than about −50 mV.

Accordingly, there is provided a complex having a zeta-potential which is less negative or more positive than about −50 mV, such as a zeta-potential of about −45 mV, for example a zeta-potential of about −40 mV, such as a zeta-potential of about −37 mV, for example a zeta-potential of about −35 mV, such as a zeta-potential of about −32 mV, for example a zeta-potential of about −30 mV such as a zeta-potential of about −29 mV, for example a zeta-potential of about −28 mV, such as a zeta-potential of about −27 mV, for example a zeta-potential of about −26 mV, such as a zeta-potential of about −25 mV, for example a zeta-potential of about −20 mV, such as a zeta-potential of about −15 mV, for example a zeta-potential of about −10 mV, such as a zeta-potential of about −5 mV, for example a zeta-potential of about 0 mV, such as a zeta-potential of about 5 mV, for example a zeta-potential of about 10 mV, such as a zeta-potential of about 15 mV, for example a zeta-potential of about 20 mV, and preferably a zeta-potential of less than 50 mV.

The complexes in preferred embodiments may thus have a zeta-potential of from about −50 mV to about −40 mV, such as from about −40 mV to about −35 mV, for example of from about −35 mV to about −0 mV, such as from about −30 mV to about −25 mV, for example of from about −25 mV to about −20 mV, such as from about −20 mV to about −15 mV, for example of from about −15 mV to about −10 mV, such as from about −10 mV to about −5 mV, for example of from about −5 mV to about 0 mV, such as from about 0 mV to about 5 mV, for example of from about 5 mV to about 10 mV, such as from about 10 mV to about 15 mV, for example of from about 15 mV to about 20 mV, such as from about 20 mV to about 30 mV, for example of from about 30 mV to about 40 mV, such as from about 40 mV to about 50 mV.

Using as a standard reference point a complex comprising i) any given saponin(s) of interest and ii) cholesterol as a first sterol, complexes according to the invention comprising i) any given saponin(s) of interest, ii) cholesterol as a first sterol, and iii) any given second sterol of interest, preferably a cholesterol derivative as listed in FIG. 5 herein, said complexes according to the invention have a zeta-potential which is at least about 5 mV less negative or more positive than said reference complexes:, such as a zeta-potential which is at least about 10 mV less negative or more positive than said reference complexes, for example a zeta-potential which is at least about 15 mV less negative or more positive than said reference complexes, such as a zeta-potential which is at least about 20 mV less negative or more positive than said reference complexes, for example a zeta-potential which is at least about 25 mV less negative or more positive than said reference complexes, such as a zeta-potential which is at least about 30 mV less negative or more positive than said reference complexes, for example a zeta-potential which is at least about 35 mV less negative or more positive than said reference complexes, such as a zeta-potential which is at least about 40 mV less negative or more positive than said reference complexes, for example a zeta-potential which is at least about 45 mV less negative or more positive than said reference complexes, such as a zeta-potential which is at least about 50 mV less negative or more positive than said reference complexes.

The values of the zeta-potentials for the complexes of the present invention are determined in part by the inclusion of e.g. cationic second saponins and/or cationic second sterols into the complexes according to the present invention.

The molar ratio between saponins (first and second) and sterols (first and second) in complexes according to the present invention is preferably from less than 1000:1 to preferably more than 1:1000. Preferred ratios are about 100:1, for example about 80:1, such as about 60:1, for example about 50:1, such as about 40:1, for example about 30:1, such as about 25:1, for example about 20:1, such as about 18:1, for example about 16:1, such as about 14:1, for example about 12:1, such as about 10:1, for example about 9:1, such as about 8:1, for example about 7:1, such as about 6:1, for example about 5:1, such as about 4:1, for example about 3:1, such as about 2:1, for example about 1.9:1, such as about 1.8:1, for example about 1.7:1, such as about 1.6:1, for example about 1.5:1, such as about 1.4:1, for example about 1.3:1, such as about 1.2:1, for example about 1.1:1, such as about 1:1, for example about 1:1.1, such as about 1:1.2, for example about 1:1.3, such as about 1:1.4, for example about 1:1.5, such as about 1:1.6, for example about 1:1.7, such as about 1:1.8, for example about 1;1.9, such as about 1:2.0, for example about 1:2.5, such as about 1:3, for example about 1:3.5, for example about 1:4, such. as about 1:4.5, for example about 1:5, for example about 1:5.5, such as about 1:6, for example about 1:7, such as about 1:10, for example about 1:20, such as about 1:40, for example about 1:60, such as about 1:80, for example about 1:100.

Without being bound by theory, the complexes according to the present invention may according to one presently preferred hypothesis adopt either an iscom-like structure, or a structure that does not resemble such a structure when contacting or being associated with either a polynucleotide and/or a polypeptide comprising e.g. natural or synthetic amino acids and variants thereof. When being connected by the complexes, the polynucleotides and/or polypeptides are according to one preferred hypothesis in a degradation-resistent conformation, or in a conformation less prone to degradation, as compared to the conformation of the polynucleotide or the polypeptide when it is not associated with the complex according to the invention The invention thus in one preferred embodiment relates to complexes comprising a polynucleotide and/or a polypeptide that is less likely to be degraded by nucleases and proteases, respectively, under practical circumstances.

Accordingly, there is provided in one preferred embodiment a method for administration of a polynucleotide and/or a polypeptide to an individual in need thereof, said polynucleotide and/or said polypeptide being administered in association with the complexes according to the invention in a conformation that is not susceptible to degradation under practical circumstances—or less susceptible to degradation under practical circumstances—as compared to the degradation taking place when the polynucleotide and/or the polypeptide is administered in the absence of the complexes under substantially similar conditions, including conditions wherein the polynucleotide and/or the polypeptide is administered in combination with conventional carriers or adjuvants.

Consequently, the present invention in one particular embodiment relates to complexes in the form of modified iscoms that are used as carriers for bioactive agents including polynucleotides and other genetic determinants which are desirably transfected into a biological cell by means of an interaction of the complex with the cellular membrane.

Complexes according to the invention may thus comprise one or more selected from the group consisting of bioactive agents, immunogenic determinants, genetic determinants, enzymes, adjuvants and medicaments. Hence, by way of example a complex according to the present invention may comprise both a genetic determinant and an antigenic determinant, such as a nucleic acid and a polypeptide.

The complexes according to the invention may further comprise—in addition to a bioactive agent and/or a genetic determinant, preferably a polynucleotide, i) a lipophilic moiety, optionally a lipophilic moiety comprising a contacting group and/or a targeting ligand, and/or ii) a saccharide moiety, preferably, but not limited to a saccharide moiety forming part of a naturally occurring saponin. It is particularly preferred that the complexes according to the invention comprise a saccharide moiety when it is intended to direct the complexes to cellular surfaces known to contain saccharide binding receptors.

The complexes according to the invention may thus further comprise a bioactive agent and/or a genetic determinant and/or an immunogenic determinant and/or an antigenic determinant and/or a medicament and/or a therapeutic agent and/or a diagnostic agent.

The complexes may in even further embodiments be encapsulated by an encapsulation agent including a liposome and/or a biodegradable microsphere. By analogy to the complexes, the liposome and/or the biodegradable microsphere may comprise a targeting ligand suitably associated with the microsphere for targeting the microsphere to a particular location in a human or animal body. Preferred targeting ligands include, but are not limited to, ligands having affinity to receptors on antigen presenting cells, including e.g. dendritic cells and macrophages. When used for therapeutic purposes, the ligands are targeted to e.g. vitamin receptors, folate receptors, high affinity IL-2 receptors, growth factor receptors, such as EGF-receptors, and the like.

First saponins and/or second saponins and/or first sterols and/or second sterols may also be present in e.g. the biodegradable microsphere. It is particularly preferred in one embodiment that the microsphere has an overall positive charge, i.e. contains more positively charged groups than negatively charged groups.

The present invention also pertains to pharmaceutical compositions and methods of treatment of an individual by therapy and/or surgery, methods of cosmetic treatment, and diagnostic methods practised on the human or animal body.

There is also provided a method for manufacturing the complexes according to the invention, and in even further aspects the present invention relates to using the complexes according to the invention, or compositions comprising such complexes, including pharmaceutical compositions, in the manufacture of a medicament for treating a condition in an individual in need of such treatment.

In addition, the present invention relates to a kit-of-parts, wherein said kit-of-parts comprises a complex according to the invention and at least one immunogenic determinant. The present invention also relates to a kit-of-parts, wherein said kit-of-parts comprises a complex according to the invention and at least one immunogenic determinant and at least one genetic determinant. For example the immunogenic determinant may comprise an antigenic determinant.

The kit-of-parts according to the invention—as well as the complexes themselves—can be used in a method for raising a desirable immune response in a patient. Said method comprise the steps of i) providing a complex according to the invention, and ii) providing a genetic determinant such as a polynucleotide such as DNA and/or iii) providing an immunogenic determinant such as antigenic determinant such as a peptide such as an epitope, iv) mixing said complex with said genetic determinant and/or said immunogenic determinant, v) administering said mixture to a patient in an amount effective to raise a desirable immune response in said patient, and vi) raising said desirable immune response.

In preferred embodiments, the method comprises the further step of administering, simultaneously or sequentially in any order, a) a complex comprising a genetic determinant, and b) a complex comprising an immunogenic determinant such as an antigenic determinant. The genetic determinant in one embodiment encodes the immunogenic/antigenic determinant, or part thereof. The immunogenic determinant Is preferably a lipid associated peptide (lipo-peptide, e.g. a lipoprotein or a part thereof). When the above method comprises the steps of sequentially administering a) a complex comprising a genetic determinant, and b) a complex comprising an immunogenic determinant, it is thus possible to administer initially a genetic determinant and then boost after a suitable time period any initial immune response by subsequently administering a complex comprising an immunogenic determinant, preferably an immunogenic determinant comprising an epitope encoded by the initially administered genetic determinant. Initial administration of an immunogenic determinant followed by administration after a suitable time period of a genetic determinant. Likewise, it is possible to administer to a patient—simultaneously or sequentially in any order—i) a complex comprising a genetic determinant, and ii) a peptide including an epitope administered according to any state of the art method, as well as administering to said patient—simultaneously or sequentially in any order—i) a complex comprising an immunogenic determinant, including a peptide epitope, and ii) a polynucleotide such as DNA administered according to any state of the art method.

The above complexes, or the individual components thereof, as well as the genetic and immunogenic determinants can be provided in individual vials ready for use in a kit-of-parts. In this way it is possible to mix complexes according to the invention with genetic determinants, such as polynucleotides, such as DNA, and/or with immunogenic determinants such as antigenic determinants, such as peptides, such as epitopes.

Definitions

Aglycone: Part of a saponin glycoside, linked to saccharide part through a glycosidic bond.

Amphiphilic moiety. Any moiety, including a lipid, comprising a synthetic, semi-synthetic (modified natural) or naturally-occurring compound having a water-soluble, hydrophilic portion and a water-insoluble, hydrophobic portion.

Preferred amphiphilic compounds are characterized by a polar head group, for example, a phosphatidylcholine group, and one or more nonpolar, aliphatic chains, for example, palmitoyl groups.

Antigenic determinant: Any determinant or substance with the capability of binding an antibody, or a binding fragment thereof, and inducing a specific antigen response. The antigenic determinant may comprise or essentially consist of an epitope that forms part of a polypeptide and elicits a specific antibody response when the whole polypeptide is used as an antigen. Such epitopes are confined to a single or a few loci on the molecule in question.

Bioactive agent: Any a substance which may be used in connection with an application that is therapeutic or diagnostic, such as, for example, in methods for diagnosing the presence or absence of a disease in a patient and/or methods for the treatment of a disease in a patient. "Bioactive agent" refers to substances, which are capable of exerting a biological effect in vitro and/or in vivo. The bioactive agents may be neutral, positively or negatively charged. Suitable bioactive agents include, for example, prodrugs, diagnostic agents, therapeutic agents, pharmaceutical agents, drugs, oxygen delivery agents, blood substitutes, synthetic organic molecules, proteins, peptides, vitamins, steroids, steroid analogs and genetic determinants, including nucleosides, nucleotides and polynucleotides.

Cationic lipid: Any lipid carrying a net positive charge at pH 7.0.

Cationic saponin: Any saponin carrying a net positive charge at pH 7.0.

Cationic sterol: Any sterol carrying a net positive charge at pH 7.0.

Contacting group: Group comprising a lipophilic moiety and a moiety capable of association with a genetic determinant by means of either i) electrostatic interaction, or ii) hydrophobic interaction.

Complex: Formation of saponins and sterols capable of interacting with genetic determinants or immunogenic determinants. The interaction can result from electrostatic interactions and/or hydrophobic interactions formed between on the one hand i) a saponin and/or a sterol, and on the other hand ii) a genetic determinant and/or an immunogenic determinant. When this is the case, the, saponin and/or the sterol is termed a second saponin and/or a second sterol, respectively. Complexes devoid of second saponins and second sterols form electrostatic and/or hydrophobic interactions with genetic determinants and/or immunogenic determinants by means of a contacting group. When the contacting group forms part of a saponin or a sterol, said saponin or sterol is by definition a second saponin or a second sterol. Contacting groups may be present in a complex independently of the presence of second saponins and/or second sterols. Accordingly, contacting groups can be present in a complex also comprising second saponins and/or second sterols without said contacting group forming part of said second saponins and/or second sterols. The overall charge of a second saponin or a second sterol can be neutral or even anionic, as long as the contacting group of the saponin or sterol in question comprises at least one positively charged moiety at pH=7 capable of forming an association with a genetic determinant. Contacting groups can also be neutral in which case predominantly hydrophobic interactions with a genetic determinant are formed.

Degenerated polynucleotide sequence: Polynucleotide encoding a polypeptide and comprising an altered sequence of nucleotides as compared to a polynucleotide comprising a predetermined sequence of nucleotides and encoding a predetermined polypeptide, wherein the polypeptide and the predetermined polypeptide have the same biological activity.

Diagnostic agent: Any agent which may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, radiofrequency (RF) and microwave laser. Diagnostic agents may also include any other agents useful in facilitating diagnosis of a disease or other condition in a patient, whether or not imaging methodology is employed. As defined herein, a "diagnostic agent" is a type of bioactive agent.

Diagnostic method: Any method involving an outcome aiding the medical practitioner in reaching a diagnosis of a clinical condition.

Dipole-dipole interaction: The attraction which can occur among two or more polar molecules. Thus, "dipole-dipole interaction" refers to the attraction of the uncharged, partial positive end of a first polar molecule to the uncharged, partial negative end of a second polar molecule. Dipole-dipole interactions are exemplified by the attraction between the electropositive head group, for example, the choline head group, of phosphatidylcholine, and an electronegative atom, for example, a heteroatom, such as oxygen, nitrogen or sulphur "Dipole-dipole interaction" also refers to intermolecular hydrogen bonding in which a hydrogen atom serves as a bridge between electronegative atoms on separate molecules and in which a hydrogen atom is held to a first molecule by a covalent bond and to a second molecule by electrostatic forces.

Electrostatic interaction: Any interaction occurring between charged components, molecules or ions, due to attractive forces when components of opposite electric charge are attracted to each other. Examples include, but are not limited to: ionic interactions, covalent interactions, interactions between a ion and a dipole (ion and polar molecule), interaction between two dipoles (partial charges of polar molecules), hydrogen bonds, i.e. hydrogen bonded to e.g. i) a nitrogen atom, an oxygen atom, or a fluor atom in one molecule, while at the same time being bonded to ii) a nitrogen atom, an oxygen atom, or a fluor atom in another molecule or the same molecule, interchelating interactions, and London dispersion bonds (induced dipoles of polarizable molecules). Thus, for example, "ionic interaction" or "electrostatic interaction" refers to the attraction between a first, positively charged molecule and a second, negatively charged molecule. Ionic or electrostatic interactions include, for example, the attraction between a negatively charged bioactive agent, for example, a genetic determinant, and one or more of i) a positively charged lipid, for example, a cationic lipid, ii) a positively charged saponin, for example a cationic saponin, and iii) a positively charged sterol, for example a cationic sterol.

Genetic determinant: Genetic determinant refers to nucleotides and polynucleotides, including deoxyribonucleic acid (DNA) and ribonucleic acid (RNA). The genetic determinant may be made by synthetic chemical methodology known to one of ordinary skill in the art, or by the use of recombinant technology, or by a combination thereof. The DNA and RNA may optionally comprise unnatural nucleotides or nucleotide derivatives including LNA (locked nucleic acids) and PNA (peptide nucleic acids), and it may be single or double stranded. "Genetic determinant" also refers to sense and antisense DNA and RNA, which are nucleotide sequences which are complementary to specific sequences of nucleotides in DNA and/or RNA.

Hydrogen bond: An attractive force, or bridge, which may occur between a hydrogen atom which is bonded covalently to an electronegative atom, for example, oxygen, sulfur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

Hydrophobic interaction: Any interaction occurring between essentially non-polar (hydrophobic) components located within attraction range of one another in a polar environment (e.g. water). As used herein, attraction range is on the scale of about 100 nm. A particular type of hydrophobic interaction is exerted by "Van der Waal's forces", i.e. the attractive forces between non-polar molecules that are accounted for by quantum mechanics. Van der Waal's forces are generally associated with momentary dipole moments which are induced by neighboring molecules and which involve changes in electron distribution.

Immunogenic determinant: Any determinant or substance with the capability of raising an immune response, such as a specific or non-specific antibody response, or a cytolytic response. The immunogenic determinant may comprise or essentially consist of an epitope that forms part of a polypeptide and elicits an immune response when the whole polypeptide is used as an immunogen. Such epitopes are confined to a single or a few loci on the molecule in question.

Interaction: Transient or longer lasting attraction or binding of two or more moieties to one another, mediated by physical forces such as e.g. electrostatic interactions and hydrophobic interactions.

Intercalation: Intercalation specifically denotes the association between a contacting group and a genetic determinant wherein the contacting group form a complex with two adjacent layers of purine-pyrimidine base-pairs of the genetic determinant. The intercalating group is oriented in parallel to the base-pairs and interacts with the genetic determinant by hydrogen bond forces, electrostatic interactions and/or hydrophobic interactions.

Iscom structure: Rigid, cage-like matrix characterised by an icosahedral symmetry, about 30 to 40 nanometers in diameter, and composed of 12 nanometer ring-like subunits.

Essentially non-polar: Nature of compounds or domains capable of contacting or interacting with lipids or lipophilic moieties of a similar nature.

Lipophilic moiety: Moiety attached to or in contact with either i) any suitable functional group of one or more compounds that is essentially non-polar, or ii) moiety forming an essentially non-polar domain within the complexes according to the present invention. Preferred lipophilic moieties are a naturally-occurring, synthetic or semi-synthetic (modified natural) compound which is generally amphipathic. Lipids typically comprise a hydrophilic component and a hydrophobic component. The phrase semi-synthetic (modified natural) denotes a natural compound that has been chemically modified in some fashion. Lipids are also referred to herein as "stabilizing materials" or "stabilizing compounds."

Liposome: A generally spherical or spheroidal cluster or aggregate of amphipathic compounds, including lipophilic moieties, typically in the form of one or more concentric layers, for example, monolayers, bilayers or multi-layers. They may also be referred to herein as lipid vesicles. The liposomes may be formulated, for example, from ionic lipids and/or non-ionic lipids. Liposomes formulated from non-ionic lipids may be referred to as niosomes. Liposomes formulated, at least in part, from cationic lipids or anionic lipids may be referred to as cochleates.

Patient: Any member, individual, or "animal body" of the subphylum chordata, including, without limitation, mammals such as cattle, sheep, pigs, goats, horses, and humans, preferably humans; domestic animals such as dogs and cats; and birds, including domestic, wild and game birds such as cocks and hens including chickens, turkeys and other gallinaceous birds. The term also covers fish, and it does not denote any particular age. Thus, both adult and newborn animals are intended to be covered.

Phospholipid; Any moiety consisting of a glycerol backbone, a hydrophobic part comprising a phosphate group, and a lipophilic part in the form of two fatty acids.

Polynucleotide: A molecule comprising at least two nucleic acids. The nucleic acids may be naturally occurring, or locked nucleic acids (LNA), or peptide nucleic acids (PNA). Polynucleotide as used herein generally pertain to
  i) a polynucleotide comprising a predetermined coding sequence, or
  ii) a polynucleotide encoding a predetermined amino acid sequence, or
  iii) a polynucleotide encoding a fragment of a polypeptide encoded by polynucleotides (i) or (ii), wherein said fragment has at least one predetermined activity as specified herein; and
  iv) a polynucleotide the complementary strand of which hybridizes under stringent conditions with a polynucleotide as defined in any one of (i), (ii) and (iii), and encodes a polypeptide, or a fragment thereof, having at least one predetermined activity as specified herein; and
  v) a polynucleotide comprising a nucleotide sequence which is degenerate to the nucleotide sequence of polynucleotides (iii) or (iv);
  or the complementary strand of such a polynucleotide.

Polypeptide: A molecule comprising at least two amino acids. The amino acids may be natural or synthetic.

Positively charged moiety: Any moiety comprising a positive electrical charge capable of attracting a negative electrical charged moiety. Positively charged moieties are typically found in cationic species, one of which is a species comprising at least one positively charged moiety at pH=7.0.

Quil A: Quillajabark Araloside A, a crude saponin mixture containing QA-7, QA-17, QA-18, and QA-21 as well as other saponins.

Region of a patient: A particular area or portion of the patient and in some instances to regions throughout the entire patient. Exemplary of such regions are the pulmonary region, the gastrointestinal region, the cardiovascular region (including, myocardial tissue), the renal region as well as other bodily regions, tissues, lymphocytes, receptors, organs and the like, including the vasculature and circulatory system, and as well as diseased tissue, including cancerous tissue. "Region of a patient " includes, for example, regions to be treated with a bioactive agent, regions to be targeted for the delivery of a bioactive agent, and regions to be imaged with diagnostic imaging. The "region of a patient" is preferably internal, although, if desired, it may be external. The phrase "vasculature" denotes blood vessels (including arteries, veins and the like). The phrase "gastrointestinal region" includes the region defined by the esophagus, stomach, small and large intestines, and rectum. The phrase "renal region" denotes the region defined by the kidney and the vasculature that leads directly to and from the kidney, and includes the abdominal aorta.

Receptor: A molecular structure within a cell or on the surface of a cell which is generally characterized by the selective binding of a specific substance. Exemplary receptors include cell-surface receptors for peptide hormones, neurotransmitters, antigens, complement fragments, immunoglobulins and cytoplasmic receptors.

Saccharide: Sugar part of saponins according to the present invention.

Saponin: Any compound comprising a saccharide part linked by means of a glycosidic bond to one of i) a triterpene aglycone part, ii) a steroid aglycone part, and iii) a steroid alkaloid aglycone part. Saponin as used herein denotes either a sub substantially purified saponin, or one or more saponins comprised in a crude composition or a composition obtained by predetermined purification means. Saponin shall also denote any biologically active fragment of any saponin. The saponins pertaining to the present invention may be naturally occurring or synthetic, or they may be made by chemical synthesis, or enzymatic synthesis involving one or more enzyme catalysed steps, either in vitro or in vivo. First saponins are generally incapable of forming an association with a genetic determinant as defined herein, whereas such an association is formed between second saponins and the genetic determinant.

Second saponin: Second saponins may be either anionic, neutral, or cationic. Second saponins are capable of forming an electrostatic interaction and/or a hydrophobic interaction with a bioactive agent, including a genetic determinant. The term cationic saponin shall denote a saponin carrying a net positive charge at pH 7.0. Second saponins are preferably cationic saponins. Alternatively, second saponins preferably comprises at least one moiety carrying a positive charge at pH 7.0 regardless that the overall net charge is not positive. Accordingly, second saponins preferably comprise at least one positively charged moiety or reactive group at pH=17.0, and this positively charged moiety or reactive group is according to one preferred embodiment of the invention capable of contacting a bioactive group, including a genetic determinant, by means of an electrostatic interaction. In another embodiment, a second saponin preferably comprises an uncharged moiety or non-polar reactive group capable of contacting a bioactive group, including a genetic determinant, by means of a hydrophobic interaction. One group of preferred second saponins are saponins comprising as the aglycone part a synthetic or naturally occurring, cationic quillaic acid, or a quillaic acid comprising at least one positively charged group at pH=7.0.

Sterol: Any sterol, including any derivative thereof comprising the characteristic skeleton structure of a steroid as depicted herein below in the form of gonane. All steroids are related to a characteristic molecular structure composed of 17 carbon atoms arranged in four rings conventionally denoted by the letters A, B, C, and D and bonded to 28 hydrogen atoms.

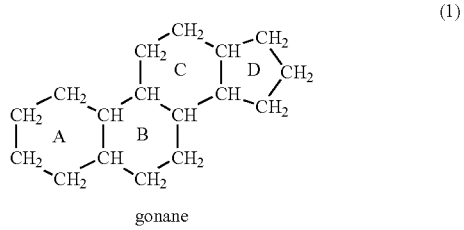

gonane

This skeleton structure (1) is named gonane and often referred to as the steroid nucleus. This skeleton structure may be modified in a practically unlimited number of ways by removal, replacement, or addition of a few atoms, moieties or reactive groups at a time. The skilled artisan will know how to isolate steroids from plants and animals, and optionally prepare derivatives by chemical and/or enzymatic treatment of natural steroids. The skilled artisan will also know how to synthesize synthetic steroids from simpler compounds, or natural precursors or parts thereof, and optionally prepare derivatives of such compounds by chemical and/or enzymatic treatment of steroids thus obtained. Accordingly, one preferred steroid compound according to the invention is a stereol, and any cationic derivative thereof, in particular cationic derivatives obtained by linking a cationic moiety, or a cationic reactive group, to e.g. an OH-group of the stereol including an OH-group located at position 3 of the steroid skeleton, including the OH-group of cholesterol located at position 3 (C3, or 3-OH). Consequently, preferred sterols according to the present invention are cholesterol (CAS (Chemical Abstract) accession no. 57-88-5) and any cationic derivative thereof, in particular cationic derivatives obtained by linking a cationic moiety, or a cationic reactive group, to the OH-group located at position 3 of the steroid skeleton (C3, or 3-OH). Preferred examples of such compounds are illustrated in FIG. 5. First sterols are generally incapable of forming an association with a genetic determinant as defined herein, whereas such an association is formed between second sterols and the genetic determinant.

Second sterol: Second sterols may be either anionic, neutral, or cationic. Second sterols are capable of forming an electrostatic interaction and/or a hydrophobic interaction with a bioactive agent, including a genetic determinant The term cationic sterol shall denote a sterol carrying a net positive charge at pH 7.0 Second sterols are preferably cationic sterols. Alternatively, second sterols preferably comprises at least one moiety carrying a positive charge at pH 7.0 regardless that the overall net charge is not positive. Accordingly, second sterols preferably comprise at least one positively charged moiety or reactive group at pH=7.0, and this positively charged moiety or reactive group is according to one preferred embodiment of the invention capable of contacting a bioactive group, including a genetic determinant, by means of an electrostatic interaction. In another embodiment, the second sterol preferably comprises an uncharged moiety or non-polar reactive group, and this uncharged moiety or non-polar reactive group is according to another preferred embodiment of the invention capable of contacting a bioactive group, including a genetic determinant, by means of a hydrophobic interaction.

Steroid alkaloid glycoside: Saponin comprising a saccharide part linked by means of a glycosidic bond to a steroid alkaloid aglycone part.

Steroid glycoside: Saponin comprising a saccharide part linked by means of a glycosidic bond to a steroid aglycone part.

Stringent conditions: Stringent conditions as used herein shall denote stringency as normally applied in connection with Southern blotting and hybridization as described e.g. by Southern E. M., 1975, J. Mol. Biol. 98;503-517. For such purposes it is routine practise to include steps of prehybridization and hybridization. Such steps are normally performed using solutions containing 6× SSPE, 5% Denhardt's, 0.5% SDS 50% formamide, 100 µg/ml denaturated salmon testis DNA (incubation for 18 hrs at 42° C.), followed by washings with 2× SSC and 0.5% SDS (at room temperature and at 37° C.), and a washing with 0.1× SSC and 0.5% SDS (incubation at 68° C. for 30 min), as described by Sambrook et al., 1989, in "Molecular Cloning/A Laboratory Manual", Cold Spring Harbor), which is incorporated herein by reference.

Substantially pure saponin: Saponin substantially free from compounds normally associated with the saponin in its natural state, wherein the saponin exhibits a constant and reproducible chromatographic response and/or elution pro-file and/or biologic activity. The term "substantially pure" as used herein is not meant to exclude artificial or synthetic mixtures of the saponin with other compounds. Preferably, the substantially pure saponin is purified to one or more of the following standards: i) Appearing as only one major carbohydrate staining band on silica gel TLC (EM Science HPTLC Si60) in a solvent system of 40 mm acetic acid in chloroform/methanol/water (60/45/10, v/v/v), ii) Appearing as only one major carbohydrate staining band on reverse phase TLC (EM Science Silica Gel RP-8) in a solvent system of methanol/water (70/30, v/v), 3) Appearing as only one major peak upon reverse-phase HPLC on Vydac C4 (5 µm particle size, 330 Ångstrøm pore, 4.6 mm ID×25 cm L) in 40 mM acetic acid in methanol/water (58/42, v/v).

Targeting ligand: Any material or substance which, when comprised in a complex according to the invention, is capable of promote targeting of tissues and/or receptors in vivo or in vitro with the complexes of the present invention, or compositions such as e.g. biodegradable microsphere or liposomes comprising such complexes. In the latter case the compositions comprise the targeting ligand independently of whether or not the complexes also comprise the targeting ligand. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic determinants, including nucleosides, nucleotidies, nucleotide acid constructs, polynucleotides, optionally constructs or polynucleotides comprising derivatised nucleotides such as PNA (peptide nucleic acid) and/or LNA (locked nucleic acid). A "precursor" to a targeting ligand refers to any material or substance capable of being converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and α-iodo acetyl groups.

Therapeutic agent: The terms "pharmaceutical agent" or "drug" or "medicament" refers to any therapeutic or prophylactic agent which may be used in the treatment (including the prevention, diagnosis, alleviation, or cure) of a malady, affliction, condition, disease or injury in a patient. Therapeutically useful genetic determinants, peptides, polypeptides and polynucleotides may be included within the meaning of the term pharmaceutical or drug. As defined herein, a "therapeutic agent," "pharmaceutical agent" or "drug" or "medicament" is a type of bioactive agent.

Tissue: Specialized cells which may perform a particular function. The term "tissue" may refer to an individual cell or a plurality or aggregate of cells, for example, membranes or organs. The term "tissue" also includes reference to an abnormal cell or a plurality of abnormal cells. Exemplary tissues include pulmonary tissue, myocardial tissue, including myocardial cells and cardiomyocites, membranous tissues, including endothelium and epithelium, laminae, blood, connective tissue, including interstitial tissue, and tumors. "Cell" refers to any one of the minute protoplasmic masses which make up organized tissue, comprising a mass of protoplasm surrounded by a membrane, including nucleated and unnucleated cells and organelles.

Treatment: Method involving therapy including surgery of a clinical condition in an individual including a human or animal body. The therapy may be profylactic, ameliating or curative.

Triterpene glycoside: Saponin comprising a saccharide part linked by means of a glycosidic bond to a triterpene aglycone part.

Zeta potential: The parameter of zeta potential is a measure of the magnitude of the repulsion or attraction between particles. Its measurement relates to some extent to the overall charge of particles but also to the stability of particles in dispersion. The surface charge of particles in polar liquids dose not directly correlate to the electrical potential at the surface of the particle but to the potential that in the close vicinity of the particle.

Detailed Description of the Invention

The present invention is related to complexes which are capable of binding bioactive agents such as e.g. genetic determinants such as for example polynucleotides, therapeutic agents, e.g. polypeptides, diagnostic agents and imaging agents. When attached to the complexes according to the invention, the bioactive agents are capable of being taken up by a biological cell including a human or animal cell. The complexes according to the invention are thus useful as a means for transfecting a biological cell with e.g. a polynucleotide either in vivo or in vitro.

In other preferred embodiments there are provided methods of delivering bioactive agents to a patient and/or treating conditions in a patient comprising administering to the patient a complex according to the invention, or a composition comprising such a complex.

The present invention describes methods of delivering bioactive agents to a patient and/or treating conditions in a patient comprising administering to the patient a complex according to the invention, or a composition comprising such a complex.

The present invention also describes methods of diagnosing the presence of diseased tissue in a patient comprising administering to the patient a complex according to the invention, or a composition comprising such a complex.

The present invention also describes methods of providing an image of an internal region of a patient comprising administering to the patient a complex according to the invention, or a composition comprising such a complex.

| | Recorded mean value (mV) | Width (mV) | Conductivity (mS/cm) | Title |
|---|---|---|---|---|
| 16 | −51.6 | 6.3 | 0.300 | Std. ISCOM |
| 17 | −45.0 | 6.2 | 0.362 | Std. ISCOM |
| 18 | −51.7 | 6.1 | 0.215 | Std. ISCOM |
| 19 | −50.8 | 6.3 | 0.379 | Std. ISCOM |
| 20 | −45.9 | 6.3 | 0.317 | Std. ISCOM |

Figure 12:
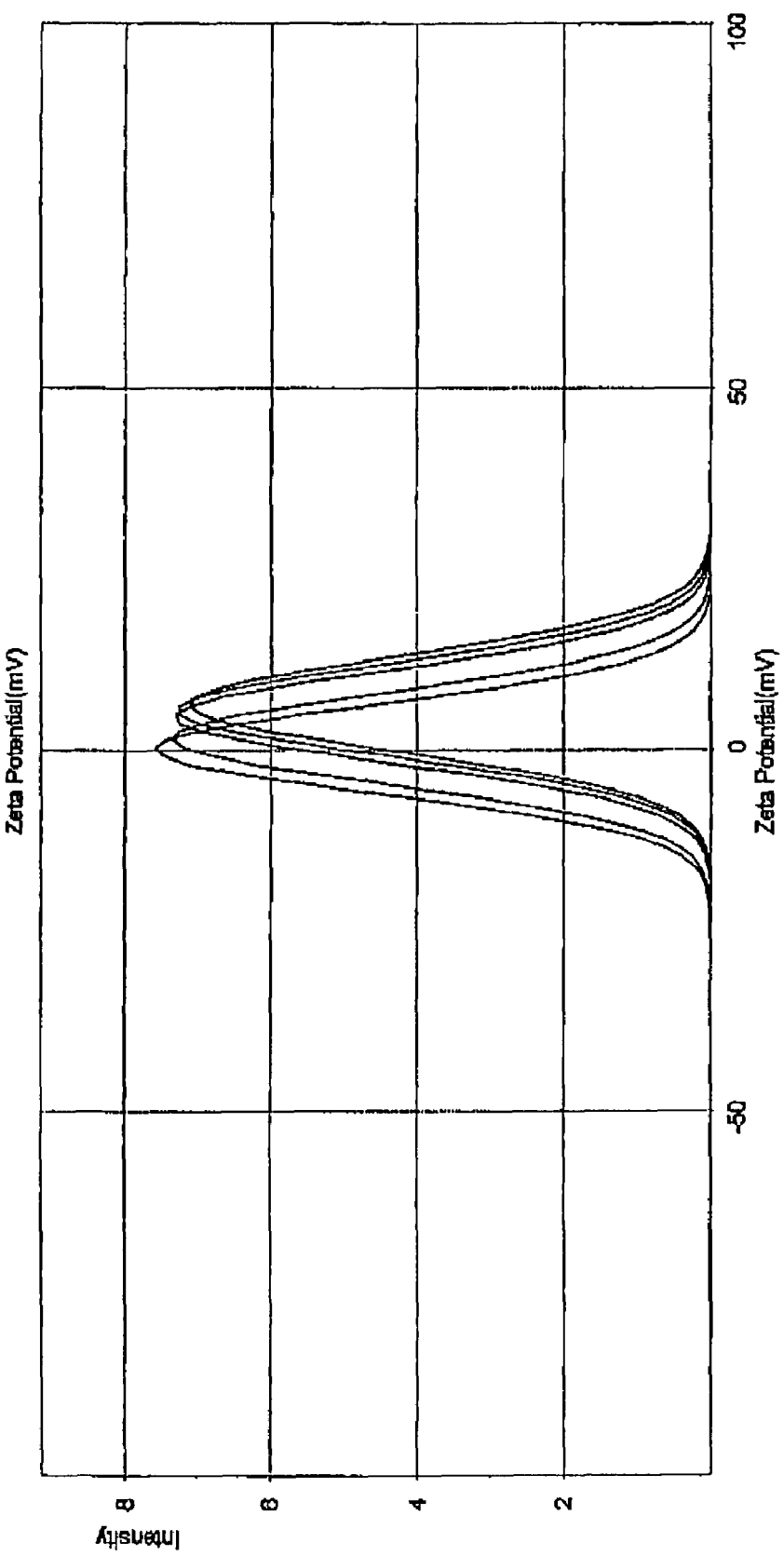

FIG. 12 Illustrates measurements of zeta potentials for modified ISCOMs comprising a second sterol in the form of DC-cholesterol. The DC-cholesterol to cholesterol ration was 1:1 (50% substitution). Each curve represents one of five measurements. The Zeta-potential was close to 0 mV with some variation between measurements (see table below). When ISCOMs with a DC-cholesterol to cholesterol of 1:2 (25%) were measured an average Zeta-potential of approx. −25mV observed (data not shown).

| | Recorded mean value (mV) | Width (mV) | Conductivity (mS/cm) | Title |
|---|---|---|---|---|
| 11 | 2.0 | 6.4 | 0.172 | DC-CH 50% |
| 12 | 6.0 | 6.5 | 0.182 | DC-CH 50% |
| 13 | 0.5 | 6.2 | 0.216 | DC-CH 50% |
| 14 | 6.7 | 6.6 | 0.169 | DC-CH 50% |
| 15 | 5.0 | 6.4 | 0.159 | DC-CH 50% |

SAPONINS

Saponins pertaining to the present invention are described in detail herein below. Saponins are glycosidic compounds which comprises an aglycone compound and a saccharide compound linked together by a glycosidic bond. The asymmetric distribution of their hydrophobic (aglycone) and hydrophilic (saccharide) moieties confers an amphipathic character to the saponins according to the present invention.

Saponins are produced by many organisms as secondary metabolites. They are widely distributed among higher plants and in some marine invertebrates. Plant material often contains triterpene saponins in considerable amounts. Thus, primula root contains about 5-10% saponin, licorice root between 2% and 12% glycyrrhizin, quillaia bark up to 10% of a saponin mixture and the seeds of the horse chestnut up to 13% aescine. In other words, the concentration of saponins in plants is high when compared with other secondary metabolites.

Figure 1:
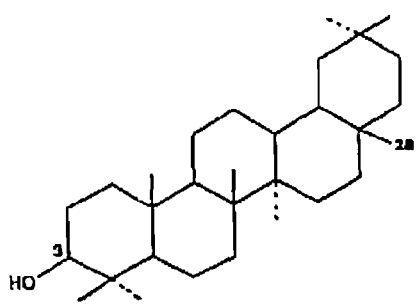
FIG. 1 illustrates the carbon skeleton of the three main classes of saponins according to the invention. Depending on the type of genin present, the saponins according to the invention can be divided into three major classes: i) triterpene glycosides, ii) steroid glycosides, and iii) steroid alkaloid glycosides.
Figure 1:
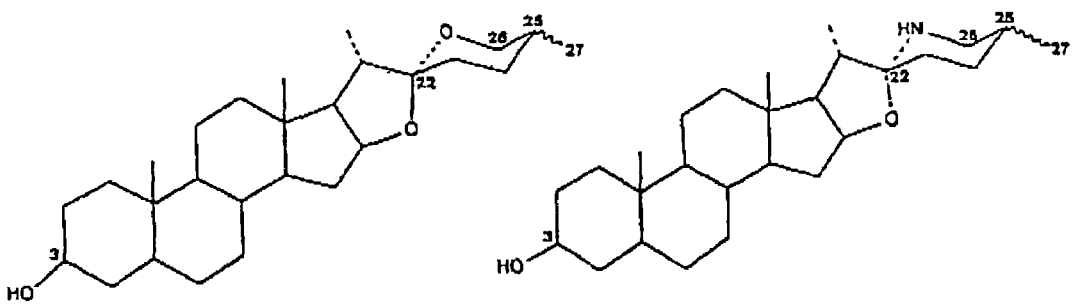

The aglycone or non-saccharide portion of the saponin molecule is called the genin or sapogenin. Depending on the type of genin present, the saponins can be divided into three major classes, i) triterpene glycosides, ii) steroid glycosides, and iii) steroid alkaloid glycosides (FIG. 1).

In addition to saponins comprising trite pene saponins, the present invention also pertains to saponins comprising steroid sapogenins derived from a furostan skeleton or a spirostan skeleton. The present invention further pertains to saponins comprising steroid alkaloid sapogenins derived from a solanidan skeleton or a spirosolan skeleton. The steroid alkaloid glycosides, or glycoalkaloids, share many physical and biological properties with steroid glycosides, but alkaloid glycosides are usually considered separately because their steroidal structure contains nitrogen.

Saponins Comprising a Triterpene Glycoside

Figure 2:
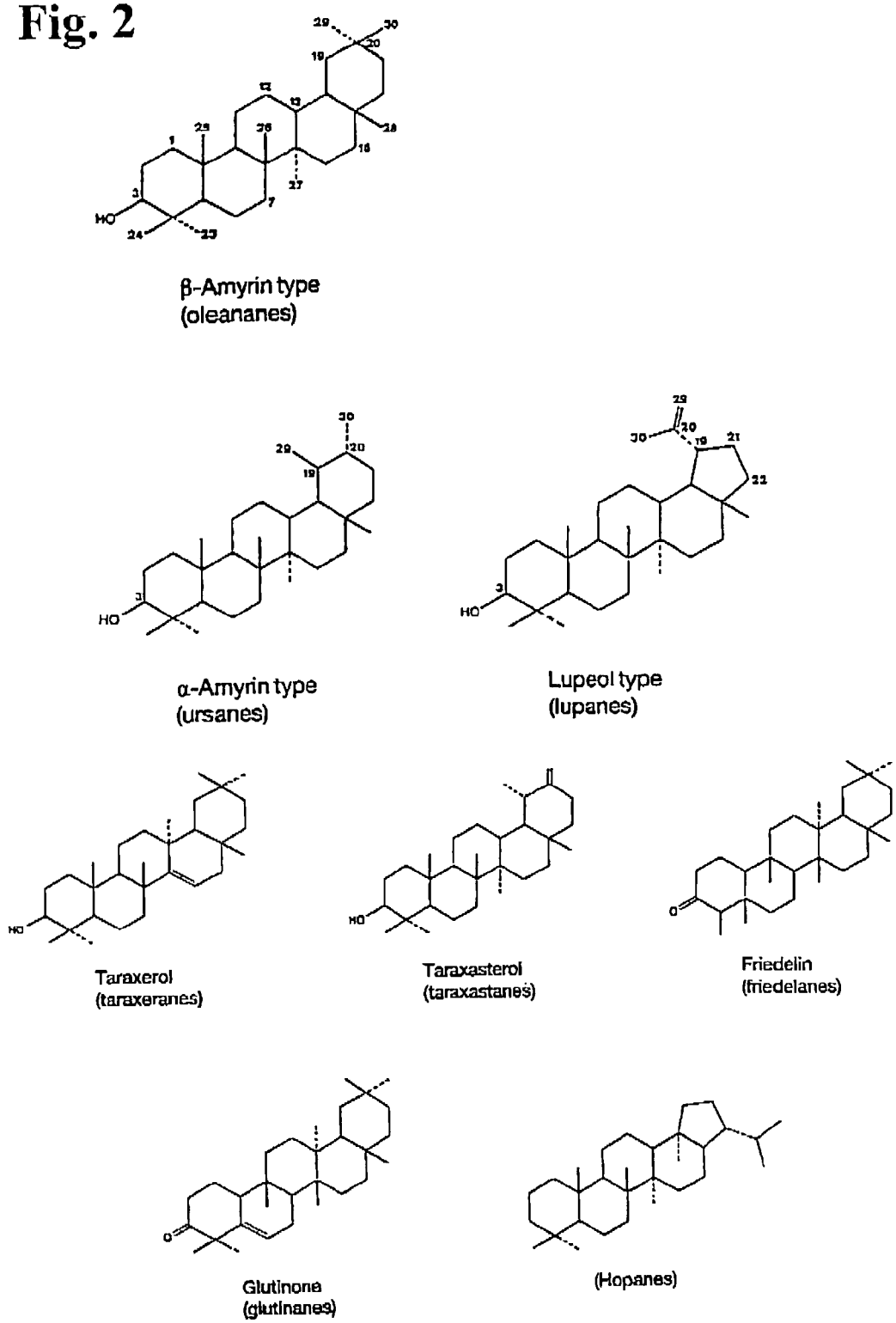
FIG. 2 illustrates the carbon skeleton of various pentacyclic triterpenes divided into three main classes, depending on whether they have a β-amyrin, α-amyrin or lupeol skeleton. In addition thereto, several minor classes also exist. The aglycone skeleton of the following triterpene glycosides are illustrated in the figure: Oleane (β-Amyrin), Ursane (α-Amyrin), Lupane, Taraxastane, Taraxerane, Friedelane, Glutinane, and Hopane.

Triterpene glycosides represent one preferred class of saponins according to the present invention. The pentacyclic triterpenes can be divided into three main classes, depending on whether they have a βamyrin, α-amyrin or lupeol skeleton. In addition thereto, several minor classes also exist as illustrated in FIG. 2.

According to the present invention, saponins in the form of triterpene glycosides preferably comprises an aglycone skeleton selected from the group of compounds consisting of Oleane (β-Amyrin), Ursane (α-Amyrin), Lupane, Taraxastane, Friedelane, Glutinane, Hopane, Dammarane, Lanostane, Holostane, and Cycloartane.

The triterpene aglycone may be hydroxylated at C-3 and certain methyl groups may be oxidized to hydroxymethyl, aldehyde or carboxyl functionalities. When an acid moiety is esterified to the triterpene aglycone, the term ester saponin is used for the respective glycosides. Further important structural elements of this class is: The unsaturation at C-12(13); the functionalization of the methyl group of C-28, C-23 or C-30; and polyhydroxylation at C-2, C-7, C-11, C-15, C-16, C-19. The formation of an additional ring structure is possible through etherification or lactonization, and esterification by aliphatic acids is also possible.

Figure 3:
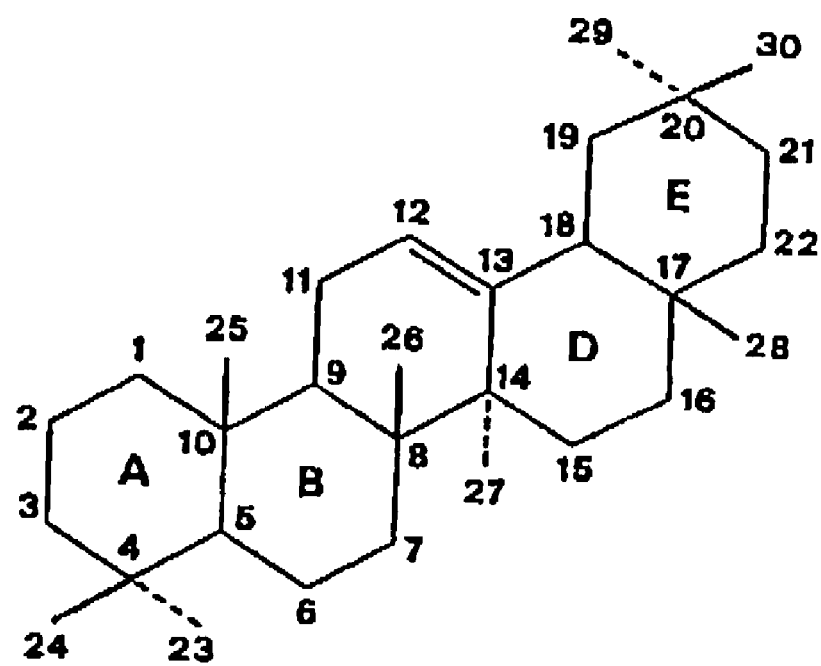
FIG. 3 illustrates the olean-12-en skeleton of triterpene glycosides. A number of such aglycone variants pertaining to the present invention are listed in Table 1 herein.

There are numerous structural variants of the triterpene glycoside class of saponins comprising a oleanane skeleton (olean-12-en skeleton). A number of such aglycone variants pertaining to the present invention are listed in Table 1 herein below. Their skeleton is Illustrated in FIG. 3.

Figure 4:
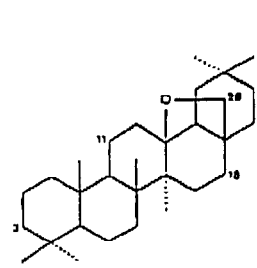
FIG. 4 Illustrates other representative variants of triterpene aglycones according to the present invention and listed in Table 2 herein. The aglycones of FIG. 4 are representative of aglycones which do not have an olean-12-en skeleton. Examples are listed in Table 2 herein.
Figure 4:
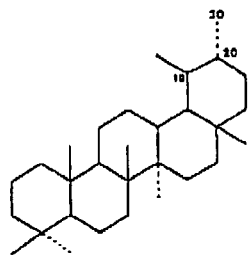
Figure 4:
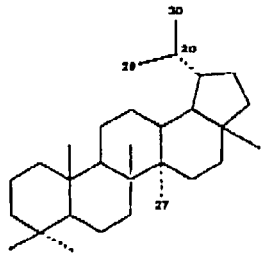
Figure 4:
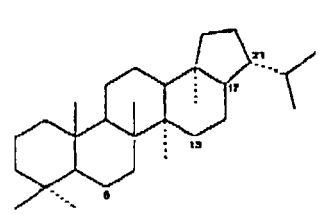
Figure 4:
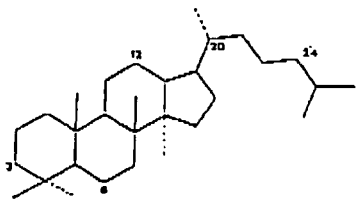
Figure 4:
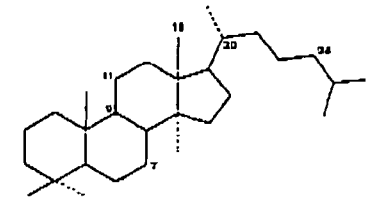
Figure 4:
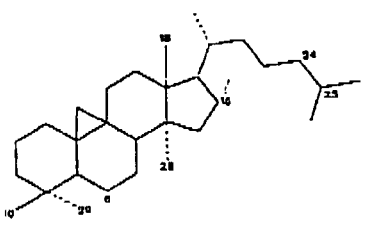
Figure 4:
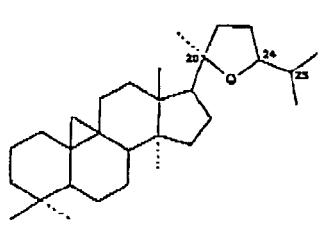
Figure 4:
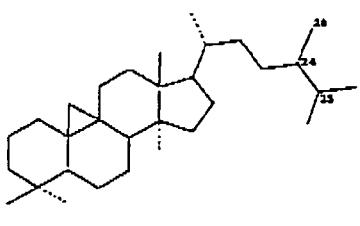

Other representative variants of triterpene aglycones according to the present invention are listed in Table 2. The aglycones of Table 2 are representative of aglycones which do not have an olean-12-en skeleton. Examples of such skeletons are illustrated in FIG. 4

A review article by Tschesche and Wulff (1972), incorporated herein by reference, gives further references and examples, together with physical constants, of both oleananes and other triterpenes. Mahato and co-workers (Das and Mahato, 1983; Mahato et al. 1992; both of which are incorporated herein by reference) have published lists of recently isolated triterpenes (not necessarily from saponins) with their physical constants and plant sources.

Oleanane triterpenes (and some of their glycosides) have been the subject of an update (Mallavarapu, 1990: incorporated herein by reference), covering various aspects of their occurrence and chemistry. Another authoritative source of information on the triterpenes is the book written by Boiteau and colleagues (1964; incorporated herein by reference).

TABLE 1

Structures of commonly occurring olean-12-en aglycones

| No. | Olean-12-en aglycone | —OH | =O | —COOH | Other |
|---|---|---|---|---|---|
| 1 | β-Amyrin | 3β | | | |
| 2 | Oleanolic acid | 3β | | 28 | |
| 3 | Epikatonic acid | 3β | | 29 | |
| 4 | α-Boswellic acid | 3α | | 24 | |
| 5 | Momordic acid | 3β | 1 | 28 | |
| 6 | Glycyrrhetinic acid | 3β | 11 | 30 | |
| 7 | Gypsogenin | 3β | 23 | 28 | |
| 8 | Gypsogenic acid | 3β | | 23,28 | |
| 9 | Cincholic acid | 3β | | 27,28 | |
| 10 | Serjanic acid (30-O-methyl-spergulagenate) | 3β | | 28 | 30-COOMe |
| 11 | Maniladiol | 3β,16β | | | |
| 12 | Sophoradiol | 3β,22β | | | |
| 13 | 3β,22β-Dihydroxyolean-12-en-29-oic acid | 3β,22β | | 29 | |
| 14 | 2β-Hydroxyoleanolic acid | 2β,3β | | 28 | |
| 15 | Maslinic acid | 2α,3β | | 28 | |
| 16 | Echinocystic acid | 3β,16α | | 28 | |
| 17 | Hederagenin | 3β,23 | | 28 | |
| 18 | Phytolaccagenic acid | 3β,23 | | 28 | |
| 19 | Siaresinolic acid | 3β,19α | | 28 | |
| 20 | 21β-Hydroxyoleanolic acid (machaerinic acid) | 3β,21β | | 28 | |
| 21 | 29-Hydroxyoleanolic acid | 3β,29 | | 28 | |
| 22 | Azukisapogenol | 3β,24 | | 29 | |
| 23 | Soyasapogenol E | 3β,24 | 22 | | |
| 24 | Primulagenin D (28-dehydroprimulagenin) | 3β,16α | 28 | | |
| 25 | 3β,24-Dihydroxyolean-12,15-dien-28-oic acid | 3β,24 | | | 15-en |
| 26 | Soyasapogenol C | 3β,24 | | | 21-en |
| 27 | Glabrinic acid | 3β,26 | 11 | 30 | |
| 28 | Quillaic acid | 3β,16 | 23 | 28 | |
| 29 | 21β-Hydroxygypsogenin | 3β,21 | 23 | 28 | |
| 30 | Barringtogenic acid | 2α,3β | | 23,28 | |
| 31 | Medicagenic acid | 2β,3β | | 23,28 | |
| 32 | Dianic acid | 3β,29 | | 23,28 | |
| 33 | Soyasapogenol B | 3β,22β,24 | | | |
| 34 | 3β,22β,24-Trihydroxy-olean-12-en-29-oic acid | 3β,22β,24 | | 29 | |
| 35 | Primulagenin A | 3β,16α,28 | | | |
| 36 | 2β,3β,28-Trihydroxy-olean-12-en | 2β,3β,28 | | | |
| 37 | Priverogenin A | 3β,16α,22α | | 28 | |
| 38 | 16α-Hydroxy-hederagenin (caulophyllogenin) | 3β,16α,23 | | 28 | |
| 39 | 21β-Hydroxy-hederagenin | 3β,21β,23 | | 28 | |
| 40 | 3β,21β,22β-Trihydroxy-olean-12-en-29-oic acid | 3β,21β,22β | | 29 | |
| 41 | 23-Hydroxyimberbic acid | 1α,3β,23 | | 29 | |
| 42 | Arjunic acid | 2α,3β,19α | | 28 | |
| 43 | Arjunolic acid | 2α,3β,23 | | 28 | |
| 44 | Asterogenic acid | 2β,3β,16α | | 28 | |
| 45 | Bayogenin | 2β,3β,23 | | 28 | |
| 46 | 16-Hydroxy-medicagenic acid | 2β,3β,16 | | 23,28 | |
| 47 | Presenegenin | 2β,3β,27 | | 23,28 | |

TABLE 1-continued

Structures of commonly occurring olean-12-en aglycones

| No. | Olean-12-en aglycone | —OH | =O | —COOH | Other |
|---|---|---|---|---|---|
| 48 | Jaligonic acid | 2β,3β,23 | | 28,30 | |
| 49 | Phytolaccagenin | 2β,3β,23 | | 28 | 30-COOMe |
| 50 | Belleric acid | 2α,3β,23,24 | | | |
| 51 | Barringtogenol A | 2α,3β,23,28 | | | |
| 52 | Protobassic acid | 2β,3β,6β,23 | | 28 | |
| 53 | Platycogenic acid C | 2β,3β,16β,21β | | 28 | |
| 54 | Polygalacic acid | 2β,3β,16α,23 | | 28 | |
| 55 | Tomentosic acid | 2α,3β,19β,23 | | 28 | |
| 56 | Arjungenin | 2α,3β,19β,23 | | 28 | |
| 57 | Esculentagenic acid | 2β,3β,23,30 | | 28 | |
| 58 | 23-Hydroxylongispinogenin | 3β,16β,23,28 | | | |
| 59 | Cyclamiretin E | 3β,16α,28,30 | | | |
| 60 | Soyasapogenol A | 3β,21β,22β,24 | | | |
| 61 | Oxytrogenol | 3β,22β,24,29 | | | |
| 62 | 3α,21β,22α,28-Tetrahydroxyolean-12-en | 3α,21β,22α,28 | | | |
| 63 | 3β,23,27,29-Tetrahydroxyoleanolic acid | 3β,23,27,29 | | 28 | |
| 64 | Barringtogenol C | 3β,16α,21β,22α,28 | | | |
| 65 | Camelliagenin C | 3β,16α,22α,23,28 | | | |
| 66 | 16α-Hydroxyprotobassic acid | 2β,3β,6β,16α,23 | | 28 | |
| 67 | Platycodigenin | 2β,3β,16α,23,24 | | 28 | |
| 68 | Protoaescigenin | 3β,16α,21β,22α,24,28 | | | |
| 69 | Theasapogenol A | 3β,16α,21β,22α,23,28 | | | |
| 70 | R$_1$-Barrigenol | 3β,15α,16α,21β,22α,28 | | | |

TABLE 2

Triterpene aglycones (other than olean-12-en type). The skeletons are designated by capital letters A to I as indicated in FIG. 4.

| No. | Name | Skeleton | —OH | =O | —COOH | Other |
|---|---|---|---|---|---|---|
| 71 | Protoprimulagenin A | A | 3β,16α | | | |
| 72 | Cyclamiretin A | A | 3β,16α | 30 | | |
| 73 | Rotundiogenin A | A | 3β,16α | | | 11-en |
| 74 | Saikogenin E | A | 3β,16α | | | 11-en |
| 75 | Anagalligenone | A | 3β,23 | 16 | | |
| 76 | Saikogenin F | A | 3β,16β,23 | | | |
| 77 | Saikogenin G (anagalligenin B) | A | 3β,16α,23 | | | |
| 78 | Priverogenin B | A | 3β,16α,22α | | | |
| 79 | Anagalligenin A | A | 3β,16α,22α,28 | | | |
| 80 | α-Amyrin | B | 3β | | | 12-en |
| 81 | Ursolic acid | B | 3β | | 28 | 12-en |
| 82 | Quinovic acid | B | 3β | | 27,28 | 12-en |
| 83 | 3β-Hydroxyurs-12,20(30)-dien-27,28-dioic acid | B | 3β | | 27,28 | 12,20(30)-dien |
| 84 | Pomolic acid | B | 3β,19α | | 28 | 12-en |
| 85 | Ilexgenin B | B | 3β,19α | | 28 | 12-en (30S)30β |
| 86 | Ilexgenin A | B | 3β,19α | | 24,28 | 12-en |
| 87 | 21β-Hydroxyursolic acid | B | 3β,21β | | 28 | 12-en |
| 88 | 23-Hydroxyursolic acid | B | 3β,23 | | 28 | 12-en |
| 89 | 3β,23-Dihydroxy-taraxer-20-en-28-oic acid | B | 3β,23 | | 28 | 20-en |
| 90 | Rotundic acid | B | 3β,19α,23 | | 28 | 12-en |
| 91 | Rotungenic acid | B | 3β,19α,24 | | 28 | 12-en |
| 92 | Madasiatic acid | B | 2α,3β,6β | | 28 | 12-en |
| 93 | Asiatic acid | B | 2α,3β,23 | | 28 | 12-en |
| 94 | Euscaphic acid | B | 2α,3α,19α | | 28 | 12-en |
| 95 | Tormentic acid | B | 2α,3β,19α | | 28 | 12-en |
| 96 | 2β,3β,19α-Trihydroxyurs-12-en-23,28-dioic acid | B | 2α,3α,19α | | 23,28 | 12-en |

TABLE 2-continued

Triterpene aglycones (other than olean-12-en type). The skeletons are designated by capital letters A to I as indicated in FIG. 4.

| No. | Name | Skeleton | —OH | =O | —COOH | Other |
|---|---|---|---|---|---|---|
| 97 | 6β-Hydroxytormentic acid | B | 2α,3β,6β,19α | | 28 | 12-en |
| 98 | 7α-Hydroxytormentic acid | B | 2α,3β,7α,19α | | 28 | 12-en |
| 99 | 23-Hydroxytormentic acid | B | 2α,3β,19α,23 | | 28 | 12-en |
| 100 | 24-Hydroxytormentic acid | B | 2α,3β,19α,24 | | 28 | 12-en |
| 101 | 1α,3β,19α,23-Tetrahydroxyurs-12-en-28-oic acid | B | 1α,3β,19α,23 | | 28 | 12-en |
| 102 | Madecassic acid | B | 2α,3β,6β,23 | | 28 | 12-en |
| 103 | 6β,23-Dihydroxytormentic acid | B | 2α,3β,6β,19α,23 | | 28 | 12-en |
| 104 | Lupeol | C | 3β | | | 20(29)-en |
| 105 | Betulin | C | 3β,28 | | | 20(29)-en |
| 106 | Betulinic acid | C | 3β | | 28 | 20(29)-en |
| 107 | 3-epi-Betulinic acid | C | 3α | | 28 | 20(29)-en |
| 108 | 3β,23-Dihydroxylup-20(29)-en-oic acid | C | 3β,23 | | 28 | 20(29)-en |
| 109 | 3α-Hydroxylup-20(29)-en-23,28-dioic acid | C | 3α | | 23,28 | 20(29)-en |
| 110 | 3α,11α-Dihydroxylup-20(29)-en-23,28-dioic acid | C | 3α,11α | | 23,28 | 20(29)-en |
| 111 | Cylicodiscic acid | C | 3β,27α | | 28 | 20(29)-en |
| 112 | Mollugogenol B | D | 3β,6α | | | 15,17(21)-dien |
| 113 | (20S)-Protopanaxadiol | E | 3β,12β,20S | | | 24-en |
| 114 | (20S)-Protopanaxatriol | E | 3β,6α,12β,20S | | | 24-en |
| 115 | Bacogenin A₁ | E | 3β,19,20 | 16 | | 24-en |
| 116 | Seychellogenin | F | 3β | | | 7,9(11)-dien 18,20-lactone |
| 117 | Mollic acid | G | 1α,3β | | 28 | |
| 118 | 3β,21,26-Trihydroxy-9,19-cyclolanost-24-en | G | 3β,21,26 | | | 24-en |
| 119 | Thalicogenin | G | 3β,16β,22,28 | | | 24-en |
| 120 | 3β,16β,24,25-Tetrahydroxy-9,19-cyclolanostane | G | 3β,16β,24,25 | | | |
| 121 | 3β,6α,16β,24,25-Pentahydroxy-9,19-cyclolanostane | G | 3β,6α,16β,24,25 | | | |
| 122 | Cycloastragenol (astramembrangenin, cyclosiversigenin) | H | 3β,6α,16β,25 | | | |
| 123 | 3β-Hydroxy-9,19-cyclolanost-24(28)-en | I | 3β | | | 24(28)-en |
| 124 | Jessic acid | I | 1α,3β | 23 | 29 | 24(28)-en |

The complexes according to the present invention have molecular weights ranging from for example about 400 daltons to more than 2,000 daltons. Further examples are from about 500 daltons, such as from about 600 daltons, for example from about 700 daltons, such as from about 800 daltons, such as from about 900 daltons, for example from about 1000 daltons, such as from about 1100 daltons, such as from about 1200 daltons, for example from about 1300 daltons, such as from about 1400 daltons, such as from about 1500 daltons, for example from about 1600 daltons, such as from about 1700 daltons, such as from about 1800 daltons, for example from about 1900 daltons, such as from about 2000 daltons, to preferably less than 4,000 daltons.

In one embodiment of the present invention, the saponin compound is acylated with one or more organic acids such as acetic acid, malonic acid, angelic acid and the like (see fx Massiot, G. & Lavaud, C., Stud. Nat. Prod. Chem. 15:187-224 (1995), incorporated herein by reference).

Saccharide Moieties of Saponins

Saponins according to the present invention, including the aglycone as illustrated in Table 1 and Table 2 herein above, have one or more linear or branched saccharide chains attached to the aglycone part via a glycosidic ether or ester bond.

According to the number of saccharide chains attached to the aglycone, the saponins can be monodesmosidic saponins (with a single saccharide chain), or bidesmosidic saponins (with two saccharide chains).

In the monodesmosidic saponins according to the invention, the saccharide chain is preferably attached by a glycosidic ether linkage at the C-3 of the aglycone. In addition to the C3 linked saccharide chain, bidesmosidic saponins have a second saccharide chain bound at C-28 (triterpene saponins) or at C-26 (steroid saponins) by an ester linkage. Because of the typical lability of esters, bidesmosidic saponins are readily converted into their monodesmosidic forms by mild hydrolysis (Hostettmann, K., et al., Methods Plant Biochem. 7:435-471 (1991)).

Bidesmosidic saponins according to the invention preferably have two sugar chains, one of which may be attached through an ether linkage at C-3, and one attached through an ester linkage (acyl glycoside) at C-28 (triterpene saponins), or an ether linkage at C-26 (furostanol saponins).

Bidesmosidic saponins are easily converted into monodesmosidic saponins by, for example, hydrolysis of the esterified sugar at C-28 in triterpene saponins, and they differ from monodesmosidic saponins with respect to some properties and activities. Also, when one sugar chain is attached at C-3, a second sugar group may be esterified to the carboxyl group at C-17 of the aglycone. Furthermore, some dammarane glycosides and lanostane glycosides may have a second or even a third glycosidically bound sugar chain.

Tridesmosidic saponins according to the invention have three sugar chains. Hydrolysis of the esterified sugars result in conversion into bidesmosidic saponins and/or monodesmosidic saponins. An example of one tridesmosidic triterpene is a 9,19-cyclolanostane (cycloartane) substituted glycosidically at positions C-3, C-6 and C-25. An example of a tridesmosidic olean-12-en saponin is quinoside A, in which sugars are attached at positions C-3, C-23 and C-28 of hederagenin (Meyer et al. 1990). Also, a tridesmoside of 16α-hydroxymedicagenic acid (zahnic acid) has been found in the aerial parts of alfalfa (*Medicago saliva*, Leguminosae) (Oleszek et al. 1992).

The saccharide moiety of saponins according to the invention may be linear or branched, with about 11 being the highest number of monosaccharide units yet found in a saponin (Clematoside C from *Clematis manshurica* (Ranunculaceae); Khorlin et al. 1965). However, the present invention is not limited to saccharide moieties containing 11 or less monosaccharide units. Saponins according to the present invention may comprise less than 10 saccardde moieties, such as less than 9 saccharide moieties, for example less than 8 saccharide moieties, such as less than 7 sacoharide moieties, for example less than 6 saccharide moieties, such as less than 5 saccharide moieties, for example less than 4 saccharide moieties, such as less than 3 saccharide moieties, for example less than 2 saccharide moieties, such as one saccharide moiety.

In fact, most saponins so far isolated tend to have relatively short (and often unbranched) sugar chains, containing from about 2 to about 5 monosaccharide residues. Kochetkov and Khorlin (1966) have introduced the term oligoside for glycosides containing more than 3 to 4 monosaccharides.

Accordingly, there are also provided saponins according to the present invention comprising one or more sugar chains, for example two or three sugar chains, wherein one or more sugar chains comprises for example from about 2 to about 11 monosaccharide residues, such as from about 2 to about 10 monosaccharides, for example from about 2 to about 11 monosaccharide residues, such as from about 2 to about 10 monosaccharides, for example from about 2 to about 9 monosaccharide residues, such as from about 2 to about 8 monosaccharides, for example from about 2 to about 7 monosaccharide residues, such as from about 2 to about 6 monosaccharides, for example from about 2 to about 5 monosaccharide residues, such as from about 2 to about 4 monosaccharides, for example from about 2 to about 3 monosaccharide residues.

In another embodiment the present invention provides saponins comprising one or more sugar chains, for example two or three sugar chains, wherein one or more sugar chains comprises more than 3 monosaccharides, such as more than 4 monosaccharides, for example more than 5 monosaccharides, such as more than 6 monosaccharides, for example more than 7 monosaccharides, such as more than 8 monosacchardes, for example more than 9 monosaccharides, and preferably less than 11 monosaccharide residues.

Oligosides as used herein refer to saponin glycosides containing 4 or more monosaccharides, such as more than 5 monosaccharides, for example more than 6 monosaccharides, and independently thereof preferably less than 12 monosaccharides, such as less than 11 monosaccharides, for example less than 10 monosaccharides, such as less than 9 monosaccharides, for example less than 8 monosaccharides.

However, saponins according to the present invention may also comprise one or more sugar chains, for example two or three sugar chains, wherein one or more of said sugar chains comprises more than 11 monosaccharides, for example about 15 monosaccharides, such as about 20 monosaccharides, for example more than about 25 monosaccharides, such as more than about 40 monosaccharides.

Preferred monosaccharide residues of saponin glycosides according to the present invention are: D-glucose (Glc), D-galactose (Gal), D-glucuronic acid (GlcA), D-galacturonic acid (GalA), L-rhamnose (Rha), L-arabinose (Ara), D-xylose (Xyl) and D-fucose (Fuc). Also preferred are D-apiose (Api), D-ribose (Rib), and D-allose (All). Furthermore, saponins obtained from marine organisms often contain D-quinovose (Qui) (sometimes written as D-chinovose). All the above abbreviations are used in accordance with IUPAC recommendations (Pure Appl. Chem. (1982). vol. 54, p.1517-1522)

In addition to the above-mentioned monosaccharides the present invention also pertains to unusual monosaccharides such as uronic acids that are known to occur in some triterpene glycosides. Another example of unusual monosaccharides are monosaccharides comprising an amino saccharide and/or an acylated saccharide.

Among the preferred monosaccharides directly attached to the saponin aglycone are glucose, arabinose, glucuronic acid and xylose. Such monosaccharides thus forms the link between the saccharide part and the aglycone part of the saponin.

Another group of saccharides according to the invention are saccharides comprising acylated sugar moieties, as well as saccharides comprising methylated and/or sulphated sugar moieties.

In accordance with generally agreed nomenclature, the configurations of the interglycosidic linkages are given herein by α and A, respectively, and the monosaccharides making up the sugar part of saponins according to the invention may adopt a pyranose (p) and/or a furanose (f) form.

Quillaja Saponins

As used herein, saponins from the bark of the *Quillaja saponaria* Molina tree are termed Quillaja saponins. Quillaja saponins represent one group of particularly preferred saponins according to the present invention. Quillaja saponins are either first saponins or second saponins, wherein the latter group of Quillaja saponins are capable of forming and interaction with a genetic determinant.

Quillaja saponins are found as a mixture of about twenty structurally closely related triterpenoid glycosides with minimal differences between them (Higuchi, R. et al., Phytochemistry 26:229 (1987); ibid., 26:2357 (1987); ibid., 27:1169 (1988); Kensil et al., U.S. Pat. No. 5,057,540 (1991); Kensil et al., Vaccines 92:35 (1992)). Quillaja saponins are chemically and immunologically well-characterized (see fx Dalsgaard, K. Arch. Gesamte Virusforsch. 44:243 (1974), Dalsgaard, K., Acta Vet. Scand. 19 (Suppl. 69):1 (1978); Higuchi, R. et al., Phytochemistry 26:229 (1987); ibid. 26:2357 (1987); ibid. 27:1168 (1988); Kensil, C. et al., J. Immunol. 146:431 (1991); Kensil et al., U.S. Pat. No. 5,057,540 (1991); Kensil et al., Vaccines 92:35 (1992); Bomford, R. et al., Vaccine 10:572 (1992); Kensil, C. et al., U.S. Pat. No. 5,273,965 (1993); ); Kensil, C. et al., U.S. Pat. No. 5,443,829 (1995); ); Kensil, C. et al., U.S. Pat. No. 5,583,112 (1996); and Kensil, C. etal., U.S. Pat No. 5,650,398 (1997); all of which are incorporated herein by reference).

Quillaja saponins belong to a family of closely related O-acylated triterpene glycoside structures. They have an aglycone triterpene (quillaic acid), with branched saccharide chains attached to positions 3 and 23, and an aldehyde group in position 23. A unique characteristic of Quillajasaponins pertaining to the invention is the presence of certain acyloil acyl moieties linked at the C-3 hydroxy group of a fucopyranose bound by an ester bond to position 28 of quillaic acid. Preferred acyl moieties are 3,5-dihydroxy-6-methyloctanoic acid, 3,5-dihydroxy6-methyloctanoic acid, 5-O-α-L-rhamno-pyranosyl-(1→2)-α-L-arabino-furanoside, and 5-O-α-L-arabino-furanoside.

Quillaja saponins according to the present invention may be obtained from quillaja plant species including *Quillaja saponaria* Molina and others either as a crude extract, or as an extract which have been purified by various open column techniques (i.e. chromatography by means of e.g. ion exchange-, size exclusion-, hydrophobic-, affinity-, and otherwise). Such purified or semi-purified saponins are generally referred to in the art as "Quil A", or "Quadri A", as described by WO 95109179, which is incorporated herein by reference.

The saponins may also be purified by high resolution hydrophobic interaction techniques, such as e.g. HPLC, and this form of purification generates fractions known in the art as e.g. "Quadri 1", "Quadri2", and the like (see e.g. WO 95/09179, as well as Kamstrup et al. Vaccine (2000), vol 18, no. 21, 2244-2249, incorporated herein by reference).

Particularly preferred are saponin extracts from *Quillaja saponaria* Molina, primarily the DQ-extract produced according to K. Dalsgaard: Saponin Adjuvants, Bull. Off Int Epiz. 77 (7-8), 1289-1295 (1972), and Quil A which is produced according to K. Dalsgaard: Saponin Adjuvants III, Archiv fur die Gesamte Virusforschung 44, 243-254 (1974). Also mixtures of such glycosides pertain to the present invention.

The amount of glycoside added should be at least 1-3 times their critical micelle formation concentration (CMC), preferably at least 5, especially at least 7-12 times. Preferably Quil A is used, which has a critical micelle formation concentration of 0.03% by weight. The amount of Quil A should then be at least 0.02% by weight, especially 0.05-0.5% by weight, preferably 0.2% by weight.

Further fractions of saponins according to the present invention are described in detail herein below. According to U.S. Pat. No. 5,057,540, the contents of which are incorporated herein by reference, saponins can be purified from an aqueous extract of the bark of the South American tree, *Quillaja saponaria* Molina. At least 22 peaks with saponin activity were separable.

The predominant purified Quillaja saponins are QA-7, QA-17, QA-18, and QA-21. These saponins have been purified by high pressure liquid chromatography (HPLC) and low pressure silica chromatography. QA-21 can be further purified using hydrophilic interaction chromatography (HILIC) and resolved into two peaks, QA-21-V1 and QA-21-V2, that are different compounds.

Thus, "QA-21" designates the mixture of components QA-21-V1 and QA-21-V2 that appear as a single peak on reversed-phase HPLC on VYDAC C4 (5 μm particle size, 330 Ångstrøm pore, 4.6 mm ID×25 cm L) in 40 mM acetic acid in methanol/water (58/42, v/v). The component fractions are referred to specifically as QA-21V1 and QA-21-V2 when describing experiments or results performed on the further purified components.

In order to purify saponins from *Quillaja saponaria* Molina bark, aqueous extracts of the *Quillaja saponaria* Molina bark are dialyzed against water. The dialyzed extract is lyophilized to dryness, extracted with methanol and the methanol-soluble extract is further fractionated by silica gel chromatography and by reversed-phase high pressure liquid chromatography (RP-HPLC).

TABLE 3

Reversed-phase HPLC peaks designating individual saponins and their corresponding retention times.

| Peak | Retention Time (minutes) |
|---|---|
| QA-1 | solvent front |
| QA-2 | 4.6 |
| QA-3 | 5.6 |
| QA-4 | 6.4 |
| QA-5 | 7.2 |
| QA-6 | 9.2 |
| QA-7 | 9.6 |
| QA-8 | 10.6 |
| QA-9 | 13.0 |
| QA-10 | 17.2 |
| QA-11 | 19.0 |
| QA-12 | 21.2 |
| QA-13 | 22.6 |
| QA-14 | 24.0 |
| QA-15 | 25.6 |
| QA-16 | 28.6 |
| QA-17 | 35.2 |
| QA-18 | 38.2 |
| QA-19 | 43.6 |
| QA-20 | 47.6 |
| QA-21 | 51.6 |
| QA-22 | 61.0 |

As shown above, individual saponins can be separated by reversed-phase HPLC- At least 22 peaks (designated QA-1 to QA-22) are separable. Individual components are identified by retention time on a VYDAC C4 HPLC column as follows in Table 3 herein above. Each peak corresponds to a carbohydrate peak that exhibits only a single band on reversed-phase thin layer chromatography.

The substantially pure QA-7 saponin is characterized as having immune adjuvant activity, containing about 35% carbohydrate (as assayed by anthrone) per dry weight, having a UV absorption maximum of 205-210 nm, a retention time of approximately 9-10 minutes on RP-HPLC on a VYDAC C4 column having 5 μm particle size, 330 Ångstrøm pore, 4.6 mm ID×25 cm L in a solvent of 40 mM acetic acid in methanol-water (58/42; v/v) at a flow rate of 1 mL/min, eluting with 52-53% methanol from a VYDAC C4 column having 5 μm particle size, 330 Ångstrøm pore, 10 mm ID×25 cm L in a solvent of 40 mM acetic acid with gradient elution from 50 to 80% methanol, having a critical micellar concentration of 0.06% (w/v) in water and 0.07% (w/v) in phosphate buffered saline, causing no detectable hemolysis of sheep red blood cells at concentrations of 200 μg/mL or less, and containing the monosaccharide residues terminal rhamnose, terminal xylose, terminal glucose, terminal galactose, 3-xylose, 3,4-rhamnose, 2,3-fucose, 2,3-glucuronic acid, and apiose (linkage not determined).

The substantially pure QA-17 saponin is characterized as having adjuvant activity, containing about 29% carbohydrate (as assayed by anthrone) per dry weight, having a UV absorption maximum of 205-210 nm, a retention time of approximately 35 minutes on RP-HPLC on a VYDAC C4 column having 5 μm particle size, 330 Ångstrøm pore, 4.6 mm ID×25 cm L in a solvent of 40 mM acetic acid in methanol-water (58/42; v/v) at a flow rate of 1 mL/min, eluting with 63-64% methanol from a VYDAC C4 column having 5 μm particle size, 330 Ångstrøm pore, 10 mm ID×25 cm L in a solvent of 40 mM acetic acid with gradient elution from 50 to 80% methanol, having a critical micellar concentration of 0.06% (w/v) in water and 0.03% (w/v) in phosphate buffered saline, causing hemolysis of sheep red blood cells at 25 μg/mL or greater, and containing the monosaccharide residues terminal rhamnose, terminal xylose, 2-fucose, 3-xylose, 3,4-rhamnose, 2,3-glucuronic acid, terminal glucose, 2-arabinose, terminal galactose and apiose (linkage not determined).

The substantially pure QA-18 saponin is characterized as having immune adjuvant activity, containing about 25-26% carbohydrate (as assayed by anthrone) per dry weight, having a UV absorption maximum of 205-210 nm, a retention time of approximately 38 minutes on RP-HPLC on a VYDAC C4 column having 5 μm particle size, 330 Ångstrøm pore, 4.6 mm ID×25 cm L in a solvent of 40 mM acetic acid in methanol/water (58/42; v/v) at a flow rate of 1 mL/min, eluting with 64-45% methanol from a VYDAC C4 column having 5 μm particle size, 330 Ångstrøm pore, 10 mm ID×25 cm L in a solvent of 40 mM acetic acid with gradient elution from 50 to 80% methanol, having a critical micellar concentration of 0.04% (w/v) in water and 0.02% (w/v) in phosphate buffered saline, causing hemolysis of sheep red blood cells at concentrations of 25 μg/mL or greater, and containing the monosaccharides terminal arabinose, terminal apiose, terminal xylose, terminal glucose, terminal galactose, 2-fucose, 3-xylose, 3,4-rhamnose, and 2,3-glucuronic acid.

The substantially pure QA-21 saponin is characterized as having immune adjuvant activity, containing about 22% carbohydrate (as assayed by anthrone) per dry weight, having a UV absorption maximum of 205-210 nm, a retention time of approximately 51 minutes on RP-HPLC on a WDAC C4 column having 5 μm particle size, 330 Ångstrøm pore, 4.6 mm ID×25 cm L in a solvent of 40 mM acetic acid in methanol/water (58/42; v/v) at a flow rate of 1 mL/min, eluting with 69 to 70% methanol from a VYDAC C4 column having 5 μm particle size, 330 Ångstrøm pore, 10 mm ID×25 cm L in a solvent of 40 mM acetic acid with gradient elution from 50 to 80% methanol, with a critical micellar concentration of about 0.03% (w/v) in water and 0.02% (w/v) in phosphate buffered saline, and causing hemolysis of sheep red blood cells at concentrations of 26 μg/mL or greater. The component fractions, substantially pure QA-21-V1 and QA-21-V2 saponins, have the same molecular weight and identical spectra by fast atom bombardment—mass spectroscopy (FAB-MS). They differ only in that QA-21-V1 has a terminal apiose that is xylose in QA-21-V2 (which therefore has two terminal xyloses and no apiose). The two components additionally contain the monosaccharides terminal arabinose, terminal apiose, terminal xylose, 4-rhamnose, terminal galactose, 2-fucose, 3-xylose, and 2,3glucuronic acid.

The alkaline hydrolysis products can be prepared as follows. Treatment of OA-18 by brief alkaline hydrolysis yielded one major carbohydrate-containing alkaline hydrolysis product (designated QA-18-H). Purified QA-18-H was prepared from CA-18 and isolated in the following manner:

One mL QA-18 (5 mg/ml) was incubated with 25 μl 1N NaOH for 15 minutes at room temperature. The reaction was stopped with the addition of 100 μl 1N acetic acid. Using these hydrolysis conditions, QA-18 was completely converted to a major hydrolysis product (QA-18-H) eluting in a peak with retention time of 8.0 min compared to 66.8 min for unhydrolyzed QA-18, indicating the increased hydrophilicity of QA-18-H. (Chromatography on VYDAC C4 (4.6 mm ID×25 cm L) in 0.1% trifluoroacetic acid in 55/45 methanol/water (v/v) and eluted in a gradient to 64/36 methanol/water (v/v) over 180 minutes, flow rate of 1 mL/minute). The peak containing pure OA-18-H (retention time 8.0 min) was pooled for further characterization. The hydrolysis product of QA-21, designated QA-21-H, was prepared and purified in the same manner. QA-21-H had a retention time of 9.3 minutes compared to 80.4 minutes for its unhydrolyzed precursor, QA-21. The hydrolysis products were shown by retention time on HPLC and by reversed-phase thin layer chromatography to be identical to major hydrolysis products generated using the method of Higuchi et al., Phytochemistry 26:229 (1987) using mild alkaline hydrolysis in $NH_4HCO_3$ (Table 4).

TABLE 4

| Retention Time of Major Alkaline Hydrolysis Products | |
|---|---|
| QA-17-H | 8.0[a] |
| QA-18-H | 8.0[a] |
|  | 8.2[b] |
| QA-21-H | 9.3[a] |
|  | 9.5[b] |
| Hydrolyzed - "Quil-A" | 8.2[a], 9.3[a] |

[a]Cambridge Biotech hydrolysis conditions: 5 mg/ml saponin, pH 13, reaction time = 15 minutes at room temperature.
[b]Higuchi et al. hydrolysis conditions: 5 mg/ml saponin, 6% $NH_4HCO_3$, methanol/$H_2O$ (1/1, v/v), reaction time = 60 minutes at 100° C.

HPLC Conditions:
VYDAC C4, 5 mm particle size, 330 Ångstrøm pore size, 0.46×25 cm
Solvent A=0.1% trifluoroacetic acid in water
Solvent B—0.1% trifluoroacetic acid in methanol
Gradient=55-64% B/180 minutes
Flow rate—1 ml/min In addition, these products, QA-18-H and QA-21-H, were shown to be the major breakdown products from hydrolysis of "Quil-A", a crude saponin mixture containing QA-7, QA-17, QA-18, and QA-21 as well as other saponins, indicating that the hydrolysis products QA-21-H and QA-18-H are the same hydrolysis products isolated by Higuchi et al., supra, for structural characterization.

Even further preferred saponins according to the present invention are those described e.g. in EP 0436 620 B1, incorporated herein by reference, including fractions termed QHA, QHB, QHC, or similar compositions of Quillaja saponins.

Acylated quillaja saponins appear to be exceptional since their monodesmosidic forms are significantly less effective hemolytic agents than their acylated and non-acylated bidesmosidic forms (Pillion, D. J., et al., J. Pharm. Sci., 84:1276-1279 (1998)).

In addition to Quillaja saponins, saponins originating from Gypsophila species and Saponaria species, including *Saponaria officinalis*, are also useful in accordance with the present invention, particularly Gypsophila species and Saponaria species which have been shown to include "quillajic acid" as the aglycon component of the saponin glycoside. Furthermore, such saponins from Gypsophila species and Saponaria species preferably comprise triterpene aglycones with an aldehyde group linked or attached to position 4, branched oligosaccharides linked by an ester bond in position 28, and a 3-O-glucuronic acid (3-O-glcA) that in Quillaja and Gypsophila is linked to branched oligosaccharides. Saponins from *Q. saponaria* and *S. jenisseenis* include acyl moieties, whereas saponin from Gypsophila, Saponaria, and Acanthophyllum do not include acyl moieties. Each of these non-acylated or deacylated saponins is useful in the present invention.

Further desirable triterpene saponins are the bidesmosidic saponin, squarroside A, isolated from *Acanthophyllum squarrosum*; the saponin lucyoside P; and two acylated saponins isolated from *Silene jenisseensis* Willd. Following is a brief description of these compounds.

Squarroside A is abidesmosidic saponin that contains two oligosaccharide chains linked to C-3 and C-28 of its aglycone gypsogenin. Similar to the gypsophila saponin, it has an aldehyde group linked to C-4 of the aglycone, and a glucuronic acid residue at C-3. In addition, it contains an acetylated fucose residue at C-28. It has been shown that squarroside A has immunomodulating activity as measured by an in vitro lymphoproliferative test. These apparently nonspecific immunomodulating effects were dose-dependent: a suppressive effect at concentrations in the µg range and a stimulant effect in the pg range.

Lucyoside P is a bidesmosidic saponin that has carbohydrate residue linked to C-3 and C-28 of its aglycone quillaic acid, and an aldehyde group at C4. Lucyoside P has a glucuronic acid residue at C-3.

Two acylated saponins have been isolated from the Caryophyllacea *Silene jenisseensis*. These saponins have carbohydrates linked to C-3 and C28 of their agylcone quillaic acid. The carbohydrate residues linked to C-3 and C-28 are glucuronic acid and fucose, respectively. The fucose residue is acylated with a p-methoxy-cinnamoyl group to yield trans- and cis-p-methoxycinnamoyl tritepene glycosides.

Although the saponins mentioned herein immediately above have an aldehyde group, they apparently have no immunostimulating activity or a significantly reduced immunostimulauing activity, as detected by an in vitro chemiluminescence granulocyte assay.

Yet further examples of useful saponins according to the present invention pertain to triterpensaponins such as the polar acidic bisdesmosides extracted from e.g. Chikosetsusaponin IV, Calendula-Glycoside C, Chikusetsusaponin V, Achyranthes-Saponin B, Calendula-Glycoside A, Araloside B, Araloside C, Putranjia-Saponin III, Bersamasaponoside, Putranjia-Saponin IV, Trichoside A, Trichoside B, Saponaside A, Trichoside C, Gypsoside, Nutanoside, Dianthoside C, Saponaside D, preferably aescine from *Aesculus hippocastanum* (T. Patt and W. Winkler: Das therapeutisch wirksame Prinzip der Rosskatanie (*Aesculus hippocastanum*), Arzneimittelforschung 10(4), 273-275 (1960) or sapoalbin from *Gypsophilla struthium* (R. Vochten, P. Joos and R. Ruyssen; Physicochemical properties of sapoalbin and their relation to the foam stability, J. Pharm. Belg. 42, 213-226 (1968).

A number of so-called "modified saponins" obtained from *Quillaja saponaria* have been disclosed by Kensil et al. in e.g. U.S. Pat. No. 5,273,965; U.S. Pat. No. 5,443,829; and U.S. Pat. No. 5,650398, all of which are incorporated herein by reference. The modified Quillaja saponins typically comprise a methylenealcohol group or a methyleneamino group instead of the naturally occurring triterpene aldehyde group. The modified saponins may be further modified with respect to their saccharide moieties.

One interesting saponin composition according to the present invention is the so-called "7-0-3" composition comprising 7/10 (70%) QH-A, 0/10 (0%) QH-B, and 3/10 (30%) QH-C. respectively of each fraction, as described by Ronnberg et al. in Vaccine (1995), vol. 13, no. 14, p. 1375-1382, and in Vaccine (1997), vol. 15, no. 17-18, p. 1820-1826.

The ratio between the first saponin and the second saponin in complexes in which both are present are preferably from less than 1000:1 to preferably more than 1:1000. Preferred ratios are about 100:1, for example about 80:1, such as about 60;1, for example about 50;1, such as about 40:1, for example about 30:1, such as about 25:1, for example about 20:1, such as about 18:1, for example about 16:1, such as about 14:1, for example about 12;1, such as about 10:1, for example about 9:1, such as about 8:1, for example about 7:1, such as about 6:1, for example about 5:1, such as about 4:1, for example about 3:1, such as about 2:1, for example about 1.9:1, such as about 1.8:1, for example about 1.7:1, such as about 1.6:1, for example about 1.5:1, such as about 1.4:1, for example about 1.3:1, such as about 1.2:1, for example about 1.1:1, such as about 1:1, for example about 1:1.1, such as about 1:1.2, for example about 1:1.3, such as about 1:1.4, for example about 1:1.5, such as about 1:2, for example about 1:3, such as about 1:4, for example about 1:5, such as about 1:10, for example about 1:20, such as about 1:40, for example about 1:60, such as about 1:80, for example about 1:100.

Sterols and Steroids

Useful sterols are in this context those who bind to saponins forming part of the complexes according to the invention. Preferred sterols are cholesterols and precursors and derivatives of thereof, as for example, phytosterols, erg. lanosterol, lumisterol, stigmasterol, sitosterol, mycosterols, ergosterol, and thiocholesterol, the last of which can be used for binding a medicament by means of the thiol moiety. Nordihydro-epi-andosterol is a further preferred sterol according to the invention.

Apart from sterols, the present invention also pertains to complexes wherein at least one first and/or second sterol is substituted partly or wholly by a steroid. In one embodiment, the complexes according to the invention comprise a steroid compound instead of a sterol compound. Definitions and technical terms used herein to charcterise first and second sterols apply mutatis mutantis to first and second steroids.

Steroids according to the invention are exemplified herein below in more detail. As the sterols according to the present invention comprise the characteristic skeleton structure of a steroid, the description of steroids is also a description of the skeleton of the sterols according to the present invention, one of which is cholesterol having CAS (Chemical Abstract) accession no. 57-88-5, or cationic derivatives thereof, in particular cationic derivatives obtained by linking a cationic moiety or cationic reactive group to an OH-group, including an OH-group located at position 3 of the steroid skeleton, including the OH-group of cholesterol located at position 3 (C3, or 3-OH).

All steroids are related to a characteristic molecular structure composed of 17 carbon atoms arranged in four rings conventionally denoted by the letters A, B, C, and D and bonded to 28 hydrogen atoms.

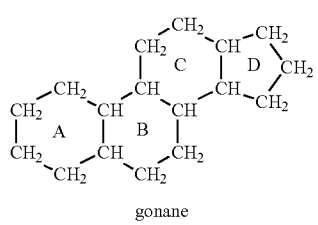

(1)

gonane

This parent structure (1), named gonane and often referred to as the steroid nucleus, may be modified in a practically unlimited number of ways by removal, replacement, or addition of a few atoms at a time; hundreds of steroids have been isolated from plants and animals, and thousands more have been prepared by chemical treatment of natural steroids or by synthesis from simpler compounds The steroid nucleus is a three-dimensional structure, and atoms or groups are attached to it by spatially directed bonds. Although many stereoisomers of this nucleus are possible (and may be synthesized), the saturated nuclear structures of most classes of natural steroids are alike, except at the junction of rings A and B. Simplified three-dimensional diagrams may be used to illustrate stereochemical details. For example, androstane common to a number of natural and synthetic steroids, exists in two forms (2 and 3), in which the A/B ring fusions are called cis and trans, respectively.

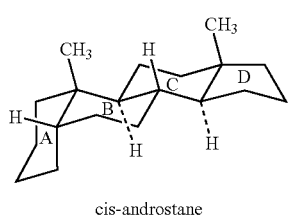

(2)

cis-androstane

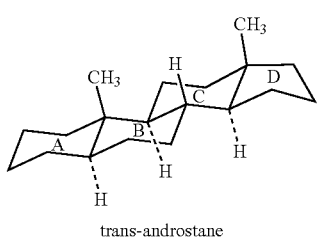

(3)

trans-androstane

In the cis isomer, bonds to the methyl group, CH$_3$, and to the hydrogen atom. H, both project upward from the general plane defined by the rest of the molecule, whereas in the trans isomer the methyl group projects up and the hydrogen projects down. Usually, however, steroid structures are represented as plane projection diagrams such as 4 and 5, which correspond to 2 and 3, respectively.

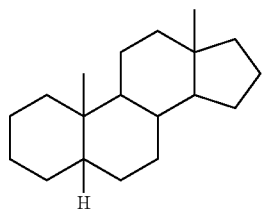

(4)

(5β)

cis-androstane

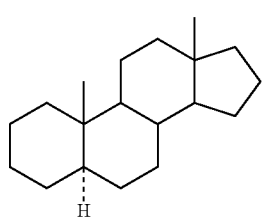

(5)

(5α)

trans-androstane

The stereochemistry of rings A and B must be specified by showing the orientation of the hydrogen atom attached at C5 (that is, carbon atom number 5; steroid numbering is explained below) as either above the plane of the diagram (designated β) or below it (α). The α-, β-symbolism is used in a similar manner to indicate the orientation of any substituent group that is attached to a saturated (fully substituted) carbon within the steroid ring system. Groups attached to unsaturated carbons lie in the same plane as the adjacent carbons of the ring system (as in ethylene), and no orientation need be specified. When the orientation of a substituent is unknown, it is assigned the symbol ξ. Bonding of β-attached substituents is shown diagrammatically as in 4 by a full line, that of α-substituents by a broken line, as in 5, and that of ξ-substituents by a wavy line.

Each carbon atom of a steroid molecule is numbered, and the number is reserved to a particular position in the hypothetical parent skeletal structure (6) whether this position is occupied by a carbon atom or not.

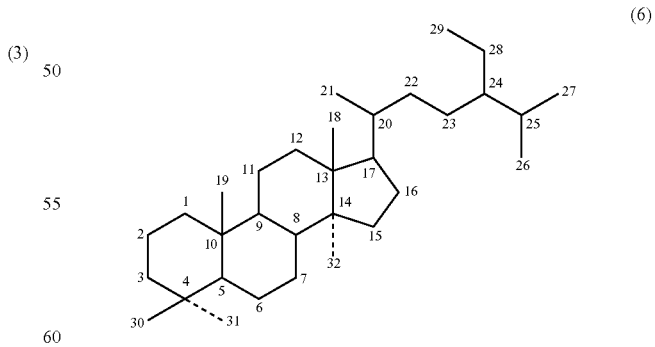

(6)

Steroids are named by modification of the names of skeletal root structures according to systematic rules agreed upon by the International Union of Pure and Applied Chemistry. By attaching prefixes and suffixes to the name of the appropriate root structure, the character of substituent groups or other structural modification is indicated. The prefixes and suffixes include numbers, called locants, indicative of the position in the carbon skeleton at which the modification occurs, and, where necessary, the orientation of a substituent is shown as α- or β-. The carbon atom at position 3, for example, is referred to as C3; a hydroxyl group attached to C3 is referred to as a 3-OH group or, more specifically, as a 3α-OH or 3β-OH group. In addition to differences in details of the steroid nucleus, the various classes of steroids are distinguished by variations in the size and structure of an atomic group (the side chain) attached at position 17. The derivations of the names of the more common root structures from those of naturally occurring compounds or classes of compounds for which they are most typical are known to the skilled artisan. For unambiguous use of such names, the orientation (α or β) of hydrogen at C5 must be specified. If no other modification is indicated, the nucleus is assumed to be as shown in (2) and (3), except in the cardanolides and bufanolides: compounds of these types characteristically possess the 5β,14β configurations, which, however, are specified.

Preferred second sterols are cationic sterols and sterols comprising at least one positively charged group at pH=7.0. Preferred sterols comprise or essentially consist of 3β-[N-(Dimethylaminoethane)-carbamoyl]cholesterol (DC-cholesterol) and/or N-(trimethylammonioethane)-carbamoylcholesterol (TC-cholesterol). Further preferred second sterols are described in FIG. 5.

It will be understood that the second sterols comprise cationic sterols, including cationic cholesterols, wherein the OH-group (located at position 3 in cholesterol) is substituted for a positively charged group, or a group comprising at least one positive charge at pH=7.0.

The ratio between the first sterol and the second sterol in complexes in which both are present are preferably from less than 1000:1 to preferably more than 1:1000. Preferred ratios are about 100:1, for example about 80:1, such as about 60:1, for example about 50:1, such as about 40:1, for example about 30:1, such as about 25:1, for example about 20:1, such as about 18:1, for example about 16:1, such as about 14:1, for example about 12:1, such as about 10:1, for example about 9:1, such as about 8:1, for example about 7:1, such as about 6:1, for example about 5:1, such as about 4:1, for example about 3:1, such as about 2:1, for example about 1.9:1, such as about 1.8:1, for example about 1.7:1, such as about 1.6:1, for example about 1.5:1, such as about 1.4:1, for example about 1.3:1, such as about 1.2:1, for example about 1.1:1, such as about 1:1, for example about 1:1.1, such as about 1:1.2, for example about 1:1.3, such as about 1:1.4, for example about 1:1.5, such as about 1:2, for example about 1:3, such as about 1:4, for example about 1:5, such as about 1:10, for example about 1:20, such as about 1:40, for example about 1:60, such as about 1:80, for example about 1:100.

Linker Groups

The deacylsaponins and non-acylsaponins may be directly linked to a lipophilic moiety or may be linked via a linking group. By the term "linking group" is intended one or more bifunctional molecules that can be used to covalently couple the desacylsaponins, non-acylated saponins or mixtures thereof to the lipophilic molecule.

The linker group in one embodiment covalently attaches to the carboxylic acid group of the 3-O-glucuronic acid moiety on the triterpene core structure, and to a suitable functional group present on a lipophilic moiety.

The saponins of the present invention may be directly linked to a lipophilic moiety, or a bioactive agent, including a genetic determinant, or they may be linked via a linking group. By the term "linker group" is intended one or more bifunctional molecules which can be used to covalently couple the saponin or saponin mixture to the bioactive agent including a genetic determinant. The linker group may be attached to any part of the saponin.

Typically, the saponins are linked to the lipophilic moiety, or the bioactive agent including a genetic determinant by the preparation of an active ester of glucuronic acid, a component of the saponins, followed by reaction of the active ester with a nucleophilic functional group on the bioactive agent including a genetic determinant.

Several lipophile-containing compounds, such as aliphatic amines and alcohols, fatty acids, polyethylene glycols and terpenes, can be added e.g. to the 3-O-glcA residue (3-glucuronic acid residue) of deacylsaponins, and to the 3-O-glcA residue of non-acylated saponins. The lipophile may be an aliphatic or cyclic structure that can be saturated or unsaturated. By way of example, fatty acids, terpenoids, aliphatic amines, aliphatic alcohols, aliphatic mercaptans, glycosyl-fatty acids, glycolipids, phospholipids and mono- and di-acylglycerols can be covalently attached to nonacylated saponins or desacylsaponins.

Attachment can be via a functional group on a lipophilic moiety that covalently reacts with either the acid moiety of the 3-glucuronic acid moiety, or an activated acid functionality at this position. Alternatively, a bifunctional linker can be employed to conjugate the lipophile to the 3-O-glcA residue of the first and/or second saponin.

Useful fatty acids include $C_8$-$C_{24}$ fatty acids, for example $C_7$-$C_{20}$ fatty acids, such as $C_7$-$C_{18}$ fatty acids. Examples of useful fatty acids include saturated fatty acids such as lauric, myristic, palmitic, stearic, arachidic, behenic, and lignoceric acids: and unsaturated fatty acids, such as palmitoleic, oleic, linoleic, linolenic and arachidonic acids.

Useful aliphatic amines, aliphatic alcohols and aliphatic mercaptans include amines and alcohols and mercaptans (R—SH) having a straight-chained or branched, saturated or unsaturated aliphatic group having about 6 to about 24 carbon atoms, for example 6 to 20 carbon atoms, such as 6 to 16 carbon atoms, for example 8 to 12 carbon atoms. Examples of useful aliphatic amines include octylamine, nonylamine, decylamine, dodecylamine, hexadecylamine, sphingosine and phytosphingosine. Examples of useful aliphatic alcohols include octanol, nonanol, decanol, dodecanol, hexadecanol, chimyl alcohol and selachyl alcohol.

Useful terpenoids include retinol, retinal, bisabolol, citral, citronellal, citronellol and linalool.

Useful mono- and di-acylglycerols include mono-, and di-esterified glycerols, wherein the acyl groups include from 8 to 20 carbon atoms, including 8 to 16 carbon atoms.

Useful polyethylene glycols have the formula H—(O—$CH_2$—$CH_2$)$_n$—OH, where n, the number of ethylene oxide units, is from 4 to 14. Examples of useful polyethylene glycols include PEG 200 (n=4), PEG 400 (n=8-9), and PEG 600 (n=12-14).

Useful polyethylene glycol fatty alcohol ethers, wherein the ethylene oxide units (n) are between 1 to 8, and the alkyl group is from $C_8$ to $C_{18}$.

A side-chain with amphipathic characteristics, i.e. asymmetric distribution of hydrophilic and hydrophobic groups, may facilitate e.g. the accessibility of a triterpene aldehyde to a cellular receptor. It is also possible that the presence of a negatively-charged carboxyl group in such a side-chain may contribute to the repulsion of the triterpene groups, thus allowing them a greater degree of rotational freedom. This last factor would most likely increase the accessibility of cellular receptors to the imine-forming carbonyl group In one preferred embodiment, when a saponin is linked to a lipophilic moiety, or to a bioactive agent, including a genetic determinant, by preparation of an active ester of glucuronic acid, a saponin component, followed by reaction of the active ester with a nucleophilic functional group on the lipophilic moiety, or the bioactive agent including a genetic determinant, such active esters may include the glucuronate of N-hydroxysuccinimide, sulfo-N-hydroxysuccinimide, hydroxybenzotriazole, and p-nitrophenol. The active esters may be prepared by reaction of the carboxy group of the saponin with an alcohol in the presence of a dehydration agent such as dicyclohexylcarbodiimide (DCC), 1-(3-dimethylaminopropyl)-3ethylcarbodiimide (EDC), and 1-(3-dimethylaminopropyl)-3-ethylcarbodiimide methiodide (EDCI).

The use of EDC to form conjugates is disclosed in U.S. Pat. No. 4,526,714 to Feijen et al. and PCT application publication No. WO91/01750, and Arnon, R et al., Pros. Natl. Acad. Sci. (USA) 77:6769-6772 (1980), the disclosures of which are fully incorporated by reference herein. The bioactive agent including a genetic determinant is then mixed with the activated ester in aqueous solution to give the conjugate.

Where a linker group between the saponin and the bioactive agent including a genetic determinant is desired, the active ester of the saponin glucuronate is prepared as described above and reacted with the linker group, e.g. 2-aminoethanol, an alkylene diamine, an amino acid such as glycine, or a carboxy-protected amino acid such as glycine tert-butyl ester.

If the linker contains a protected carboxy group, the protecting group is removed and the active ester of the linker is prepared (as described above). The active ester is then reacted with the bioactive agent including a genetic determinant to give the conjugate. Alternatively, the bioactive agent including a genetic determinant may be derivatized with succinic anhydride to give an antigensuccinate conjugate which may be condensed in the presence of EDC or EDCI with a saponin-linker derivative having a free amino or hydroxyl group on the linker, as described in WO91/01750.

It is also possible to prepare a saponin conjugate comprising a linker with a free amino group (derived from an alkylene diamine) and crosslink the free amino group with a heterobifunctional cross linker such as sulfosuccinimidyl 4-(N-maleimidocyclohexane)-1-carboxylate which will react with e.g. a free sulfhydryl group of a bioactive agent including a genetic determinant, including any derivative thereof.

The saponin may also be coupled to a linker group by reaction of the aldehyde group of the quillaic acid residue with an amino linker to form an intermediate imine conjugate, followed by reduction with sodium borohydride or sodium cyanoborohydride. Examples of such linkers include amino alcohols such as 2-aminoethanol and diamino compounds such as ethylenediamine, 1,2-propylenediamine, 1,5-pentanediamine, 1,6-hexanediamine, and the like. The bioactive agent including a genetic determinant may then be coupled to the linker by first forming the succinated derivative with succinic anhydride followed by condensation with the saponin-linker conjugate with DCC, EDC or EDCI.

In addition, the saponin may be oxidized with periodate and the dialdehyde produced therefrom condensed with an amino alcohol or diamino compound listed above. The free hydroxyl or amino group on the linker may then be condensed with the succinate derivative of the bioactive agent including a genetic determinant in the presence of DCC, EDC or EDCI.

Further useful linker groups are known in the art and examples are disclosed in e.g. U.S. Pat. No. 6,080,725, which is incorporated herein by reference.

Contacting Groups

A contacting group according to the present invention is a group comprising a lipophilic moiety and a moiety capable of association with a genetic determinant by means of either i) electrostatic interaction, or ii) hydrophobic interaction. Preferably, the contacting group comprises a lipophilic moiety and a moiety capable of forming a stable complex with a genetic determinant by means of either i) electrostatic interaction, or ii) hydrophobic interaction. In one embodiment the contacting group is capable of association with a genetic determinant by means of intercalation.

In one preferred embodiment the genetic determinant is a nucleic acid or a derivative of a nucleic acid, for example the genetic determinant may be DNA.

The lipophilic moiety may in one embodiment comprise or consist of a lipid, however the lipophilic moiety is not limited to compounds comprising a lipid. For example the lipophilic moiety may be a lipophilic peptide or part of a peptide, for example $(His)_6$.

One preferred contacting group is a cationic compound or group comprising at least one positively charged moiety at pH=7.0, which is capable of association with a genetic determinant, or which is capable of forming a stable complex with a genetic determinant. Such moieties may e.g. be found in both saponins and sterols, and they may be found in lipophilic moieties according to the present invention.

The overall charge of such a contacting group may be neutral or even anionic, as long as the contacting group comprises at least one positively charged moiety at pH=7 capable of association with a genetic determinant. Contacting groups can also be neutral in which case predominantly hydrophobic interactions with a genetic determinant are formed.

Contacting groups according to the present invention does not comprise such cationic compounds or such compounds comprising at least one positively charged moiety at pH=7, which are not capable of associating with a genetic determinant. Hence, contacting groups according to the invention does not include for example phosphatidylcholine, phosphatidylethanolamine, N-decanoyl-N-methylglucamine or N-decanoyl-N-methyl-amine.

Figure 5:
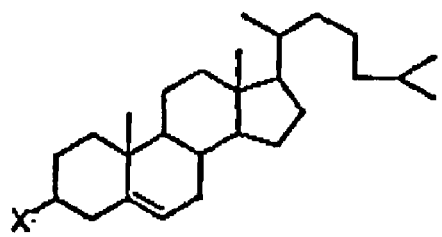
FIG. 5 illustrates preferred second sterols according to the invention and capable of being incorporated into the complexes according to the present invention. The listed compounds are ChoTB and ChoSC as described by Leventis, R. et.al. (1989) Biochim Biophys Acta 1023, 124; DC-Chol and TC-Chol as described by Avanti Lipids and further characterised herein; Lipid 67 (also known as GL-67), as described by Lee, E. R. et al. (1996) Human Gene Therapy 7,1701; BGTC is an acronym for 3-beta[N', N'-diguanidioethyl-aminoethane)carbamoyl]cholesterol; and BGSC is an acronym for 3-beta[4N-(1N,8N-diguanidino spermidine)-carbamoyl] cholesterol.
Figure 5:
Figure 5:
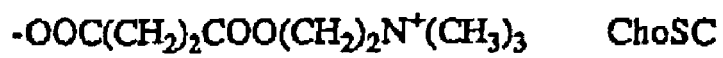
Figure 5:
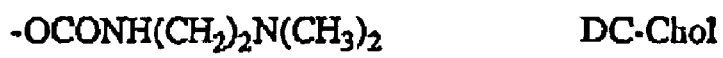
Figure 5:
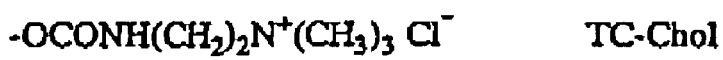
Figure 5:
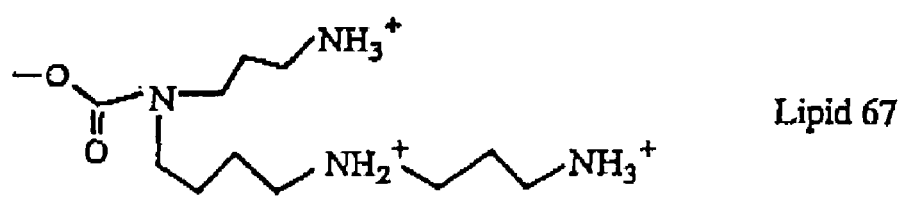
Figure 5:
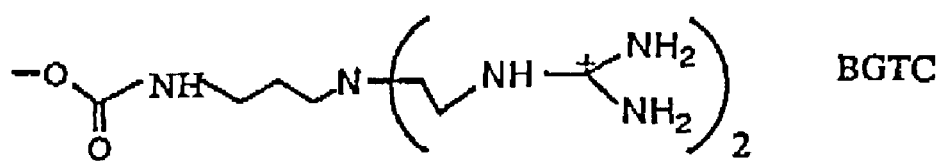
Figure 5:
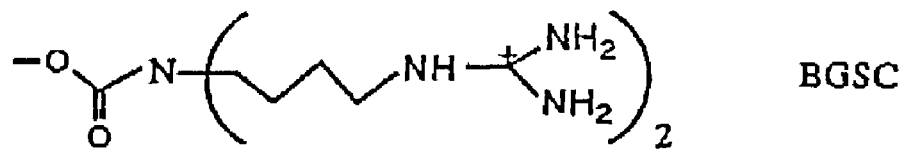
Figure 6:
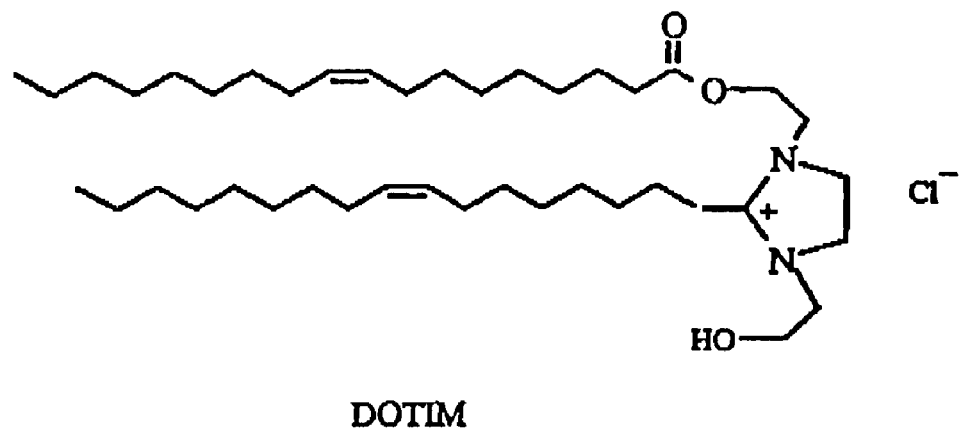
FIG. 6 illustrates preferred lipophilic moieties according to the invention and capabale of being incorporated into the complexes according to the present invention. The listed compounds are DOTIM, or 1-[2-(9(Z)-octadecenoyloxy) ethyl]-2-(8(Z)-heptadecenyl)-3-(2-hydroxy-ethyl)-imidazoliniumchloride, DODAC is an acronym for dioleoyidimethylammonium chloride, and GAP-DLRIE is an acronym for (+/−)—N—(3-aminopropyl)-N,N-dimethyl-2,3-bis(dodecyloxy)-1-propanaminium bromide.
Figure 6:
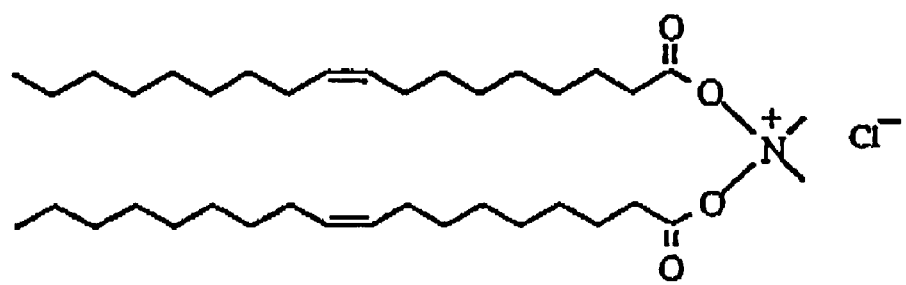
Figure 6:
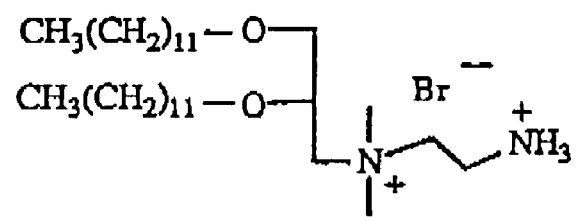
Figure 7:
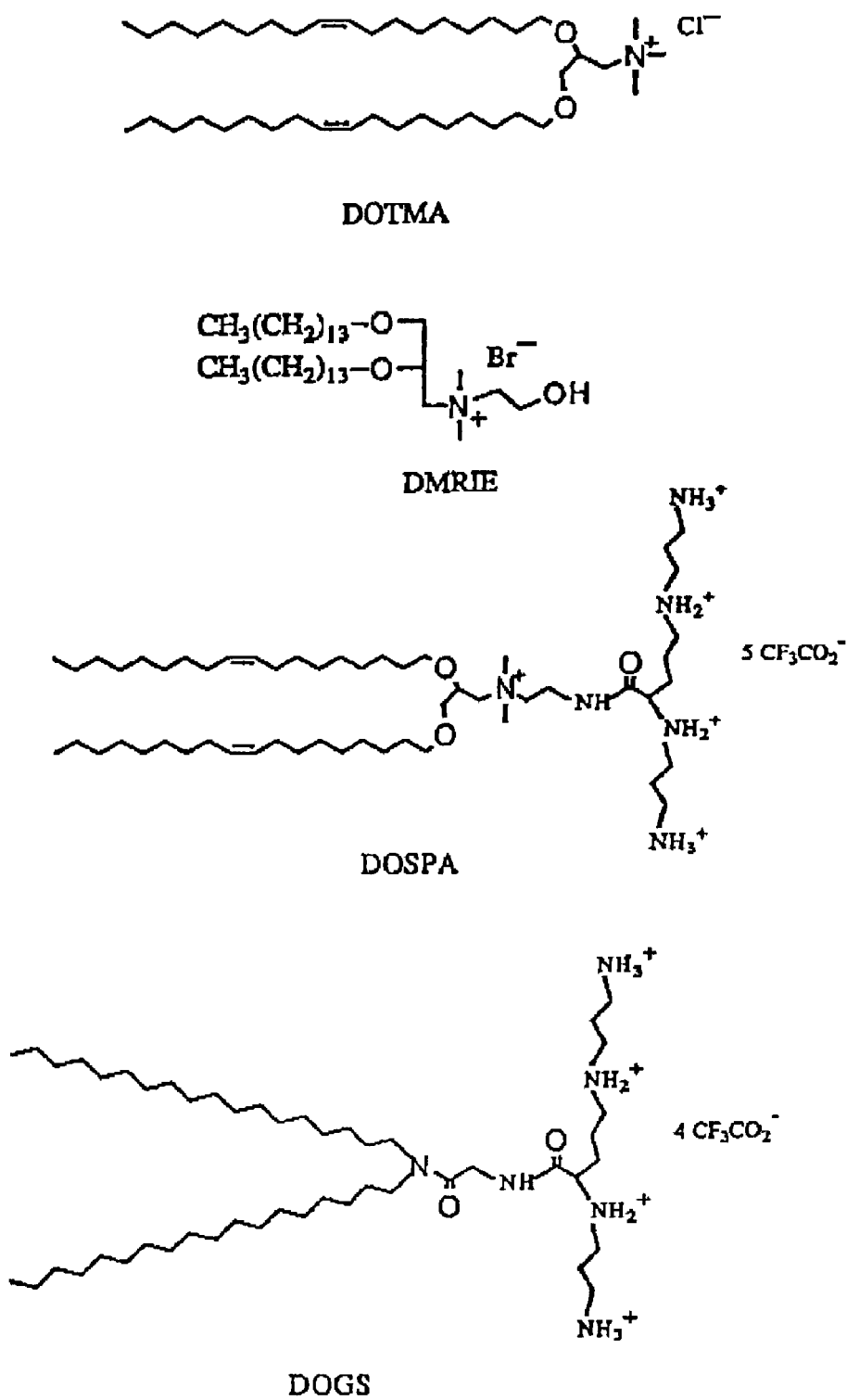
FIG. 7 illustrates yet further preferred lipophilic moieties capable of being incorporated into the complexes according to the present invention. The listed compounds are DOTMA, or N-[1-(2,3-dioleoyloxy)propyl]-N,N,N-trimethylammonium chloride, DMRIE, or N,N-dimethyl-1,2-dimyristoyloxy-3-aminopropane, DOSPA, or 2,3-dioleoyloxy-N-[2 (sperminecarboxamido)ethyl]-N,N-dimethyl-1-propanammonium trifluoroacetate, and DOGS, or Transfectam(R), as described by Behr, J. P. et.al. (1989) Proc. Natl. Acad. Sci. USA 86,6982, U.S. Pat. No. 5,171,678.

Examples include, but are not limited to quarternary ammonium compounds; dialkyldimethylammonium compounds; dioctadecyldimethyl ammonium chloride; dioctadecyldimethyl ammonium bromide; dioctadecyl/octadienyldimethyl ammonium chloride; dioctadecyl/octadienyldimethyl ammonium bromide; dimethyldioctadecylammonium bromide (DDAB), dodecyltrimethylammonium bromide, hexadecyltrimethylammonium compounds, mixed alkyltrimethylammonium bromide (Cetrimide per BP); and tetradecyltrimethylammonium compounds. Further preferred contacting groups are illustrated in FIGS. 5 (for sterols), and FIGS. 6, 7 and 8 (for lipophilic moieties).

Additionally preferred contacting groups includes, but is not limited to, compounds comprising an essentially planar group that is capable of forming an intercalation between stacked bases of nucleic acids, including single stranded DNA (ssDNA), double stranded DNA (dsDNA), single stranded RNA (ssRNA), double stranded RNA (dsRNA), RNA and/or DNA comprising both a single stranded part and a double stranded part, small nuclear RNA (snRNA), hetroduplexes of RNA and DNA, including hetroduplexes of RNA and DNA comprising both a single stranded part as well as a double stranded part, peptide nucleic acids (PNA), locked nucleic acids (LNA), and the like. Examples of such contacting groups include, but is not limited to, acridines and phenanthridines, and derivatives thereof, cumarins, furocumarins, phytoalexins (e.g. psoralens), and derivatives thereof. Such contacting groups may occur either individually in a complex or in any combination with one or more additional contacting groups capable of forming an intercalation between stacked bases of nucleic acids as described herein above.

Further examples of preferred contacting groups includes, but is not limited to, indoles and imidazoles, including compounds such e.g. 4',6-diamidio-2-phenylindole, 4',6-(diimidazolin-2-yl)-2-phenylindole) (obtainable as Hoechst 33258, and Hoechst 33342, respectively), Actinomycin D (such as e.g. 7-Aminoactinomycin D); Cyanine dyes, dimers of cyanine dyes (such as e.g. TOTO (R), YOYO (R), BOBO (TM), POPO (TM)) and derivatives thereof.

Any compound having an affinity for a nucleic acid moiety can be used as a contacting group in accordance with the present invention. Accordingly, in addition to intercalating groups, non-intercalating contacting grups can also be used. An example is hydroxystilbamidine (Fluoro-Cold (TM)) and derivatives hereof.

A comprehensive list of contacting groups capable of contacting nucleic acids and/or having an affinity to nucleic acids can be found e.g. In "Handbook of Fluorecent Probes and Researc Chemicals", by Richard P. Haugland, Sixth Edition, Molecular Probes (c) 1996, chapter 8, "Nucleic Acid Detection". The compounds listed in the Haugland reference can be readily modified by the skilled person exerting nothing more than ordinary skill in the art in order to obtain derivatives and analogues of said compounds listed therein.

Additionally prefered contacting groups are peptides and polypeptides including proteins, enzymes, co-enzymes, antibodies or binding fragments of antibodies having an affinity to nucleic acids, including the nucleic acids listed herein immediately above. Examples include, but is not limited to, nucleic acid binding proteins, including DNA binding proteins and proteins comprising a helix-turn-helix motif, including an alpha-helix-beta-turn-alpha-helix motif associated with the binding of DNA, Bacteriphage T4 gene 32 protein, *E. coli* single-stranded binding protein, RecA and homologues thereof, including *E. coli* RecA protein, Cytochrome C, monoclonal antibodies, Fab' fragments of antibodies, and polyclonal antibodies.

Contacting groups may also be any nucleic acid capable of forming an association with another nucleic acid, and an analogous compound, including PNA and LNA, or a derivative thereof. The association may be formed by hydrogen bonding or any other interaction resulting in base-pairing and/or duplex formation and/or triplex formation with at least one genetic determinant. Examples include oligonucleotides and oligonucleotides modified with lipophilic compounds.

Lipophilic Moieties

As described herein above, lipophilic moieties may serve the purpose of facilitating complex formation while at the same time acting as a "docking" group for contacting groups and/or targeting ligands The lipophilic moieties may thus form part of the complexes according to the present invention.

Lipophilic moieties according to the present invention are any moiety, including any residue of a lipophilic molecule, which is attached to or in contact with either i) any suitable functional group of one or more compounds that is essentially non-polar, or ii) forms an essentially non-polar domain within the complexes according to the present invention.

The lipophilic moiety can be a portion of an amphipathic compound. An amphipathic compound is a compound whose molecules contain both polar and non-polar domains. Surfactants are examples of amphipathic compounds. Surfactants typically possess a non-polar portion that is often an alkyl, aryl or terpene structure. In addition, a surfactant possesses a polar portion, that can be anionic, cationic, amphoteric or non-ionic. Examples of anionic groups are carboxylate, phosphate, sulfonate and sulfate. Examples of cationic domains are amine salts and quaternary ammonium salts. Amphoteric surfactants possess both an anionic and a cationic domain. Non-ionic domains are typically derivatives of a fatty acid carboxy group and include saccharide and polyoxyethylene derivatives.

A lipophilic moiety can also comprise two or more compounds possessing non-polar domains, wherein each of the compounds has been bonded to a linking group, which, in turn, is covalently attached to a component of the complex-according to the present invention, including any saponin component and/or any sterol component comprised in said complex, including any residues of said sterol component and any residues of said saponin component, including any aglycone part and/or any saccharide part.

One group of preferred lipophilic moieties are phospholipids such as phosphatidylcholine, phosphatidylethanolamine, triglycerides, fatty acids, and hydrophobic amino acids residues including membrane spanning hydrophobic amino acid segments.

When the complexes according to the present invention comprises i) a saponin derived from a Quil A fraction as described by WO 92/06710, which is incorporated herein by reference, ii) cholesterol and iii) phosphatidylcholine or phosphatidylethanolamine, the complex further comprises at least one bioactive agent, including a genetic determinant, including a polynucleotide, including any derivative thereof as described herein. In one embodiment, such complexes have a ratio (weight per weight) of i) lipid and cholesterol to ii) saponin, of more than 1:2, such as more than 1.5:2, and a lipid concentration of more than 1 mg/ml, for example more than 1.2 mg/ml.

Examples of lipophilic moieties capable of being used in connection with the present invention are lipids other than sterols, for example fats or fat resembling substances such as e.g. triglycerides or mixed triglycerides containing fatty acids with up to 50 carbon acids such as saturated fatty acids having for example 4, 5, 6, 7, 8, 9, 10, 11, 12, 13, 14, 15, 16, 17, 18, 19, 20, 21, 22, 23, 24, 25, 26, 27, 28, 29 and 30 carbon atoms e.g. burytic acid, caprole acid, caprylic acid, captic acid, lauric acid, myristic acid, palmitic acid, stearic acid, arachidic acid, behenic acid, lignoceric acid: unsaturated fatty acids with up to 30 carbon atoms, such as hexadecene acid, oleic acid, linoleic acid, linolenic acid, arachidonic acid; hydroxyfatty acids such as 9,10-dihydroxy stearic acid; unsaturated hydroxy fatty acids such as castor oil; branched fatty acids such as glycerol ethers; waxes i.e. esters between higher fatty acids and monohydric alcohols; phospholipides such as derivatives of glycerol phosphates such as derivatives of phosphatidic acids i.e. lecithin, cephalin, inositol phosphatides, spingosine derivatives with 14, 15, 16, 17, 18, 19 and 20 carbon atoms; glycolipids; isoprenoids; sulpholipids; and carotenoids.

Additional examples of lipophilic moieties capable of forming part of the complexes according to the present invention are cationic lipids. It will be understood that cationic lipids according to the definition applied herein are lipids carrying a net positive charge at pH 7.0.

Cationic lipids which may be used in the compositions of the present invention include, for example, phosphatidyl ethanolamine, phospatidyl choline, glycero-3-ethylphosphatidyl choline and fatty acyl esters thereof, di- and trimethyl ammonium propane, di- and tri-ethylammonium propane and fatty acyl esters thereof. A preferred derivative from this group is N-[1-(2,3-dioleoyloxy)propyl]-N,N,N-trimethylammonium chloride ("DOTMA").

Additionally, a wide array of synthetic cationic lipids can function in the present invention. These include common natural lipids derivatized to contain one or more basic functional groups. Examples of lipids which can be so modified include, for example, dimethyidioctadecylammonium bromide, sphingolipids, sphingo-myelin, lysolipids, glycolipids such as ganglioside GM1, sulfatides, glycosphingolipids, cholesterol and cholesterol esters and salts, N-succinyldioleoyl-phosphatidyl ethanolamine, 1,2,-ioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidyl ethanolamine and palmitoylhomocystiene.

In one embodiment, the cationic lipid in the composition of the present invention is a fluorinated cationic lipid. Any of the cationic lipids described herein may be fluorinated by replacing at least one hydrogen atom with a fluorine atom Specially synthesized cationic lipids also function in the present invention, including those compounds of formula (I), formula (II) and formula (III), described in U.S. Pat. No. 6,120,751, the disclosure of which is hereby incorporated by reference herein in its entirety.

Further examples of lipophilic moieties capable of forming part of complexes according to the present inventon are, for example, N,N'-Bis (dodecyaminocarbonyl-methylene)-N,N'-bis (β-N,N,N-trimethylammoniumethyl-aminocarbonylmethylene)-ethylenediamine tetraiodide; N,N"-Bis (hexadecylamino-carbonyl-methylene)-N,N',N"-tris (β-N,N,N-trimethylammoniumethylaminocarbonyl-methylenediethylene-triamine hexaiodide: N,N'-Bis (dodecylaminocarbonylmethylene)-N,N"-bis(β-N,N,N-trimethylammoniumeth ylaminocarbonylmethylene)cyclohexylene-1,4diamine tetraiodide; 1, 1, 7 ,7-tetra-(β-N,N,N, N-tetramethylammoniumethylamino-carbonylmethylene)-3-hexadecylaminocarbonylmethylene-1, 3, 7-triaazaheptane heptaiodide; and N,N,N'N'-tetra (β-N,N,N-trimethylammoniumethylaminocarbonylmethylene)-N'-(1,2-dioleoylglycero-3-phosphoethanolminocarbonylmethylene)-diethylenetriamine tetraiodide.

In one preferred embodiment, the cationic lipid is a fluorinated cationic lipid. Any of the cationic lipids described herein may be fluorinated by replacing at least one hydrogen atom with a fluorine atom. One skilled in the art will recognize that countless other natural and synthetic variants carrying positive charged moieties will also function in the invention.

In addition to the cationic lipids described above, other suitable lipids which may be used in the present invention include, for example, fatty acids, lysolipids, fluorinated lipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines, which target blood clots; phosphatidylcholine with both saturated and unsaturated lipids, including dioleoylphosphatidylcholine; dimyristoylphosphatidylcholine (DMPC); dipentadecanoylphosphatidylcholine; dilauroylphosphatidylcholine; dipalmitoylphosphatldylcholine (DPPC); distearoylphosphatidylcholine (DSPC); and diarachidonylphosphatidylcholine (DAPC); phosphatidylethanolamines, such as dioleoylphosphatidylethanolamine, dimyristoylphosphatidyletanolamine (DMPE), dipalmitoylphosphatidylethanolamine (DPPE) and distearoylphosphatidylethanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as dipalmitoylphosphatidic acid (DPPA) and distearoylphosphatidic acid (DSPA); paimitic acid; steaho acid; arachidonic acid; oleic acid; linolenic acid; linoleic acid; myristic acid; synthetic lipids described in U.S. Pat. No. 5,312,617, the disclosure of which is hereby incorporated by reference herein in its entirety.

Aditionally preferred lipophilic moieties include, but is not limited to glycolipids, phosphatldylethnolamine, phosphatidylcholine, phosphatydllinositol, phosphatidylserine, phosphatidylglycerol, including derivatives thereof. Further preferred lipophilic moieties are sphingomyelin, diphosphatidylglycerol (Cardiolipin), phosphatidic acid, Tfx™Reagents, including Tfx™-10 Reagent, Tfx™-20 Reagent, and Tfx™-50 Reagent, and 1,2-Diacyl-sn-Glycero-3-Ethylphosphocholine compounds, particular compounds wherein the acyl groups, independently from another, is selected from the group consisting of lauroyl, myristoyl, palmitoyl, stearoyl, oleoyl, palmitoyl-oleoyl, and of dilauroyl, dimyristoyl, dipaimitoyl, distearoyl, dioleoyl (DOPC+). L-α-Dioleoyl Phosphatidylethanolamine, or 1,2-dioleoyl-sn-glycero3-phospho-ethanolamine (DOPE) represents one particularly preferred lipophilic moiety.

Additionally preferred are DOTAP; DDAB (dimethyl dioctadecylammonium bromide); 1,2-Dioleoyl-sn-glycero-3-phosphoethanolamine DOPE; L-β,γ-Dioleoyl-α-cephalin; 3-sn-Phosphatidylethanolamine, 1,2-dideoyl N-(1-[2,3Dioleoyloxy]propyl)-N,N,N-trimethylammonium; Dioctadecyl dimethyl ammonium bromide; Avridine (CP-20,961), and stearyl tyrosine.

One particularly interesting lipophilic moiety is Monophosphoryl lipid A (MPL) as described by Baldridge and Crane (1999) in Methods, vol. 19, no. 1, p. 103-107; by Zhou and Huang (1993) in Vaccine, vol. 11, no. 11, p. 1139-1144. and by Rudbach et al. (1995) in Chap. 13. in "The Theory and Practical Application of Adjuvants" (Stewart-Tull, ed), Wiley & Sons, Ltd. Cationic derivatives of MPL are also included in the present invention. MPL can be obtained from Corixa Corp. (www.corixa.com).

Additionally preferred lipolytic moieties are lipids bearing polymers, such as chitin, hyaluronic acid, polyvinylpyrrolidone or polyethylene glycol (PEG), also referred to herein as "pegylated lipids" with preferred lipid bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular w eight of about 5000: lipids bearing sulfonated mono-, di-, oligo- or polysaccharddes; cholesterol, cholesterol sulfate and cholesterol hemisuccinate; tocopherol hemisuccinate; lipids with ether and ester-linked fatty acids; polymerized lipids (a wide variety of which are known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as the class of compounds referred to as TWEEN.RTM., including, for example, TWEEN.RTM. 20, TWEEN.RTM. 40 and TWEEN.RTM. 80, commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxy-propylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including, glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5cholesten-3β-yloxy)-1-thio-β-D-galacto-pyranoside; digalactosyldiglyceride; 6-(5-cholesten-3β-yloxy)-hexyl-6-amino-6deoxy-1-thio-β-D-galact opyranoside; 6-(5 cholesten-3β-yloxy)hexyl-6-amino-6-deoxyl-1-thio-α-D-manno pyranoside; 12-(((7'-diethylaminocoumarin-3-yl)-carbonyl) methylamino)-octadecanoic acid; N-[12-(((7'-diethylaminocoumarin-3-yl)-carbonyl)methylamino)-octadecanoyl]-2-aminopalmitic acid; cholesteryl(4'-trimethylammonio) butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycero-phospho-ethanolamine and palmitoylhomocysteine, and/or any combinations thereof.

One skilled in the art could readily determine the charge (e.g., cationic, anionic or neutral) of any of the lipids decribed herein. In a preferred embodiment, the lipids described herein are fluorinated lipids. As one skilled in the art will recognize, any of the neutral lipids described herein may be modified to cationic lipids or anionic lipids by methods that are well-known to one skilled in the art. For example, any modifiable group on a neutral lipid, such as a secondary amine, an —OH group or an anionic group or cationic group that have a zwitterionic charge balance, may be chemically modified to add or subtract a charge to the neutral lipid.

When a neutral lipid is used in the compositions of the present invention, the neutral lipid is preferably a phosphocholine, a sphingolipid, a glycolipid, a glycosphingolipid, a phospholipid or a polymerized lipid.

Examples of polymerized lipids include unsaturated lipophilic chains such as alkenyl or alkynyl, containing up to about 50 carbon atoms. Further examples are phospholipids such as phosphoglycerides and sphingolipids carrying polymerizable groups; and saturated and unsaturated fatty acid derivatives with hydroxyl groups, such as for example triglycerides of d-1,2-hydroxyoleic acid, including castor oil and ergot oil. Polymerization may be designed to include hydrophilic substituents such as carboxyl or hydroxyl groups, to enhance dispersablilty so that the backbone residue resulting from biodegradation is water soluble. Suitable polymerizable lipids are also described, for example, by Klaveness et al, U.S. Pat. No. 5,536,490, the disclosure of which is hereby incorporated by reference herein in its entirety.

Even further examples of lipophilic moieties capable of forming part of complexes according to the present inventon are those e.g. described in EP 0 109 952 B1, incorporated herein by reference, and in EP 0 436 620 B1, incorporated herein by reference. In particular, the lipophilic moiety may be a phospholipid such as phosphatidyl-ethanolamine and phosphatidylcholine.

The lipophilic moiety may comprise a lipophilic receptor molecule capable of binding a cell-binding component such as e.g. an antigen. Examples of such receptors are e.g. glycolipids, for example the cholera toxin's receptor ganglioside GM1 and fucosylated blood group antigen. The cell-binding component can then function as a transport molecule.

Lipophilic Moieties Bound to Polymers

In one embodiment, the lipophilic moiety of the complex according to the invention is covalently bonded to at least one polymer including, for example, hydrophilic polymers. Suitable hydrophilic polymers for covalent bonding to lipids include, for example, polyalkyleneoxides such as, for example, polyethylene glycol (PEG) and polypropylene glycol (PPG), polyvinyl-pyrrolidones, polyvinylalkylethers, such as a polyvinylmethyl ether, polyacrylamides, such as, for example, polymethacrylamides, polydimethyl-acrylamides and polyhydroxy-propylmethacrylamides, polyhydroxyakyl(meth)-acrylates, such as polyhydroxyethyl acrylates, polyhydroxypropyl methacrylates, polyalkyloxazolines, such as polymethyloxazolines and polyethyloxazoliries, polyhydroxyalkyloxazolines, such as polyhydroxyethyloxazolines, polyhyhydroxypropyloxazolines, polyvinyl alcohols, polyphosphazenes, poly(hydroxyalkylcarboxylic acids), polyoxazolidines, polyaspartamide, and polymers of sialic acid (polysialics).

Preferably, the hydrophilic polymers are polyethylene glycol, polyvinyl pyrrolidone, polyvinyl alcohol, polypropylene glycol, a polyvinylalkylether, a polyacrylamide, a polyalkyloxazoline, a polyhydroxyalkyloxazoline, a polyphosphazene, a polyoxazolidine, a polyaspartamide, a polymer of sialic acid, a polyhydroxyalkyl(meth)acrylate or a poly(hydroxyalkylcarboyxlic acid).

More preferably, the hydrophilic polymers are PEG, PPG, polyvinylalcohol, polyvinylpyrrolidone and copolymers thereof, with PEG and PPG polymers being more preferred and PEG polymers being even more prefered. The polyethylene glycol may be, for example, PEG 2000, PEG 5000 or PEG 8000, which have weight average molecular weights of 2000, 5000 and 8000 daltons, respectively.

Preferably, the polyethylene glycol has a molecular weight of about 500 to about 20,000, more preferably from about 1,000 to about 10,000. Other suitable polymers, hydrophilic and otherwise, will be apparent to one skilled in the art based on the present disclosure.

Exemplary lipids which are covalently bonded to hydrophilic polymers include, for example, dipalmitoylphosphatidylethanolamine-PEG, dioleoylphosphatidylethanolamine-PEG and distearylphosphatidylethanolamine-PEG, more preferably dipalmitoylphosphatidylethanolamine-PEG.

Liposomes

The above-mentioned polymers which may in one embodiment be attached to e.g. a lipophilic moiety of the complexes according to the invention. The attachment may be by means of alkylation or acylation reactions and this is useful for improving the stability and size of the distribution of liposomes comprising the complexes according to the invention.

The liposomes may be prepared e.g. as described by Lipford and Wagner (1994) in Vaccine, vol. 12, no. 1, p. 73-80, incorporated herein by reference. General liposomal preparatory techniques which may be adapted for use in the preparation of liposome compositions pertaining to the present invention are discussed, for example, in U.S. Pat. Nos. 4,728,578, 4,728,575, 4,737,323, 4,533,254, 4,162,282, 4,310,505, and 4,921,706; U.K. Patent Application GB 2193095A; International Application Serial Nos. PCT/US85/01161 and PCT/US89/05040; Mayer et al., Biochimica et Biophysica Acta, 858:161-168 (1986); Hope et al., Biochimica et Biophysica Acta, 812:55-65 (1985); Mayhew et al., Methods in Enzymology, 149:64-77 (1987); Mayhew et al., Biochimica et Biophysica Acta, 755:169-74 (1984); Cheng et al, Investigative Radiology, 22:47-55 (1987); and Liposome Technology, Gregoriadis, G., ed., Vol. 1, pp. 29-31, 51-67 and 79-108 (CRC Press Inc., Boca Raton, Fla. 1984), the disclosures of each of which are hereby incorporated by reference herein.

Accordingly, the liposome compositions of the invention comprising the complexes of the invention may be prepared using any one of a variety of conventional liposomal preparatory techniques which will be apparent to one skilled in the art, including, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the compositions in various fashions. See, e.g., Madden et al., Chemistry and Physics of Lipids, 53:37-46 (1990), the disclosure of which is hereby incorporated herein by reference.

Suitable freeze-thaw techniques are described, for example, in International Application Serial No. PCT/US89/05040, filed Nov. 8, 1989, the disclosure of which is hereby incorporated herein by reference in its entirety. Methods, which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing, which may be achieved, for example, by the use of a mechanical shaking device, such as a Wig-L-Bug.TM. (Crescent Dental, Lyons, Ill.), a Mixomat (Degussa AG Frankfurt, Germany), a Capmix (Espe Fabrik Pharmazeutischer Praeparate GMBH & Co., Seefeld, Oberay Germany), a Silamat Plus (Vivadent, Lechtenstein), or a Vibros (Quayle Dental, Sussex, England). Conventional microemulsification equipment, such as a Microfluidizer.TM. (Microfluidics, Woburn, Mass.) may also be used.

Bioactive Agents

The complexes according to the present invention may further comprise one or more bioactive agents. Examples of bioactive agents are therapeutic agents, diagnostic agents, targeting ligands, and genetic determinants. However, targeting ligands and genetic determinants may also be used without being bioactive agents. In the latter case, the targeting ligand is merely targeting the complex to a desired cellular location, or a predetermined region of a patient, and the genetic determinant may be e.g. DNA encoding a bioactive agent in the form of the corresponding polypeptide. However, the DNA itself may also act as a bioactive agent in this respect.

Charged bioactive agents, such as DNA, can be readily incorporated into the complexes through e.g. covalent or non-covalent interactions, such as ionic or electrostatic interactions, formed between second sterols, second saponins, or, in the absence of the aforementioned, a contacting group.

The bioactive agent, e.g. DNA, may be added to the complex at the initial stage of preparation thereof. However, Also the DNA may also be added at a later stage when e.g. the components of the complex have been mixed and complex formation achieved.

A wide variety of bioactive agents may be delivered to a predetermined cellular location, or to a particular region of a patient, by using the present invention based on complexes comprising at least one bioactive agent. Suitable bioactive agents include, for example, contrast agents, genetic determinants, chemotherapeutics, peptides and nucleic acids, including derivatised nucleic acids such as e.g. LNA (locked nucleic acids) and PNA (peptide nucleic acids).

One preferred bioactive agent is a genetic determinant, which includes, for example, nucleic acids, RNA and DNA, of either natural or synthetic origin, including recombinant RNA and DNA and antisense RNA and DNA, hammerhead RNA, ribozymes, hammerhead ribozymes, antigene nucleic acids, both single and double stranded RNA and DNA and analogs thereof, ribooligonucleotides, deoxyribooligonucleotides, antisense ribooligonucleotides, and antisense deoxyribooligonucleotides.

The complexes of the present invention are also suitable for the administration of a wide variety of peptide and non-peptide bioactive agents. Bioactive agents, such as peptides, can also be incorporated when they are hydrophobic, neutral or charged. In many cases by using the appropriate complex composition, an interaction can be formed between the complex and a peptide of interest, or any other bioactive agent.

Some examples of peptides which may be incorporated into the compositions are interferons and other macrophage activation factors, such as lymphokines, muramyl dipeptide (MDP), $\gamma$-interferon, $\alpha$-interferon and $\beta$-interferon, and related antiviral and tumoricidal agents; renin inhibitors including new-generation anti-hypertensive agents; cholecystokinins (CCK analogs) such as CCK, ceruletide and eledoisin, and related cardiovascular-targeting agents and CNS-targeting agents; leukotrienes and prostaglandins, such as oxytocin, and related anti-inflammatory, oxytocid and abortifacient compounds; erythropoietin and analogs thereof, as well as related haematinics; LHRH analogs, such as leuprolide, buserelin and nafarelin, and related down-regulators of pituitary receptors; parathyroid hormone and other growth hormone analogs; enzymes, such as Dnase, catalase and alpha-1 antrtrypsin; immunusuppressants such as cyclosporin; GM-CSF and other immunomodulators; and insulin.

Non-peptides which may be used in the compositions and methods of the present invention include, for example, beta-agonists, such as isoproterenol, albuterol, isoetherine and metoproteronol, and related anti-asthmatics; steroids, such as flunisolide, and similar anti-asthmatics; cholinergic agents, such as cromolyn, and related anti-asthmatics; and 5-lipoxygenase inhibitors, such as zileuton and the hydrpxyurea compound described above, and related leukotriene inhibitors.

Bioactive agents that act as antineoplastics and antibiotics may also be delivered using the compositions of the present invention. Among these are included, for example, antibiotics such as p-aminosalicylic acid, isoniazid, capreomycin sulfate cycloserine, ethambutol hydrochloride ethionamide, pyrazinamide, rifampin and streptomycin sulfate, dapsone, chloramphenicol, neomycin, ceflacor, cefadroxil, cephalexin, cephadrine erythromycin, clindamycin, lincomycin, amoxicillin, ampicillin, bacampicillin, carbeniciilin, dicioxicillin, cyclacillin, picioxicillin, hetacillin, methicillin, nafcillin, oxacillin, penicillin (G and V), ticarcillin rifampin, tetracycline and amphotericin B; and antitumor drugs such as methotrexate, fluorourcil, addamycin, mitomycin, ansamitomycin, bleomycin, cystiene arabinoside, arabinosyl adenine, mercaptopolylysine, vincristine, busulfan, chlorambucil, azidothymidine, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, taxol, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase, etoposide (VP-16), interferon α-2a, interferon α-2b, teniposide (VM-26), vinblastine sulfate (VLB), vincristine sulfate, hydroxyurea, procarbazine, and dacarbazine; mitotic inhibitors such as the vinca alkaloids, and steroids such as dexamethasone.

Other bioactive agents that may be used in the compositions of the present invention include, for example, LHRH analogs, 5-lipooxygenase inhibitors, immunosuppressants or bronchodilators; especially preferred materials include leuprolide acetate. The LHRH Ac-D-2-Nal-D-4-Cl-Phe-D-3-Pal-Ser-N-MeTyr-D-Lys(Nic)-Leu-Lys(N-Isp)-Pro-D-Ala-NH$_2$ (hereinafter "D-2-Nal"), the 5-lipoxygenase inhibitor N-[3-[5(4-fluorophenylmethyl)-2-thienyl]-1 methyl-2-propynyl]-N-hydroxyure a, the immunosuppressant cyclosporin A, and the adrenergic bronchodilators isoproterenol arid albuterol. (As used herein, the terms "5-lipoxygenase inhibitor" or "5-LO inhibitor" refer to any physiologically active compound capable of affecting leukotriene biosynthesis.)

Yet another example of bioactive agents capable of being incorporated into or associated with the complexes of the present invention includes, but is not limited to, apoptosis inducing proteins Apoptosis inducing proteins includes, but are not limited to BAX, BAD, bcl-xs, p53, and caspases (Sasaki et al. (2001), Nat. Biotechnol. 19, 543-547).

Furthermore, immunemodulators are yet another group of bioactive agents according to the present invention. Examples of immunemodulators includes, but are not limited to, IL-2, IL-4, IL-5, IL-10, IL-12, IL-15, INF-γ, TNF-β

Antigen presenting proteins constitute yet another group of bioactive agents. Examples of antigen presenting proteins includes MHC class I and MHC class II molecules or fragments thereof capable of antigen presentation. Preferred MHC class I molecules are HLA-B7 and HLA-A2.

A still further example of bioactive agents are cellular toxins such as bacterial toxins including, but not limited to, tetanus toxin and cholera toxin, or fragments thereof having domains capable of ADP-ribosylation (Mowat et al. (2001); J. Immunol. 167, 3398-3405).

Bioactive agents can also be those polypeptides involved in antigen/epitope presentation. Examples include tapasin involved in the loading of MHC class I molecule peptide loading, molecular chaperones, heat shock proteins (such as HSP blonging to the conserved Hsp 70, Hsp 90, Hsp 110 families (see e.g. Rafiee et al. (2001) Cancer Gene Ther. 8, 974-981))

For lipophilic drugs, the interaction may be hydrophobic or van der Waals forces. For charged drugs and lipid head groups, the interaction may be electrostatic interactions.

Targeting Ligands

In one embodiment the complexes according to the present invention further comprise a targeting ligand for targeting the complex to a particular location. Such locations may be a particular tissue or the surface of a particular cell type. Such tissues or cell types typically have a receptor moiety which has an affinity for the targeting ligand of the complex.

Suitable targeting ligands according to the present invention are e.g. hydrophobic receptor binding molecules, immunogenic and/or antigenic substances. Suitable cell surface receptors capable of contacting or interacting with the targeting ligands according to the invention are e.g. receptors comprising a lipophilic domaine, or receptors comprising or essentially consisting of hydrophobic proteins. By using targeting ligands in combination with the complexes according to the present invention, a greater proportion of complexes reach a predetermined destination. It is advantageous to use a targeting ligand e.g. when it is desirable to target the complex to a particular mucous membrane known to contain a component with affinity for a targeting forming part of a complex according to the invention. A special advantage in this respect is that lipid-containing cell surface receptor binding moieties can be used as an integrated lipophilic moiety in the complexes and optionally also replace lipophilic moieties that are used to build up the complex.

Among the receptor-binding components that are comprised by the invention are, for example, bacterial toxins and their active binding parts in the form of subunits or fragments or various modifications or derivatives thereof, bacterial fimbriae or other adhesion molecules and their active binding parts and/or derivative structures.

Preferred targeting ligands are associated with the complexes covalently or non-covalently. The targeting ligand may be bound, for example, via a covalent or non-covalent bond, to at least one of the lipids in the composition. Preferably, the targeting ligand is bound to the complexes covalently. In the case of lipid complexes which comprise cholesterol, the targeting ligand is preferably bound to the cholesterol substantially only non-covalently, and/or the targeting ligand is bound covalently to a component of the composition, for example, another lipid, such as a phospholipid, other than the cholesterol.

The targeting ligands which are incorporated in the complexes of the present invention are preferably substances which are capable of targeting receptors and/or tissues in vivo and/or in vitro. With respect to the targeting of tissue, the targeting ligands are desirably capable of targeting heart tissue and membranous tissues, including endothelial and epithelial cells. In the case of receptors, the targeting ligands are desirably capable of targeting GPIIbIIIa receptors or lymphocyte receptors, such as T-cells, B-cells or interleukin-2 receptors. Preferred targeting ligands for use in targeting tissues and/or receptors, including the tissues and receptors exemplified above, are selected from the group consisting of proteins, including antibodies, antibody fragments, hormones, hormone analogues, glycoproteins and lectins, peptides, polypeptides, amino acids, sugars, such as saccharides, including monosaccharides and polysaccharides, and carbohydrates, vitamins, steroids, steroid analogs, hormones, cofactors, and genetic determinants, including nucleosides, nucleotides, nucleotide acid constructs and polynucleotides, with peptides being particularly preferred.

An example of a protein which may be preferred for use as a targeting ligand is Protein A, which is protein that is produced by most strains of *Staphylococcus aureus*. Protein A is commercially available, for example, from Sigma Chemical Co. (St. Louis, Mo.). Protein A may then be used for binding a variety of IgG antibodies. Generally speaking, peptides which are particularly useful as targeting ligands include natural, modified natural, or synthetic peptides that incorporate additional modes of resistance to degradation by vascularly circulating esterases, amidases, or peptidases. A useful method of stabilization of peptide moieties incorporates the use of cyclization techniques. As an example, the end-to-end cyclization whereby the carboxy terminus is covalently linked to the amine terminus via an amide bond may be useful to inhibit peptide degradation and increase circulating half-life. Additionally, a side chain-to-side chain cyclization or end-to-side chain cyclization is also useful in inducing stability. In addition, the substitution of an L-amino acid for a D-amino acid in a strategic region of the peptide may offer resistance to biological degradation.

In another embodiment, small peptides which bind the interluekin-1 (IL-1) receptor may be used. For example, peptides generated by phage display core sequences of QPY have been shown to be essential for peptide binding, including, for example, AF12198, a 15-mer with a core sequence of WYQJY, where J is azetidine; and IL-1 antagonists with $K_d$ $10^{-10}$ to $10^{-12}$ M, such as AcPhe-Glu, Trp-Pro-Gly-Trp-Tyr-Gln-Aze-Tyr-Ala-Leu-Pro-Leu -$CONH_2$ or Ac-Phe-Glu-Trp-Pro-Gly-Trp-Tyr-Gln-Aze-Tyr-Ala-Leu-Pro-Leu-.

Endothelial-leukocyte adhesion molecules (ELAM's) are antigens which are expressed by endothelial cells under conditions of stress which then facilitate the migration of the leukocytes across the endothelium lining the vasculature into the surrounding tissues. These same endothelial-leukocyte adhesion molecules may also be advantageously exploited as receptors for targeting of vesicles. These endothelial cell adhesion molecules belong to a family known as selectins in which the known members, such as GMP-140, all participate in endothelial-leukocyte adhesion and include ELAM-1, LAM-1 and the granule membrane protein 140 (GMP-140) also known as platelet activation-dependent granule-external membrane protein (PADGEM), VCAM-1 /INCAM-110 (Vascular Adhesion Molecule/Inducible Adhesion Molecule) and ICAM-1 (Intercellular Adhesion Molecule).

A wide variety of different targeting ligands can be selected to bind to the cytoplasmic domains of the ELAM molecules. Targeting ligands in this regard may include lectins, a wide variety of carbohydrate or sugar moieties, antibodies, antibody fragments, Fab fragments, such as, for example, Fab'2, and synthetic peptides, including, for example, Arginine-Glycine-Aspartic Acid (R-G-D) which may be targeted to wound healing. While many of these materials may be derived from natural sources, some may be synthesized by molecular biological recombinant techniques and others may be synthetic in origin. Peptides may be prepared by a variety of techniques known in the art. Targeting ligands derived or modified from human leukocyte origin, such as CD11 a/CD18, and leukocyte cell surface glycoprotein (LFA-1), may also be used as these are known to bind to the endothelial cell receptor ICAM-1. The cytokine inducible member of the immunoglobulin superfamily, VCAM-1, which is mononuclear leukocyte-selective, may also be used as a targeting ligand. VLA-4, derived from human monocytes, may be used to target VCAM-1. Antibodies and other targeting ligands may be employed to target endoglin, which is an endothelial cell proliferation marker. Endoglin is upregulated on endothelial cells in miscellaneous solid tumors. A targeting ligand which may be used to target endoglin is the antibody TEC-11. Thorpe et al, Breast Cancer Research and Treatment, 36:237-51 (1995).

Endothelial cell activation in the setting of atherosclerosis is used in this invention to target the complexes to regions of arteriosclerosis including, for example, atherosclerotic plaque. One such target that can be used is the inducible mononuclear leukocyte endothelial adhesion molecule recognized by Rb1/9 as an ATHERO-ELAM. The monoclonal antibodies, H4/18 and H18/7, may be used to target endothelial cell surface antigens which are induced by cytokine mediators. As a preferred embodiment, complexes are targeted to atherosclerotic plaque to non-invasively detect diseased blood vessels before severe damage has occurred, for example, prior to stroke or myocardial infarction, so that appropriate medical or surgical intervention may be implemented. ATHERO-ELAM is a preferred target and ligands, such as antibodies, peptides, or lectins or combinations thereof may be used to target this cell surface epitope expressed on endothelial cells in the context of atherosclerosis. Alternatively, lipoproteins or lipoprotein fragments derived from low or high density lipoprotein proteins may be used as targeting ligands. Additionally, cholesterol may be used to target the endothelial cells and localize the lipids, vesicles, and the like, to regions of atherosclerotic plaque. In embodiments which involve the use of cholesterol as a targeting ligand, the cholesterol is preferably unmodified (non-derivatized) with other chemical groups, moieties and ligands.

A targeting ligand directed toward thrombotic material in plaque may be used to differentiate between active and inactive regions of atherosclerotic plaque. Active plaques in the process of generating thrombi are more dangerous since they may ultimately occlude a vessel or result in emboli. In this regard, in addition to low molecular lecular weight heparin fragments, other targeting ligands, such as, for example, anti-fibrin antibody, tissue plasminogen activator (t-PA), anti-thrombin antibody and fibrin antibodies directed to platelet activation factions, may be used to target active plaque with evolving clots. Most preferred targeting ligands are those which will target a plasma membrane associated GPIIbIIIa in activated platelets in addition to targeting P-selectin, and an antibody or associated antibody fragment directed to GPI-IbIIIa. The present invention is also useful for detecting regions of acute myocardial infarction. By attaching anti-myosin (particularly cardiomyosin) antibody or anti-actin antibodies to the lipids, infarcted myocardium may be detected by the methods of the present invention. For targeting to granulation tissue (healing wounds), many of the above targeting ligands may be useful, The wound healing tripeptide, arginine-glycine-aspartic acid (RGD), may also be used is a targeting ligand in this regard.

As with the endothelial cells discussed above, a wide variety of peptides, proteins and antibodies may be employed as targeting ligands for targeting epithelial cells. Preferably, a peptide, including synthetic, semi-synthetic or naturally-occurring peptides, with high affinity to the epithelial cell target receptor may be selected, with synthetic peptides being more preferred. In connection with these preferred embodiments, peptides having from about 5 to about 15 amino acid residues are preferred. Antibodies may be used as whole antibody or antibody fragments, for example, Fab or Fab'$_2$, either of natural or recombinant origin. The antibodies of natural origin may be of animal or human origin, or may be chimeric (mouse/human). Human recombinant or chimeric antibodies are preferred and fragments are preferred to whole antibody.

Examples of monoclonal antibodies which may be employed as targeting ligands in the present complexes include CALAM 27, which is formed by immunizing BALEI/c mice with whole human squamous cell carcinoma of the tongue and forming hybridomtas by crossing extracted spleen cells with those of an NS1 syngeneic myeloma cell line. Gioanni et al, Cancer Research, 47: 4417-4424 (1987). CALAM 27 is directed to surface epitopes of both normal and malignant epithelial cells. Normal lymph nodes generally do not contain cells expressing these epitopes. See Cancer Research, 47:4417-4424 (1987). Accordingly, complexes comprising this antibody can be used to target metastases in the lymph nodes. The monoclonal antibody 3C2 may be employed as a targeting ligarld for targeting malignant epithelial cells of serious ovarian carcinoma and endometrioid carcinoma. Another exemplary targeting ligand is Mab 4C7 (see Cancer Research, 45:2358-2362 (1985)), which may be used to target mucinous carcinoma, endometriod carcinoma and mesonephroid carcinoma. For targeting squamous cell carcinoma in head and neck cancer, Mab E48 (Biological Abstract, Vol. 099 Issue. 066 Ref 082748) may be used as a targeting ligand. For targeting malignant melanoma, the monoclonal antibody 225.28s (Pathol. Biol., 38 (8):866-869 (1990)) may be employed. The monoclonal antibody mAb2E$_1$, which is targeted to EPR-1 (effector cell protease 1), may also be used.

There are a variety of cell surface epitopes on epithelial cells for which targeting ligands may be selected. For example, the protein human papilloma virus (HPV) has been associated with benign and malignant epithelial proliferations in skin and mucosa. Two HPV oncogenic proteins, E6 and E7, may be targeted as these may be expressed in certain epithelial derived cancers, such as cervical carcinoma. See Curr. Opin. Immunol., 6(5);746-54 (1994). Membrane receptors for peptide growth factors (PGF-R), which are involved in cancer cell proliferation, may also be selected as tumor antigens. Anticancer Drugs, 5(4):379-93 (1994). Also, epidermal growth factor (EGF) and interleukin-2 (IL-2) may be targeted with suitable targeting ligands, including peptides, which bind these receptors. Certain melanoma associated antigens (MAA), such as epidermal growth factor receptor (EGFR) and adhesion molecules (Tumor Biol., 15 (4):188-202 (1994)), which are expressed by malignant melanoma cells, can be targeted with the complexes provided herein. The tumor associated antigen FAB-72 on the surface of carcinoma calls may also be selected as a target.

A wide variety of targeting ligands may be selected for targeting myocardial cells. Exemplary targeting ligands include, for example, anticardiomyosin antibody, which may comprise polyclonal antibody, Fab'$_2$ fragments, or be of human origin, anima origin, for example, mouse origin, or of chimeric origin.

Additional targeting ligands include dipyridamole; digitalis; nifedipine; apolipoprotein; low density lipoproteins (LDL), including α-LDL, vLDL and methyl LDL; ryanodine; endothelin; complement receptor type 1; IgG Fc; beta 1-adr-energic; dihydropyridine; adenosine; mineralocorticoid; nicotinic acetylcholine and muscarinic acetylcholine; antibodies to the human alpha 1A-adrenergic receptor; bioactive agents, such as drugs, including the alpha 1-antagonist prazosin; antibodies to the anti-beta-receptor: drugs which bind to the anti-beta-receptor; anti-cardiac RyR antibodies; endothelin-1, which is an endothelial cell-derived vasoconstrictor peptide that exerts a potent positive inotropic effect on cardiac tissue (endothelin-1 binds to cardiac sarcolemmal vesicles); monoclonal antibodies which may be generated to the T-cell receptor α-β receptor and thereby employed to generate targeting ligands; the complement inhibitor sCR1; drugs, peptides or antibodies which are generated to the dihydropyridine receptor; monoclonal antibodies directed towards the anti-interleukin-2 receptor may be used as targeting ligands to direct the present complexes to areas of myocardial tissue which express this receptor and which may be up-regulated in conditions of inflammation; cyclosporine for directing similarly the complexes to areas of inflamed myocardial tissue; methylisobutyl isonitrile; lectins which bind to specific sugars on membranes of cardiac myocytes and cardiac endothelial cells; adrenomedullin (ADM), which is an endogenous hypotensive and vasorelaxing peptide; atrial natriuretic peptide (ANP); C-type natriuretic peptide (CNP), which is a 22 amino acid peptide of endothelial cell origin and is structurally related to atrial natriuretic peptide but genetically distinct, and possesses vasoactive and antimitogenic activity; vasonatrin peptide (VNP) which is a chimera of atrial natriuretic peptide (ANP) and C-type natriuretic peptide (GNP) and comprises 27 amino acids; thrombin; endothelium-derived relaxing factor (EDRF); neutral endopeptidase 1 (NEP-1); competitive inhibitors to EDRF, including, for example, NG-monomethyl-L-arginine (L-NMMA); potassium channel antagonists, such as charybdotoxin and glibenclamide; antiheart antibodies, which may be identified in patients with idiopathic dilated cardiomyopathy but which preferably do not elicit cytolysis in the myocardium; antibodies directed against the adenine nucleotide translocator, the branched-chain keto acid dehydrogenase or cardiac myosin; specific antagonists for the endothelin-A receptor, which may be referred to as BQ-123; and antibodies to the angiotensin II receptor.

In one interesting embodiment the present invention relates to targeting ligands capable of targeting the dendritic cell receptor for endocytosis, DEC-205, as described by Mahnke and Guo (2000) in J. Cell. Biol., vol. 151, no. 3, p. 673-684; and by Jiang and Swiggard (1995) in Nature, vol. 375, no. 6527, p. 151-155.

In another interesting embodiment, the present invention relates to targeting ligands in the form of two of the major antigens of heart sarcolemmal are calcium binding glycoproteins which co-purify with the dihydropyridine receptor. Antisera may be raised, including polyclonal or monoclonal antibodies, against purified sarcolemma, and these antibodies may also be employed as targeting ligands. Purified fractions of the calcium binding glycoproteins may be isolated from the plasma membranes of the sarcolemma and then used to generate antibodies. ANP, which, as noted above, may be used as a targeting ligand, can be obtained from cultures of human aortic endothelial cells. ANP is generally localized in endothelium, but also may localize to the endothelial or myocardial tissue. ANP may be prepared, for example, using recombinant techniques, as well as by synthesis of the peptide using peptide synthesis techniques well known to one skilled in the art. It is also possible to use an antibody, either polyclonal or monoclonal, directed towards ANP. Similarly, a peptide directed to ANP may be used for targeting endothelial and/or myocardial cells. Both the β and α forms of atrial natriuretic factor may be used as targeting ligands for directing the present complexes to myocardial tissue.

Genetic Determinants

Genetic determinants represent one group of bioactive agents according to the definition thereof provided herein above. In certain embodiments of the invention genetic determinants may be present in complex with a lipophilic moiety or covalently coupled to a lipophilic moiety.

In aspects of the present invention that relate to gene therapy, the nucleic acid compositions contain either compensating genes or genes that encode therapeutic proteins. Examples of compensating genes include a gene which encodes dystrophin or a functional fragment, a gene to compensate for the defective gene in patients suffering from cystic fibrosis, a gene to compensate for the defective gene in patients suffering from ADA, and a gene encoding Factor VIII. Examples of genes encoding therapeutic proteins include genes which encodes erythropoietin, interferon, LDL receptor, GM-CSF, IL-2, IL-4 and TNF. Additionally, nucleic acid compositions which encode single chain antibody components which specifically bind to toxic substances can be administered. In some preferred embodiments, the dystrophin gene is provided as part of a mini-gene and used to treat individuals suffering from muscular dystrophy. In other preferred embodiments, a mini-gene which contains coding sequence for a partial dystrophin protein is provided. Dystrophin abnormalities are responsible for both the milder Beckers Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is wheelchair-bound by age 13 and usually dies by age 20. In some patients, particularly those suffering from BMD, partial dystrophin protein produced by expression of a mini-gene delivered according to the present invention can provide improved muscle function.

In some preferred embodiments, genes encoding IL-2, IL-4, interferon or TNF are delivered to tumor cells which are either present or removed and then reintroduced into an individual. In some embodiments, a gene encoding γ-interferon is administered to an individual suffering from multiple sclerosis.

Genetic determinants according to the invention may also be nucleic acids encoding part of or all of an apoptosis inducing protein. Apoptosis inducing proteins includes, but are not limited to BAX, BAD, bcl-xs, p53, and caspases (Sasaki et al. (2001), Nat. Biotechnol. 19, 543-547).

Furthermore, genetic determinants according to the invention may also be nucleic acids encoding part of or all of a protein, which may function as an immunemodulator. Examples of immunemodulators includes but are not limited to IL-2, IL-4, IL-5, IL-10, IL-12, IL15, INF-γ, TNF-β

In addition genetic determinants may also be nucleic acids encoding part of or all of an antigen presenting protein. Examples of antigen presenting proteins includes MHC class I and MHC class II molecules or fragments thereof capable of antigen presentation. Preferred MHC class I molecules are HLA-B7 and HLA-A2.

In one embodiment of the invention the genetic determinant may be an antisense nucleic acid (also designated antisense molecule) or a ribozyme.

Antisense molecules and ribozymes may also be delivered to the cells of an individual by introducing a nucleic acid composition which acts as a template for copies of such active agents. These agents inactivate or otherwise interfere with the expression of genes that encode proteins whose presence is undesirable. Nucleic acid compositions which contain sequences that encode antisense molecules can be used to inhibit or prevent production of proteins within cells. Thus, production of proteins such as oncogene products can be eliminated or reduced. Similarly, ribozymes can disrupt gene expression by selectively destroying messenger RNA before it is translated into protein. In some embodiments, cells are treated according to the invention using nucleic acid compositions that encode antisense or ribozymes as part of a therapeutic regimen which involves administration of other therapeutics and procedures. Nucleic acid compositions encoding antisense molecules and ribozymes use similar vectors as those which are used when protein production is desired except that the coding sequence does not contain a start codon to initiate translation of RNA into protein.

Ribozymes are catalytic RNAs which are capable of self-cleavage or cleavage of another RNA molecule. Several different types of ribozymes, such as hammerhead, hairpin, Tetrahymena group I intron, ahead, and RNase P are known in the art; see S. Edgington, Biotechnology (1992) 10, 256-262. Hammerhead ribozymes have a catalytic site which has been mapped to a core of less than 40 nucleotides Several ribozymes in plant viroids and satellite RNAs share a common secondary structure and certain conserved nucleotides. Although these ribozymes naturally serve as their own substrate, the enzyme domain can be targeted to another RNA substrate through base-pairing with sequences flanking the conserved cleavage site. This ability to custom design ribozymes has allowed them to be used for sequence-specific RNA cleavage; see G. Paolella et al., EMBO (1992), 1913-1919.) It will therefore be within the skill of one in the art to use different catalytic sequences from various types of ribozymes, such as the hammerhead catalytic sequence, and design them in the manner disclosed herein. Ribozymes can be designed against a variety of targets including pathogen nucleotide sequences and oncogenic sequences. Preferred embodiments include sufficient complementarity to specifically target the abl-bcr fusion transcript while maintaining efficiency of the cleavage reaction.

As an alternative to targeted antisense delivery, targeted ribozymes may be used. The term "ribozyme" refers to an RNA-based enzyme capable of targeting and cleaving particular base sequences in DNA and RNA. Ribozymes can either be targeted directly to cells, in the form of RNA oligonucleotides incorporating ribozyme sequences, or introduced into the cell as DNA encoding the desired ribozymal RNA. Ribozymes may be used and applied in much the same way as described for antisense nucleic acids.

Immunogenic Determinants and Antigenic Determinants

Immunogenic determinants and antigenic determinants represent bioactive agents according to the definition thereof provided herein above. In certain embodiments of the invention such determinants may be present in complex with a lipophilic moiety or covalently coupled to a lipophilic moiety.

The immune system may exhibit both specific and nonspecific immunity (Klein, J., et al., Immunology (2nd), Blackwell Science Inc., Boston (1997)). Generally, B and T lymphocytes, which display specific receptors on their cell surface for a given antigen, produce specific immunity. The immune system may respond to different antigens in two ways: 1) humoral-mediated immunity, which includes B cell stimulation and production of antibodies or immunoglobulins [other cells are also involved in the generation of an antibody response, e.g. antigen-presenting cells (APCs; including macrophages), and helper T cells (Th1 and Th2)], and 2) cell-mediated immunity (CMI), which generally involves T cells including cytotoxic T lymphocytes (CTLs), although other cells are also involved in the generation of a CTL response (e.g., Th1 and/or Th2 cells and APCs).

Nonspecific immunity encompasses various cells and mechanisms such as phagocytosis (the engulfing of foreign particles or antigens) by macrophages or granulocytes, and natural killer (NK) cell activity, among others.

Nonspecific immunity relies on mechanisms less evolutionarily advanced (e.g., phagocytosis, which is an important host defense mechanism) and does not display the acquired nature of specificity and memory, hallmarks of a specific immune response. Nonspecific immunity is more innate to vertebrate systems. In addition, cells involved in nonspecific immunity interact in important ways with B and T cells to produce an immune response.

The key differences between specific and nonspecific immunity are based upon B and T cell specificity. These cells predominantly acquire their responsiveness after activation with a specific antigen and have mechanisms to display memory in the event of future exposure to that specific antigen. As a result, vaccination (involving specificity and memory) is an effective protocol to protect against harmful pathogens.

As stated herein above, immunogenic determinants denote any substance capable of raising an immune response, including a specific antibody response. Any antigenic determinant is thus also an immunogenic determinant, but not all immunogenic determinants are antigenic determinants within the meaning of these terms as used herein.

In one embodiment of the invention an immunogenic determinant may be a genetic determinant encoding a substance capable of raising an immune response. Hence the immunogenic determinant may be a nucleic acid, such as DNA or RNA encoding a (poly)peptide, which in itself is an immunogenic determinant.

The complexes according to the invention may be used as carriers of bacterial immunogenic determinants and bacterial antigenic determinants from one or more bacteria. Such carriers may be employed as vaccines. Vaccines as used herein shall denote an immunogenic composition capable of raising a protective immune response. When it is desired to use for complexes according to the present invention as carriers of immunogenic determinants and/or antigenic determinants, the determinant in question is synthesized in vitro or isolated from a bacteria against which it is desirable to raise a protective immune response.

Bacteria for which vaccines can be formulated in accordance with the present invention include, but are not limited to: *Helicobacter pylori, Chlamydia pneumoniae, Chlamydia trachomatis, Ureaplasma urealyticum, Mycoplasma pneumoniae,* Staphylococcus spp., *Staphylococcus aureus,* Streptococcus spp., *Streptococcus pyogenes, Streptococcus pneumoniae, Streptococcus viridans, Enterococcus faecalis, Neisseria menirigitidis, Neisseria gonorrhoeae, Bacillus anthracis,* Salmonella spp., *Salmonella typhi, Vibrlo cholera, Pasteurella pestis, Pseudomonas aeruginosa,* Campylobacter spp., *Campylobacter jejuni,* Clostridium spp., *Clostridium difficile,* Mycobacterium spp., *Mycobacterium tuberculosis,* Treponema spp., Borrelia spp., *Borrelia burgdorferi,* Leptospira spp., *Hemophilus ducreyi, Corynebacterium diphtheria, Bordetella pertussis, Bordetella parapertussis, Bordetella bronchiseptica,* hemophilus influenza, *Escherichia coli,* Shigella spp., Erlichia spp., and Rickettsia spp.

Bacterial immunogenic determinants and antigenic determinants can be native, recombinant or synthetic. Such bacterial immunogenic determinants and/or antigenic determinants include, but are not limited to, selectins or lectins from bacteria that bind to carbohydrate determinants present on cell surfaces: and bacteria receptors for proteins, such as fibronectin, laminin, and collagens.

Vaccines of the present invention may also include one or more immunogenic determinants and/or antigenic determinants from a particular virus to form a vaccine. Viruses for which vaccines can be formulated include, but are not limited to: Influenza viruses, Parainfluenza viruses, Mumps virus, Adenoviruses, Respiratory syncytial virus, Epstein-Barr virus, Rhinoviruses, Polioviruses, Coxsackieviruses, Echoviruses, Rubeola virus, Rubella virus, Varicell-zoster virus, Herpes viruses (human and animal), Herpes simplex virus, Parvoviruses (human and animal), Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-1, HTLV-II, FeLV, Bovine LV, FeIV, Canine distemper virus, Canine contagious hepatitis virus, *Feline calicivirus, Feline rhinotracheitis* virus, TGE virus (swine), and Foot and mouth disease virus.

Viral Immunogenic determinants and/or antigenic determinants can be native, recombinant or synthetic. Such viral immunogenic determinants and/or antigenic determinants include, but are not limited to, viral proteins that are responsible for attachment to cell surface receptors to initiate the infection process, such as (i) envelope glycoproteins of retroviruses (HIV, HTLV, FeLV and others) and herpes viruses, and (ii) the neuramidase of influenza viruses. Additionally, peptides derived from such viral proteins can be employed, can be employed, either free, or associated non-covalently, or conjugated covalently to a suitable carrier.

Vaccines of the present invention may also include one or more tumor associated immunogenic determinants and/or antigenic determinants. Tumor associated immunogenic determinants and/or antigenic determinants can be native, recombinant or synthetic. Such tumor associated immunogenic determinants and/or antigenic determinants include, but are not limited to, killed tumor cells and lysates thereof, MAGE-1 or MAGE-3 and peptide fragments thereof, Human chorionic gonadotropin (HCG) and peptide fragments thereof, Carcinoembryonic antigen (CEA) and peptide fragments thereof, Alpha fetoprotein (AFP) and peptide fragments thereof, Pancreatic oncofetal antigen and peptide fragments thereof, MUC-1 and peptide fragments thereof, CA 125, 15-3, 19-9, 549, 195 and peptide fragments thereof, Prostate-specific antigens (PSA) and peptide fragments thereof, Prostaterspecific membrane antigen (PSMA) and peptide fragments thereof, Squamous cell carcinoma antigen (SCCA) and peptide fragments thereof, Ovarian cancer antigen (OCA) and peptide fragments thereof, Pancreas cancer associated antigen (PaA) and peptide fragments thereof, Her1/neu and peptide fragments thereof, gp-100 and peptide fragments thereof, mutant K-ras proteins and peptide fragments thereof, mutant p53 and peptide fragments thereof, truncated epidermal growth factor receptor (EGFR), and chimeric protein $p210_{BCR-ABL}$.

Peptides that are derived from these tumor associated immunogenic determinants and/or antigenic determinants can be employed, either free, or non-covalently associated, or conjugated covalently to a suitable carrier. Alternatively, gangliosides can be employed, either free, non-covalently associated or conjugated covalently to a suitable carrier; or oligosaccharide sequences that are specific or predominantly found in cancer cells can be employed either free, non-covalently associated or conjugated covalently to a suitable carrier.

In one particularly preferred embodiment, the present invention relates to complexes, wherein an antigenic determinant, such as e.g. a generally immune stimulating epitope against which it is desirable to raise a protective immune response, is comprised in the complex in combination with a polynucleotide, including DNA, such as e.g. plasmid DNA, encoding the same antigenic determinant, including an immune stimulating epitope.

In another preferred embodiment, the epitope forming part of the complex is presented as a combination of i) the epitope itself, and ii) an antigenic determinant comprising the epitope.

When the complexes are being used in a vaccine formulation, said formulation can comprise one or more adjuvants. The term "adjuvant" as used herein is any substance whose admixture with an injected immunogenic determinant modifies the immune response. Modification of the immune response means augmentation, intensification, or broadening the specificity of either or both antibody and cellular immune responses. Modification of the immune response can also mean decreasing or suppressing certain antigen-specific immune responses such as the induction of tolerance.

Such adjuvants may be any compound comprising an adjuvant effect known to the person skilled in the art. For example such adjuvants could be of mineral, bacterial, plant, synthetic or host origin or they could be oil in water emulsions.

Adjuvants could be selected from the group consisting of: $AIK(SO_4)_2$, $AINa(SO_4)_2$, $AINH_4 (SO_4)$, silica, alum, Al $(OH)_3$, $Ca_3 (PO_4)_2$, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'dipalmitoyi-sn-glycero-3-hydroxphosphoryloxy)-ethylamine (CGP 1 9835A, also referred to as MTP-PE), RIBI (MPL+TDM+CWS) in a 2% squalene/Tween-80.RTM. emulsion, lipopoly-saccharides and its various derivatives, including lipid A, Freund's Complete Adjuvant (FCA), Freund's Incomplete Adjuvants, Merck Adjuvant 65, polynucleotides (for example, poly IC and poly AU acids), wax D from *Mycobacterium, tuberculosis*, substances found in *Corynebacterium parvum, Bordetella pertussis*, and members of the genus Brucella, liposomes or other lipid emulsions, Titermax, ISCOMS, Quil A, ALUN (see U.S. Pat. Nos. 58,767 and 5,554,372), Lipid A derivatives, choleratoxin derivatives, Heat Shock Proteins (HSP, see e.g. Lehner et al. (2000), Eur. J. Immunol. 30, 594-603), HSP derivatives, LPS derivatives, synthetic peptide matrixes or GMDP, IL-1, IL-2, IL-5, IL-10, IL-12, IL-15; lipopeptides such as e.g. those disclosed by Bessler et al. 1982 (Hoppe Seylers Z. Physiol. Chem. 363, 767-770) and Bessler et al 1985 (J. Immunol., 135, 1900-1905); adjuvant active peptides and biomolecules, such as e.g. TGF-β and fragments thereof, including fragments disclosed in WO 01/72331.

In one embodiment of the present invention the vaccine formulation further comprises a carrier. The carrier may be present independently of an adjuvant. The function of a carrier can for example be to increase the molecular weight of the immunogenic determinant or the antigenic determinant in order to increase the activity or immunogenicity of the determinant, to confer stability to the determinant, to increase the biological activity of the determinant, or to increase its serum half-life. The carrier may be any suitable carrier known to the person skilled in the art, for example a protein. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diptheria toxoid are suitable carriers in one embodiment of the invention. Alternatively, the carrier may be dextrans for example sepharose. The carrier can be linked to the immunogenic determinant or the antigenic determinant by means of a labile linker such as e.g. a linker of the type disclosed in WO 97/49425.

The immunogenic determinant and/or the antigenic determinant may individually be administered more than once, such as twice, for example 3 to 5 times, such as 5 to 10 times, for example 10 to 20 times, such as 20 to 50 times. The incubation period between each administration may vary, but is usually within the range of 1 to 7 days, such as 1 to 4 weeks, for example 1 to 6 months, such as 6 to 12 months, for example 1 to 5 years, such as 5 to 15 years.

The individual may be any mammal, however preferably the individual is a human being.

Functional Homologues

Whenever a polypeptide, protein or nucleic acid is specifically mentioned herein by name, the name is meant to include said polypeptide, protein or nucleic acid per se as well as any functional homologue thereof. Hence, genetic determinants, immunogenic determinant, bioactive agent, antigenic determinants and medicament may for example be any of the specifically mentioned polypeptides, proteins or nucleic acids or any functional homologue thereof.

Functional homologues of polypeptides and proteins according to the present invention is meant to comprise any polypeptide sequence(s), which are capable of exerting the same or partly the same function.

Functional homologues according to the present invention comprise polypeptides with an amino acid sequence, which are sharing at least some homology with the predetermined polypeptide sequences as outlined herein above. For example such polypeptides are at least about 40 percent, such as at least about 50 percent homologous, for example at least about 60 percent homologous, such as at least about 70 percent homologous, for example at least about 75 percent homologous, such as at least about 80 percent homologous, for example at least about 85 percent homologous, such as at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with the predetermined polypeptide sequences as outlined herein above.

Homology may preferably be calculated by any suitable algorithm or by computerised implementations of such algorithms for example CLUSTAL in the PC/Gene program by Intelligenetics or GAP, BESTFIT, BLAST, FASTA and TFASTA in the Wisconsin Genetics Software Package, Genetics Computer Group (GCG). The homology between amino acid sequences may furthermore be calculated with the aid of well known matrices such as for example any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90. Functional homologues according to the present invention may comprise more than one such substitution, such as e.g. two amino acid substitutions, for example three or four amino acid substitutions, such as five or six amino acid substitutions, for example seven or eight amino acid substitutions, such as from 10 to 16 amino acid substitutions, for example from 15 to 25 amino acid substitution, such as from 25 to 30 amino acid substitutions, for example from 30 to 40 amino acid substitution, such as from 40 to 50 amino acid substitutions, for example from 50 to 75 amino acid substitution, such as from 75 to 100 amino acid substitutions, for example more than 100 amino acid substitutions.

The addition or deletion of an amino acid may be an addition or deletion of from 2 to 5 amino acids, such as from 5 to 10 amino acids, for example from 10 to 20 amino acids, such as from 20 to 50 amino acids. However, additions or deletions of more than 50 amino acids, such as additions from 50 to 200 amino acids, are also comprised within the present invention.

The polypeptides according to the present invention, including any variants and functional homologues thereof, may in one embodiment comprise more than 5 amino acid residues, such as more than 10 amino acid residues. for example more than 20 amino acid residues, such as more than 25 amino acid residues, for example more than 50 amino acid residues, such as more than 75 amino acid residues, for example more than 100 amino acid residues, such as more than 150 amino acid residues, for example more than 200 amino acid residues.

Homologues of nucleic acid sequences within the scope of the present invention are nucleic acid sequences, which encodes an RNA and/or a protein with similar biological function, and which is either at least 50% identical, such as at least 60% identical, for example at least 70% identical, such as at least 75% identical, for example at least 80% identical, such as at least 85% identical, for example at least 90% identical, such as at least 95% identical or able to hybridise to the complementary strand of said nucleic acid sequence under stringent conditions.

Stringent conditions as used herein shall denote stringency as normally applied in connection with Southern blotting and hybridisation as described e.g. by Southern E. M., 1975, J. Mol. Biol. 98:503-517. For such purposes it is routine practise to include steps of prehybridization and hybridization. Such steps are normally performed using solutions containing 6×SSPE, 5% Denhardt's, 0.5% SDS, 50% formamide, 100 μg/ml denatured salmon testis DNA (incubation for 18 hrs at 42° C.), followed by washings with 2×SSC and 0-5% SDS (at room temperature and at 37° C.), and a washing with 0.1×SSC and 0.5% SDS (incubation at 68° C. for 30 min), as described by Sambrook et al., 1989, in "Molecular Cloning/A Laboratory Manual", Cold Spring Harbor), which is incorporated herein by reference.

Homologous of nucleic acid sequences also encompass nucleic acid sequences which comprise additions and/or deletions. Such additions and/or deletions may be internal or at the end. Additions and/or deletions may be of 1-5 nucleotides, such as 5 to 10 nucleotide, for example 10 to 50 nucleotides, such as 50 to 100 nucleotides, for example at least 100 nucleotides.

Methods for Treatment of a Patient

In accordance with the present invention there is also provided a method of conferring a broad based protective immune response against hyperproliferating cells that are characteristic of hyperproliferative diseases, as well as a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a nucleic acid composition that includes a nucleotide sequence which encodes an immunogenic "hyperproliferating cell"-associated protein into the cells of an individual, results in the production of those proteins in the vaccinated cells of an individual. As used herein, the term "hyperproliferative-associated protein" is meant to refer to proteins that are associated with a hyperproliferative disease. To immunize against hyperproliferative diseases, a nucleic acid composition that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Other tumor-associated proteins can be used as target proteins, such as proteins which are found at higher levels in tumor cells, including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and biotechnology, as well as epidemiology, allow for the determination of probability and risk assessment for the development of cancer in an individual. Using genetic screening and/or family health histories, it is possible to predict the probability that a particular individual has for developing any one of several types of cancer.

Similarly, those individuals who have already developed cancer and who have been treated to remove the cancer, or are otherwise in remission, are particularly susceptible to relapse and reoccurrence. As part of a treatment regimen, such individuals can be immunized against the cancer that they have been diagnosed as having had in order to combat such a recurrence. Thus, once it is known that individuals have had a type of cancer and are at risk of a relapse, they can be immunized in order to prepare their immune systems to combat any future appearance of the cancer.

The present invention also provides a method of treating individuals suffering from hyperproliferative diseases. In such methods, the introduction of nucleic acid compositions serves as an immunotherapeutic, directing and promoting the immune system of the individual to combat hyperproliferative cells that produce the target protein.

The present invention also provides a method of treating individuals suffering from autoimmune diseases and disorders by conferring a broad based protective immune response against targets that are associated with autoimmunity, including cell receptors and cells which produce "self"-directed antibodies.

T cell mediated autoimmune diseases include Rheumatoid arthritis (RA), multiple sclerosis (MS), Sjogren's syndrome, sarcoldosis, insulin dependent diabetes mellitus (IDDM), autoimmune thyroiditis, reactive arthritis, ankylosing spondylitis, scleroderma, polymyositis, dermatomyositis, psoriasis, vasculitis, Wegeners granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ14, Vβ-17 and Vβ17. Thus, vaccination with a nucleic add composition that encodes at least one of these proteins will elicit an immune response that will target T cells involved in RA. See: Howell, M. D., et al., 1991 Proc. Natl. Acad. Sci. USA 88:10921-10925; Paliard, X., et al., 1991 Science 253:325-329; Williams, W. V., et al., 1992 J. Clin. Invest. 90:326-333; each of which is incorporated herein by reference.

In MS, several specific variable regions of TCRs which are involved in the disease have been characterized. These TCRs include Vβ-7 and Vβ-10. Thus, vaccination with a nucleic acid composition that encodes at least one of these proteins will elicit an immune response that will target T cells involved in MS. See: Wucherpfennig, K. W., et al., 1990 Science 248: 1016-1019; Oksenberg, J. R., et al., 1990 Nature 345:344-346; each of which is incorporated herein by reference.

In scleroderma, several specific variable regions of TCRs which are involved in the disease have been characterized. These TCRs include Vβ-6, Vβ-8, Vβ-14 and Vα-16, Vα-3C, Vcα7, Vα-14, Vα-15, Vα-16, Vα-28 and Vα-12. Thus, vaccination with a nucleic acid composition that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of such antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes nucleic acid compositions that encode the variable region Of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 Sequence of Proteins of Immunological Interest U.S. Department of Health and Human Services, Bethesda Md., which is incorporated herein by reference. In addition, a general method for cloning functional variable regions from antibodies can be found in Chaudhary, V. K., et al., 1990 Proc. Natl. Acad. Sci. USA 87-1066, which is incorporated herein by reference.

Medicaments

The complexes according to the present invention are used in one preferred embodiment for promoting the uptake across mucosal membranes and skin surfaces of any one of a large number of medicaments and pharmaceutically active substances. Preferably, such pharmaceutically active substances are polynucleotides or polypeptides. However, pharmaceutical compositions comprising the complexes according to the present invention-can he used to increase the uptake of any pharmaceutically active substance, so long as is molecular weight is less than about 250,000 daltons.

Examples of polypeptides that can be administered together with the pharmaceutical compositions of the present invention include, but are not limited to, insulin, insulin-like growth factor, growth hormone, parathyroid hormone, renin, prolactin, thyroid stimulating hormone, corticotropin, follicle stimulating hormone, chorionic gonadotropin, luteinizing hormone, luteinizing releasing factor, interferon (alpha, beta, and gamma), lymphokines, interleukin, tumor necrosis factor, antibodies (monoclonal and polyclonal), e.g. IgG, enkephalins (see Su, K. S. E., et al., J. Pharm. Scd. 74:394-98 (1985)), calcitonin (McMartin, C. and Peters, G., Delivery Systems For Peptide Drugs, S. S. Davis et al. (eds.), pp. 249-53, Plenum Press New York (1986)), somatostatin (Mc-Martin, C. and Peters, G., Delivery Systems For Peptide Drugs, Davis, S. S., et al. (eds.), pp. 255-63, Plenum Press New York (1986)), methionyl growth hormone (Moore, J. A. et al., Delivery Systems For Peptide Drugs, Davis, S. S., et al. (eds.), pp. 317-329, Plenum Press New York (1986)), oxytocin (Hendricks, C. H. and Pose, S. V., J. A. M. A. 175:384-387 (1961)), vasopressin and desmopressin (Richson, D. W. and Robinson, A. G., Ann Int. Med. 103;228-239 (1985)), luteinizing hormone releasing hormone (Fink, G. et al., J. Endocr. 63:351-360 (1974)), nafarelin acetate (Anik, S. T. et al., J. Pharm. Sci. 73:684-685 (1984), secretin (Ohwaki, T. et al., J. Pharm. Sci. 74(5):550-552 (May, 1985)), glucagon (Pontiroli, A. E. et al., Acta Diabetol Let. 22:102-110 (1985)), pimolol (Kaila, T. et al., J. Ocular Pharm. 1:79-83 (1985)), thyrotropin-releasing hormone (Sandow, J. and Petri, W., Trans Nas. System. Med., (Chien,Y. W. ed.) Elsevier Science Publishers B.B., Amsterdam, pp. 183-199 (1985)).

In addition, the compositions of the present invention can also be employed to increase the uptake across mucosal membranes and skin surfaces of enzymes, transferases, hydrolases, isomerases, proteases, ligases and oxidoreductases such as e.g. esterases, phosphatases, glycosidases and peptidases; enzyme inhibitors such as leupeptin, chymostatin and pepslatin and growth factors, such as tumor angiogenesis factor.

Other suitable pharmaceutically active substances are fat-soluble steroids such as progesterone, estrogens and androgens, as well as the fat soluble vitamins A, D, E and K.

In addition to low and high molecular weight polypeptides, the pharmaceutically active substance can be an anti-inflammatory agent (e.g., indomethacin, flurbiprofen, ketoprofen, ibuprofen phenylbutazone), antibiotics (e.g., beta-lactams, aminoglycosides, macrolides, tetracyclines, pryridonecarboxylic acids, phosphomycin), anti-tumor agents (e.g., adriamycin, cisplatin, bleomycin, mitomycin, fluorouracil, vinblastine, vincristine), amino acids (e.g., ascorbic acid, N-acetyltryptophan), antifungal agents, prostaglandins, vitamins, steroids, vaccine antigens, vaccine adjuvants, and antiviral agents (AZT, DDI, acyclovir, idoxuridine, amantadine, and vidarabine).

The medicaments capable of being administered in combination with the complexes according to the present invention may be administered either prophylactically, therapeutically, or in connection with a diagnostic method carried out on the human or animal body. The complexes may also comprise a cosmetic agent used for a cosmetic method of treatment of a human or any other animal.

The compositions comprising the complexes according to the invention in combination with a medicament may further comprise a biodegradable microsphere encapsulating the complexes and the medicament. The biodegradable microsphere may comprise any suitable targeting ligand capable of guiding or targeting the microsphere to any desired location.

Preferred medicaments for rectal administration include hormones, antibiotics, anaesthetics, analgesics, anti-fungal compounds, bactericides, bacteriostats, anti-protozoan compounds, and anti-viral compounds.

Examples of medicaments capable of being released from a pharmalogical composition according to the invention and into a human or animal body include, but are not limited to, antihistamines (e.g., dimenhydrinate, diphenhydramine (50-100 mg), chlorpheniramine and dexchlorpheniramine maleate), analgesics (e.g., aspirin, codeine, morphine (15-300 mg), dihydromorphone, oxycodone, etc.), anti-inflammatory agents (e.g., naproxyn, diciofenac, indomethacin, ibuprofen, acetaminophen, aspirin, sulindac), gastro-intestinals . and anti-emetics (e.g., metoclopramide (25-100 mg)), anti-epileptics (e.g., phenytoin, meprobamate and nitrazepam), vasodilators (e.g., nifedipine, papaverine, diltiazem and nicardipine), anti-tussive agents and expectorants (e.g., codeine phosphate), anti-asthmatics (e.g. theophylline), anti-spasmodics (e.g. atropine, scopolamine), hormones (e.g., insulin, heparin), diuretics (e.g., ethacrynic acid, bendroflumethiazide), anti-hypotensives (e.g., propranolol, clonidine), bronchodilators (e.g., albuterol), anti-inflammatory steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, antacids, vitamins, stimulants (including apetite suppressants such as phenylpropanolamine). The above list is not meant to be exclusive.

Other types of medicaments include flurazepam, nimetazepam, nitrazepam, perlapine, estazolam, haloxazolam, sodium valproate, sodium cromoglycate, primidone, alclofenac, perisoxal citrate, clidanac, indomethacin, sulpyrine, flufenamic acid, ketoprofen, sulindac, metiazinic acid, tolmetin sodium, fentiazac, naproxen, fenbufen, protizinic acid, pranoprofen, flurbiprofen, diclofenac sodium, mefenamic acid, ibuprofen, aspirin, dextran sulfate, carindacillin sodium, and the like.

The medicament may be in the form of a physiologically active polypeptide, which is selected from the group consisting of insulin, somatostatin, somatostatin derivatives, growth hormone, prolactin, adrenocorticotrophic hormone, melanocyte stimulating hormone, thyrotropin releasing hormone, its salts or its derivatives, thyroid stimulating honnone, luteinizing hormone, follicle stimulating hormone, vasopressin, vasopressin derivatives, oxytocin, carcitonin, parathyroid hormone, glucagon, gastrin, secretin, pancreozymin, cholecystokinin, angiotensin, human placental lactogen, human chorionic gonadotropin, enkephalin, enkephalin derivatives, endorphin, interferon (in one or more of the forms alpha, beta, and gamma), urokinase, kallikrein, thymopoietin, thymosin, motilin, dynorphin, bombesin, neurotensin, caerulein, bradykinin, substance P, kyotorphin, nerve growth factor, polymyxin B, colistin, gramicidin, bacitracin, bleomycin and neocarzinostatin. Furthermore, the medicament may be a polysaccharide, such as heparin, an antitumor agent such as lentinan, zymosan and PS-K (krestin), an aminoglycoside such as e.g. gentamycin, streptomycin, kanamycin, dibekacin, paromomycin, kanendomycin, lipidomycin, tobramycin, amikacin, fradiomycin and sisomicin, a beta-lactam antibiotic, such as e.g. a penicillin, such as e.g. sulbenicillin, mecillinam, carbenicllin, piperacillin and ticarcillin, thienamycin, and cephalosponns such as cefotiam, cefsulodine, cefmenoxime, cefmetazole, cefazolin, cefotaxime, cefoperazone, ceflizoxime and moxalactam, or a nucleic acid drug such as e.g. citicoline and similar antitumor agents, for example cytarabine and 5-FU (5-fluorouracil).

Medicaments suitable for vaginal administration are contraceptives, hormones, antibiotics, anaesthetics, analgesics, contraction-preventers, anti-mycotica, bactericides, bacteriostats, anti-protozoan compounds, anti-viral compounds, and compositions for uterus contraction. Other suitable medicaments may be dermatological medicaments such as antimycotica, antipruritc compositions, and dermoprotective compositions.

Medicaments for administration in the ear (otogenic administration) are e.g. antibiotics, corticosteroids, local anaesthetics, and analgesics.

Medicaments for nasal administration are e.g. haemostatica, anti-allergenic compounds, antihistamines, anticholinergica, adrenergic (detumescent) compounds, and local analgesics.

The medicaments can in principle have either local effects, or systemic effects. In a preferred embodiment the pharmaceutical composition according to the invention comprises at least one medicament that has a local effect and essentially does not have any systemic effects.

Pharmaceutical Compositions

The pharmaceutical compositions of the present invention can be applied to any mucous membrane Including the conjunctiva, nasopharynx, orthopharnyx, vagina, colon, urethra, urinary bladder, lung, large (rectal) and small (enteral) intestine. The compositions of the present invention can also be administered transdermally, for example, as part of a patch. Preferably, the compositions of the present invention are administered to the eye as part of eye drops, nasally as part of an aerosol or buccally as part of a solid wafer.

Accordingly, any state of the art method can be used for delivery to an individual of the complexes or the pharmaceutical compositions comprising the complexes according to the invention. Examples include, but are not limited to i) associating the complexes or the pharmaceutical compositions comprising the complexes with a cationic liposome, ii) covalently linking the complexes or the pharmaceutical compositions comprising the complexes to a transfection agent, and iii) coating minute gold particles with the complexes or the pharmaceutical compositions comprising the complexes and using the coated particles for a bio-ballistic transfer.

In addition, the pharmaceutical compositions of the present invention can also be formulated in sustained release compositions. For example, the sterol and/or saponin component of the complex and the drug can be combined with a silicone elastomer that releases the complex and drug over a long period of time. The silicone elastomer can also comprise albumin. See U.S. Pat. No. 4,985,253, the contents of which are fully incorporated by reference herein. The release rate of the drug from the silicone elastomer can be controlled by incorporation of a water soluble or fat soluble mixing agent or cosolvent (e.g., polyethylene glycol 400, polysorbate 80, sodium alginate, L-alanine, sodium chloride; polydimethylsiloxane) into the silicone elastomer. Any other additive can also be incorporated into the silicone elastomer for the purpose of accelerating the release rate.

In addition, the pharmaceutically active substance and the complexes according to the invention can be formulated in a controlled release composition comprising a polylactide and/or polyglycolide copolymer, a cellulose polymer (methyl-, methylhy-droxyethyl-, hydroxypropyl-, hydroxyethyl-, sodium carboxyethyl-cellulose), polyacrylic acid, polymethylmethacrylate, cross-linked polyacrylic acid, polyvinylpyrrolidone, polyvinylalcohol, polyethylene glycol, agarose or a copolymer of styrene and hydroxyethylmethacylate crosslinked with divinylazobenzene.

Alternatively, the pharmaceutically active substance and the complexes according to the invention can be formulated as part of a DEAE-dextran microsphere, a starch microspheres, an albumin microspheres, or any other microsphere or microcapsule made from any pharmaceutically acceptable material.

Likewise the microsphere may be provided with a coating. This coating may be of a kind that prevents agglomeration or sticking of the microspheres or prevents evaporation of the drug and/or a solvent comprising the drug inside the microsphere. The invention also foresees the use of coatings providing the microsphere with an affinity for specific cells or tissues. Such an affinity-coating may be in the form of specific amino-acid sequences or even anti-bodies or parts of antibodies having an affinity for specific proteins. Thereby the drug-delivery can be targeted to exactly those cells (e.g. cancer cells, metastases) to which the drug should be administered. Likewise this makes it possible to use the microspheres for diagnostic use and the drug could in such cases be substituted by a compound suitable for labelling the targeted cells.

Agents for encapsulation include but are not limited to coilloids, hydrocolloids such as gelatine, exudates such as gum arabic, tragacanth, gum karya, gum ghatti; extracts from seaweed such as agar, alginate, carrageenan and furcellaran; extracts from plants such as pectin and arabinogalactan; extracts from marine and terrestrial animals such as gelatines and other proteinaceous hydrocolloids; flours from seeds such as guar, locust bean, soya bean; proteins from seeds such as soya bean proteins; flours from cereals such as starches and microcrystalline cellulose, biosynthetic or fermentation derived hydrocolloids such as dextran, xanthan and curdlan; chemically modified hydrocolloids such as cellulose derivatives, including methyl cellulose and other derivatives, including modified starches and low methoxyl pectin; synthetic hydrocolloids such as polyvinylpyrrolidone, carboxyvinyl polmers etc.

According to one embodiment of the invention, the microspheres contain a hydrophobic/aerophilic solid material having a maximum average particle size not exceeding 10 μm (micrometer) and which can be dispersed in water in the form of discrete microparticles, wherein the amount of solid active material in the microencapsulated product is from 22 to 71% by weight.

According to another embodiment of the invention, the microspheres may comprise a microencapsulated oil or fat product, wherein at least one oil or fat is dispersed in the matrix material as particles or drops having an average diameter of less than or equal to 2 μm (micrometer), the oil or fat containing at least 10% by weight of highly unsaturated fatty acid, preferably omega-3 and omega-6 fatty acids, the level of free fatty acids being below 5.0% by weight and preferably below about 0.5% by weight, and the matrix material consisting of caseinate and optionally at least one carbohydrate. The oil or fat may be a marine oil, preferably a fish oil, containing at least 30% by weight of omega-3 fatty acids. Similarly, the oil or fat may be a vegetable oil, preferably borage oil, and preferably containing at least 20%. by weight of omega-3 and/or omega-6 fatty acids. This oil or fat may be a natural, fermented and/or enzymatically reesterified or chemically modified oil or fat, preferably in an amount of from 10 to 65% by weight; the matrix material comprises from 1 to 100% by weight caseinate and from 0 to 70% by weight of at least one carbohydrate selected from the group consisting of glucose syrup, maltodextrin, saccharose, maltose or lactose: from 0 to 10% by weight of at least one antioxidant selected from the group consisting of the vitamin antioxidants a-, ss-, r- and 6-tocopherols, ascorbic acid and derivatives thereof, carotenolds, and rosemary extract, and from 0 to 35% by weight of a spraying agent selected from the group consisting of corn starch, milk proteins, including casein, caseinate and whey proteins, preboiled or gelatinised starch, soy bean protein isolates, lactose, tricalcium phosphate, and calcium carbonate.

In the case of a water-soluble drug, the microsphere may be prepared as a two-phase system with an inner aqueous phase comprising the drug and optionally drug-retaining or drug-stabilising compounds. This inner aqueous phase can then be emulsified with an oil-phase comprising a polymer to create a water/oil emulsion.

The polymer to be contained in the oil phase in carrying out the microencapsulation method is a polymer, which is scarcely soluble or insoluble in water and is biocompatible. Examples are such biodegradable polymers as aliphatic polymers (e.g. polylactic acid, polyglycolic acid, polycitric acid, polymalic acid), poly-alpha-cyanoacrylic acid esters, poly-beta-hydroxybutyric acid, polyalkylene oxalate (e.g. polytrimethylene oxalate, polytetramethylene oxalate), polyorthoesters, polyorthocarbonates and other polycarbonates (e.g. polyethylene carbonate, polyethylenepropylene carbonate), and polyamino acids (e.g. poly-γ-benzyl-L-glutamic acid, poly-L-alaine, poly-gamma-methyl-L-glutamic acid). Other biocompatible high polymers are polystyrene, polyacrylic acid, polymethacrylic acid, acrylic acid-methacrylic acid copolymers, polyamides (nylon), polyethylene terephthalate (tetron), polyamino acids, silicone polymers, dextran stearate, ethylcellulose, acetyl-cellulose, nitrocellulose, polyurethanes, maleic anhydride-based copolymers, ethylene-vinyl acetate copolymers, polyvinyl acetate, polyvinyl alcohol, polyacrylamide, etc. These polymers may be homopolymers or copolymers of two or more monomers, or mixtures of the polymers. They may also be in the salt form.

For the emulsification procedure, a known method of effecting dispersion is used. Said method is, for example, the intermittent shaking method, the mixer method using a propeller-shaped stirrer, a turbine-shaped stirrer or the like, the colloid mill method, the hornogeniser method or the ultrasonication method.

The thus-prepared W/O emulsion is then emulsified into a W/O/W triplicate-phase emulsion and subjected to an in-water drying. Thus, said W/O emulsion is further added to a third aqueous phase to give a W/O/W emulsion and thereafter the solvent in the oil phase is removed to give microspheres.

To the external aqueous phase, there may be added an emulsifying agent. As the emulsifying agent, there may be used any one capable of forming generally a stable O/W emulsion, for example an anionic surfactant (e.g. sodium oleate, sodium stearate, sodium lauryl sulfate), a nonionic surfactant [e.g. polyoxyethylenesorbitan fatty acid ester (Tween 80, Tween 60, products of Atlas Powder Co., U.S.A.), a polyoxyethylene castor oil derivative (HCO-60, HCO-50, products of Nikko Chemicals, Japan)), polyvinyl pyrrolidone, polyvinyl alcohol, carboxymethylcellulose, lecithin or gelatin. Such emulsifiers may be used either alone or in any combination.

When the the complexes according to the invention and pharmaceutically active substance are formulated in a sustained release composition, the content of the pharmaceutical substance can be appropriately controlled depending upon the dose to be administered and the release rate. When the composition is shaped in matrix type preparation, the content of the pharmaceutical substance can usually be from 5 to 40% by weight and, more preferably, not more than 15% by weight, for example, 9% by weight or less. When administering a peptide hormone, its content should be no more than about 6 to 10% by weight. Albumin, if employed, is present at not more than 50% by weight, preferably from about 20 to 30% by weight. The silicone elastomer can be contained in an amount of not less than 50% by weight, preferably from 70 to 90% by weight.

The sustained release compositions can be prepared by mixing the components in any optional order. When albumin is added, the drug and albumin are first combined, preferably in a solid state. Alternatively, an aqueous solution of the pharmaceutical substance and albumin can be mixed and the resulting mixture lyophilized to make a solid mixture. This mixture is then dispersed uniformly with an elastomer base, optionally, with a plasticizer (e.g., dimethylpolysiloxane), adding a curing agent thereto and stirring the resultant mixture. The mixture is then placed in an appropriate mold and cured at room temperature to give a shaped composition. In the alternative, a core material not containing a pharmaceutical substance can be covered with the composition comprising a silicone elastomer containing a pharmaceutical substance, optionally containing albumin, to make a shaped composition. Such core material can comprise any non-toxic material. Preferably, such core material is an elastic polymer.

The sustained release compositions of the present invention can have any shape that is suitable for effective contact with mucous membranes in body cavities. For example, when the pharmaceutically active substance is administered buccally, the sustained release composition can be in the form of a wafer. When the pharmaceutically active substance is administered vaginally, the sustained release composition can be in the form of a ring. When administered ocularly, the sustained release composition can be in the form of thin ocular implants.

The compositions of the present invention can also be formulated as part of a chewing gum comprising the gum from the latex of the sapodilla. Preferably, the chewing gum composition also comprises sweeteners (sugar, aspartame and the like) and flavorants (spearmint, wintergreen or peppermint oil and the like) that mask any unpleasant taste associated with the pharmaceutically active substance.

When administered ocularly or nasally, the compositions of the present invention can be formulated in an aqueous solution buffered to a pH of between 3.0 and 8.0, most preferably pH 5.0-5.4, by means of a pharmaceutically acceptable buffer system. Any pharmaceutically acceptable buffering system capable of maintaining the pH in the preferred ranges can be used in the practice of this invention. A typical buffer will be, for example, an acetate buffer, a phosphate buffer, a citrate buffer, a succinate buffer, or the like. The concentration of buffer can range from between 0.005 and 0.1 molar, most preferably about 0.02 molar.

When the compositions of the present invention are administered ocularly, the composition can comprise a solution containing sodium, potassium, magnesium, calcium, chloride and bicarbonate ions as well as dextrose and glutathione. See, for example, U.S. Pat. Nos. 4,550,022 and 4,443,432.

Alternatively, the ocular fluid can comprise an aqueous solution containing sodium chloride, potassium chloride, calcium chloride and N-2-hydroxyethylpiperazine-N-2-ethanesulphonic acid. Sodium hydroxide can be included to establish a pH value of about 7.25 and magnesium sulfate can also be included. See UK Patent Application GB 2,064,320. See also U.S. Pat. No. 4,938,970, which discloses irrigation solutions that do not cause pain when administered to the eye. According to this patent, the electrolyte solution comprises 2-10 meq/L of $K^+$, 0-3 meq/L of $Ca^{++}$, 1-5 meq/L of $Mg^{++}$ and 110-150 meq/L of $Na^{++}$, buffered to a pH of 6.85-8.0.

Other materials, such as preservatives, salts to achieve the tonic value of tissue, or other additives indicated by known nasal or ocular formulation chemistry, can be added to these formulations.

By the term "animal" is intended all animals that might derive a benefit from the compositions of this invention. Foremost among such animals are humans: however, the invention is not intended to be so limited, it being within the contemplation of the invention to treat any and all such animals that can experience the beneficial effects of the present invention.

For nasal administration, the compositions of the invention will preferably be in a container provided with means for enabling application of the contained composition to the nasal mucosa, e.g., with a nasal applicator device. Suitable applicators are known in the art and include those adapted for administration of liquid compositions to the nasal mucosa in drop or spray form. Since dosing with polypeptides should be as accurately controlled as possible, the use of spray applicators for which the administered quantity is susceptible to precise regulation is generally preferred.

Suitable administrators include e.g., atmosing devices, e.g., pop-atomizers and aerosol dispensers. In the tatter case, the applicator will contain the composition of the present invention together with a propellant medium suitable for use in a nasal applicator. The atomizing device will be provided with an appropriate spray adaptor allowing delivery of the contained composition to the nasal mucosa. Such devices are well known in the art.

The container, e.g. nasal applicator or eye drop bottle, can contain sufficient composition for a single nasal or ocular dosing or for several sequential dosages, e.g. over a period of days or weeks.

Kit-of-parts

In many aspects the present invention relates to complexes, wherein said complexes further comprises for example a genetic determinant and/or an immunogenic determinant. However, in one embodiment the present invention relates to any of the above described complexes, wherein said complex have been admixed with, but is not complexed with one or more selected from the group consisting of bioactive agents, immunogenic determinants, genetic determinants, enzymes, adjuvants and adjuvant active peptides and biomolecules, and medicaments.

In another embodiment the present invention relates to a kit-of-parts, wherein said kit-of-parts comprises a complex according to the invention and one or more selected from the group consisting of bioactive agents, immunogenic determinants, genetic determinants, enzymes, adjuvants and medicaments.

In one embodiment the present invention relates to a kit-of-parts comprising a) any of complexes described herein above; and b) an immunogenic determinant; and/or c) an antigenic determinant; and wherein the immunogenic determinant is different from the antigenic determinant.

In particular such as kit-of-part may be used for a prime-boost immunisation. Hence the immunogenic determinant may be administered to an individual in need thereof and after an incubation period the antigenic determinant may be administered to said individual. Alternatively, the antigenic determinant may be administered to an individual in need thereof and after an incubation period the immunogenic determinant may be administered to said individual.

It is preferred that the immunogenic determinant comprises or encodes at least one epitope, which is also comprised within the antigenic determinant.

The immunogenic determinant may be any of the immunogenic determinants described herein above. For example the immunogenic determinant may be a genetic determinant encoding a product capable of raising an immune response. In one preferred embodiment, the immunogenic determinant comprises or essentially consists of a polynucleotide. Said polynucleotide preferably encodes an epitope, which is comprised within the antigenic determinant.

The immunogenic determinant may be present isolated or as part of a complex according to the invention or admixed with a vaccine formulation. Hence, for example a complex within the kit-of-parts may comprise said immunogenic determinant.

The antigenic determinant may be any of the antigenic determinant described herein above. In one preferred embodiment however, the antigenic determinant comprises or essentially consists of a polypeptide. For example the antigenic determinant may be a lipopeptide, such as any of the lipopeptides described in Nardelli et al. (1994), Vaccine 12, 1335-1339; Tam et al. (1998), Dev. Biol. Stand., 92, 109-116, Beekman et al. (1997), J. Pept. Res. 50, 357-364; Beekman et al (1999), Vaccine 17, 2043-2050; Bessler et al. (1997), Behring Inst. Mitt., 390-399; Bessler et al. (1997), Int. J. Immunopharmacol., 19, 547-550, Deres et al. (1989), Nature 342, 561-564, Hoffmann et al. (1989), Biol. Cham, Hoppe Seyler, 370, 575-582; Schild et al. (1991), Eur. J. Immunol., 21, 2649-2654; Schlecht et al. (1993), Naturwissenschaften, 80, 9-17. Said polypeptide preferably comprises an epitope, which is also comprised within or encoded by the immunogenic determinant.

The antigenic determinant may be present isolated or as part of a complex according to the invention or mixed into a vaccine formulation Hence, for example a complex within the kit-of-parts may comprise said antigenic determinant.

EXAMPLES

The following examples are merely illustratative of preferred embodiments of the invention and should not be interpreted in any way that is limiting the invention to what is disclosed in the examples.

Example 1

Incorporation of Low-molecular Weight Substances into ISCOMs

Immune stimulating complexes (ISCOMs) are cage-like structures of uniform size with a diameter of approximate 40 nm. In general, the term ISCOM is used when antigen is inserted into the structures, whereas ISCOM-matrix denotes structures without antigen. Several reports describe the formation of ISCOMs with amphipathic proteins like virus membrane proteins. But also, non-amphipatic proteins like BSA and OVA as well as hydrophilic proteins linked to fatty acids have been used. Two crucial components for the formation of ISCOMs are cholesterol and phospholipid that are solubilized by detergent. Many protein antigens can be brought into solution by detergents compatible with the process of ISCOM-formation whereas other compounds like lipopeptides require different solvents. The methods reported here allow the embedment of such lipopeptides into the structures of ISCOMs by employing a pre-dissolution step in organic solvent (N,N'-dimethylsulfoxide) followed by stepwise dilution with detergent:water. By the use of different solvents miscible with water (dimethylformamide, ethanol) other low molecular weight compounds can be inserted into ISCOMs. This is demonstrated for the fluorescent dye DiI. The influence of organic solvents for the formation of intact ISCOM structures was also investigated. For the three solvents tested (dimethylsulfoxide, dimethylformamide, ethanol) the maximum allowable concentration during the creation of ISCOMs was between 15%-25%. All preparations of ISCOMs were done in the presence Mega 10, a detergent with high critical micelle concentration. To investigate if Mega 10 remained a constituent part of ISCOM-matrix after dialysis radiolabeled Mega 10 was added during the preparation. Dialysis efficiently removed the detergent and only a negligible amount remained associated with the ISCOM-matrix.

Introduction

Immune stimulating complexes or ISCOMs were discovered when the adjuvant Quil A was combined with viral proteins in the presence of lipids. These cage-like microstructures are as the name indicates generally employed in immunization experiments, but may also be of use in non-immunological applications due to their characteristic properties ISCOMs are stable rigid structures that can be stored in aqueous solutions, frozen or lyophilized. The internal environment of ISCOMs is different from the surrounding liquid phase, as small water-soluble molecules cannot be retained [1]. ISCOMs are soluble in water and can as such be used to carry hydrophobic molecules (e.g. antigens) in aqueous solutions. One of the biological properties of ISCOMs is their ability to penetrate cell membranes allowing embedded molecules to access the interior of cells. This ability is probably due to their hydrophobic structure and their content of Quil A, a saponin that complexes cholesterol membranes. Quil A is as such surface-active and hemolytic and may have adverse effects when applied in vivo. Upon formulation of Quil A into ISCOMs the hemolytic property is partly inhibited lowering this undesired effect. The fate of ISCOMs in cells has not been reveled in details, although a substantial part of ISCOM-borne antigen has been demonstrated in the cytosol of both phagocytic and non-phagocytic antigen-presenting cells (e.g. macrophages, dendritic cells and B-cells) [2]. Other reports describe the finding intact and partially degraded ISCOMs within the phagosomes of macrophages in close association with the phagosomal membranes [3].

Many proteins (antigens) can be inserted into the ISCOM-structure by mixing of Quil A, cholesterol and phospholipid (phosphatidylcholine) with the protein of interest. During the formation of the ISCOMs protein is entrapped and are stably embedded. This approach is often efficient for amphipathic proteins like membrane-spanning glycoproteins, and hydrophilic proteins chemically modified by the coupling of fatty acids (e.g. palmitification). However, some hydrophilic proteins like bovine serum albumin and ovalbumin reveal hydrophobic regions by treatment at low pH enabling insertion without chemical modification [4;5]. Other substances can be linked to the preformed structures (ISCOMs or ISCOM-matrix) using bifunctional reagents. Substituting phosphadityl-choline with phosphadityl ethanolamine during the formation of ISCOMs facilitate chemical modification by supplying reactive amino groups. However both the incorporation method and the chemical linking method requires the compounds to be soluble in water:detergent. This requirement limits the variety of substances embeddable. Compounds that do not directly dissolve in aqueous solutions may show soluble in mixtures of organic solvent, water and detergent. In this report we investigate if ISCOMs can be formed in mixtures of water and different polar organic solvents and at what concentrations. The three solvents of interest are N,N'-dimethylsulfoxide (DMSO), dimethylformamide (DMF) and ethanol (EtOH), all of which are mixable with water at all concentrations. Also, we address if the use of these solvents render new compounds possible for insertion into ISCOMs. The examples are a synthetic lipopeptide and the fluorescent lipophilic tracer Dil.

It is generally assumed that ISCOMs prepared by the use of a detergent with high CMC (critical micelle concentration) can be purified by dialysis. The dialysis step removes low molecular weight components not incorporated into the ISCOM-structures. However, it has not been investigated if the detergent forms part of the ISCOMs rendering removal by dialysis impossible. All ISCOMs described here are prepared by the use of Mega 10 (N-Decanoyl-N-methylglucamide). To investigate if Mega 10 is completely removed during dialysis, radiolabeled Mega 10 was synthesized in order to trace the detergent in ISCOMs.

Materials and Methods

Synthesis of Mega 10 and $^{14}$C-Mega 10.

In order to verify the synthesis path 20 mmol of decanoic acid (3.44g) were dissolved in 20 ml of ice-cold ether and 2 g of pyridine (2.04 ml). After 10 min a slight excess of ethylchloroformate (22 mmol; 2.39 g=2.1 ml) was added while vigorously stirring. The precipitate was allowed to form for 10 min and was removed by filtration. The filtrate was added to a solution of N-methyl-D-glucamine (2 mmol; 3.9 g) in warm methanol (64.5° C.) and was allowed to react for 1 hour at room temperature. Then, the solution was stored overnight at 4° C.

After the removal of ether and methanol by evaporation the remaining oil was dissolved in 80 ml of ether and 7 ml of methanol and heated to 40° C. The mixture was allowed to cool slowly upon which a white precipitate formed and the precipitation was continued overnight at 4° C. while stirring. White crystalline Mega 10 was collected by filtration and dried; total yield 5.0 g (74%).

The quality of the product was compared with Mega 10 obtained from Sigma-Aldrich by reverse-phase HPLC; no differences in HPLC-profiles were observed (data not shown).

In the case of $^{14}$C-Mega 10 the same procedure was followed, although 1 mg of $^{14}$C-decanoic acid (sodium salt) was added to the solution of unlabeled decanoic acid in ether. $^{14}$C-decanoic acid was obtained Sigma-Aldrich, St. Louis, Mo. The total yield of $^{12}$C/$^{14}$C-Mega 10 was 4.0 g (59%).

Preparation of ISCOMs.

Mega 10 (N-Decanoyl-N-methylglucamide) was purchased from Sigma-Aldrich, St. Louis, Mo. and used as a 20% stock solution. Dil (1,1'-dioctadecyl-3,3,3',3'-tetramethylindocarbocyanine perchlorate) was obtained from Molecular Probes, Eugene, OR and dissolved in DMF or EtOH before use (1.0 mg/ml). Cholesterole and phophatidylcholine (Epikuron 200S, Lucas Meyer Gmbh, Germany) was dissolved in 20% Mega 10 at a concentration of 1% w/v with respect to each component and stored at −20° C. Quil A was prepared as described by Dalsgaard [6]and stored in solution at −20° C. until used.

ISCOMs were prepared by combining Quil A, cholesterol and phophatidylcholine with the component to be inserted (e.g. lipopeptide). ISCOMs were allowed to form for 4 hours with stirring at 35° C. (room temperature for experiments with $^{12}$C/$^{14}$C-Mega 10) followed by dialysis against phosphate buffered saline (pH 7.2) in Slide-A-Lyzer® cassettes (Pierce, Rockford, Ill.) or dialysis tubing (Visking, London, UK), MW cut-off 10,000. The concentration in the reaction mixture of Quil A ranged 0.9 mg/ml to 1.3 mg/ml for the different preparations (see Section 3), whereas the concentration of cholesterol and phophatidylcholine was 0.03% w/v in all experiments. The final concentration of Mega 10 was 4% w/v unless otherwise stated.

Purification of ISCOMs.

Sucrose gradients were prepared from 25% (w/v) sucrose in phosphate buffered saline (PBS) pH 7.2. Polyallomer™ centrifuge tubes (size 13×51 mm, Beckmann Instruments) were filled with 4.5 ml sucrose solution and stored at −20° C. Upon usage the required number of tubes was allowed to thaw slowly at 4° C., typically overnight, whereby the gradient formed [7]. Gradients were allowed to equilibrate at room temperature for at least 1 hour before ISCOM-preparations were applied in a volume of 0.5 ml or less. Centrifugation was performed in a Beckmann Instruments rotor type SW55Ti at 20° C., 50,000 rpm for 3 hours. Intact ISCOMs were collected through a diode array UV-detector (Perkin Elmer) and monitored at 210 nm [8].

Amino Acid Analysis.

The Pico-Tag System® from Waters Corporation was used for determination of peptide content of ISCOMs. Hydrolysis was prefomed in a Pico-Tag workstation at 150° C. for 1 hour using 6N HCl and phenol, followed by derivatization with phenylisothiocyanate (PITC) according to the Pico-Tag protocol. In order to obtain quantitative measurement ISCOM-structure was disrupted by treatment with 1:1 dichloromethane (DCM) and acetonitril (ACN) for 10 min at room temperature after which solvent was evaporated in vacuum (se discussion in Section 3.2).

Results and Discussion

Formation of ISCOM-matrix in the Presence of Organic Solvent.

The general procedure for the formation of ISCOMs were as described by Dalsgaard et al. [9], although the concentration of Quil A was a slightly higher (1.3 mg/ml; 0.13% w/v). Cholesterol, phophatidylcholine and organic solvent (DMSO, DMF or EtOH) were combined and mixed before addition of Quil A. The initial series of experiments were performed at room temperature giving rise to precipitation of the detergent in an unpredictable manner. By equilibrating the reaction mixture at 35° C. before the addition of Quil A and during the formation of ISCOM-matrix precipitations were avoided. Also, it showed necessary to maintain an elevated temperature during the first hours of dialysis. Quil A, ISCOMs and lipids constitute a substrate for microbiological growth and it is generally advantageous to dialyze at temperatures below 5° C. In order to avoid precipitation the dialysis buffer was kept at approx. 35° C. for the initial 34 hours then allowed to cool to room temperature. Dialysis was continued for at least 6 hours before the beaker was placed at 4° C. Dialysis was carried out in Slide-A-Lyzer® (MW cut-off 10,000) cassettes from Pierce, different dialysis systems may require different timing.

Figure 9:
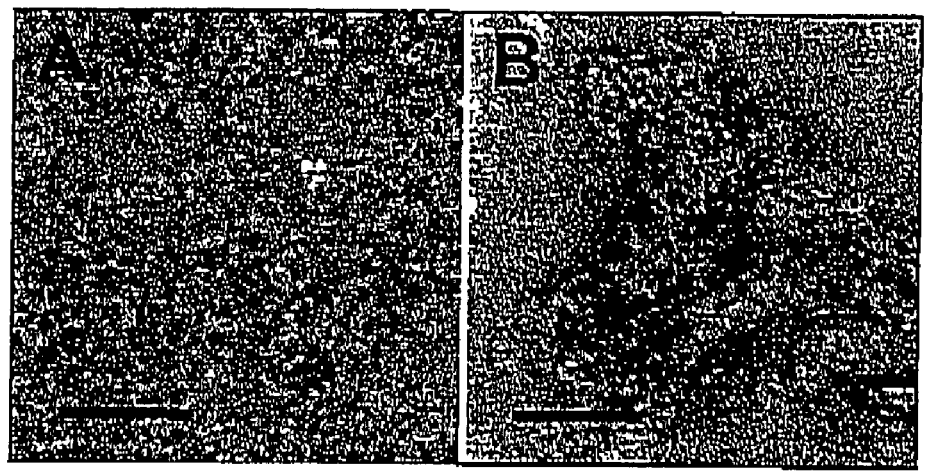

The influence of organic solvent on the formation of ISCOM-matrix was evaluated by visual inspection by electron microscopy (EM). The primary criterion was the shape and uniformity of the structures, secondary the number of ISCOM particles. The formation of ISCOM-matrix was unaffected by the presence of DMSO up to a concentration of 20% v/v (FIG. 9A); above this limit the yield was affected. With 25% DMSO intact structures could be observed but the number of ISCOMs were reduced. The same pattern was observed for DIMF. Here intact ISCOM-structures could be produced at high concentrations with a DMF concentration at or below 25%. The effect of DMF above 25% was a limited numbers of ISCOM particles although intact with respect to appearance. EtOH was compatible with the process at concentrations up to approx. 15%. Some diverging structures appeared among intact structures prepared at this concentration. Adding 20% of ethanol to the reaction mixture resulted in a very limited amount of intact ISCOM particles and clearly mis-shapen structures (FIG. 9B). It can be speculated, that the concentration of Quil A and lipids as well as the concentration of detergent (Mega 10) may bias the sensitivity of ISCOM-formation towards the concentration of organic solvent. In these experiments the final Mega 10 concentration was 4% v/w. In order to transfer these findings it should be considered to utilize equivalent concentrations of detergent. As a conclusion, the addition of solvent should be limited to:

|  | Maximum concentration (v/v) |
| --- | --- |
| DMSO | 20% |
| DMF | 25% |
| EtOH | 15% |

Embedding of Lipopeptide into ISCOMs.

In order to incorporate lipopeptides into ISCOMs the lipopeptide must be brought into solution. The solubility of lipopeptides depends both upon the actual peptide sequence and the lipid tail. The lipopeptide $NP_{147}$-S-Pam employed here consists of peptide sequence of 12 amino acids linked to palmitic acid by a thioester bond. The lyophilized lipopeptide is practically insoluble in water:detergent but readily dissolves in DMSO. However, solutions in DMSO can be further diluted with water detergent making lipopeptide availably for embedding into ISCOMs. In the case of $NP_{147}$-S-Pam a final concentration of approx. 0.5 mg/ml lipopeptide in 4.5% Mega 10, 8% v/v DMSO was used for the formation of ISCOMs. We found, that stepwise dilution with 10% Mega 10 followed by stepwise addition of water to obtain the desired concentration of lipopeptide worked consistently without precipitation of lipopeptide. Both detergent as well as water was added in three rounds with intermediate mixing. By addition of cholesterol, phosphatidylcholine and Quil A (0.13% w/v) ISCOMs formed spontaneously.

Sucrose-gradient centrifugation was used to purify intact ISCOMs. Gradients were scanned through a diode-array UV-detector to measure peptide contents and ISCOMs were collected as previously described [8]. ISCOMs are readily detected at 210 nm whereas peptides containing aromatic residues have a distinct absorption at 280 nm. The absorption of empty ISCOMs at this wavelength is very limited and the $A_{210}/A_{280}$-ration related to the peptide contents. However, one must employ different methods in order to determine the peptide contents exactly. General protein assays like the bicinchoninic acid (BCA) method is often used to determine polypeptide contents of ISCOMs. Such assays are often sensitive to the amino acid composition requiring solutions of the same peptide to be used as reference instead of protein concentration standards.

Figure 10:
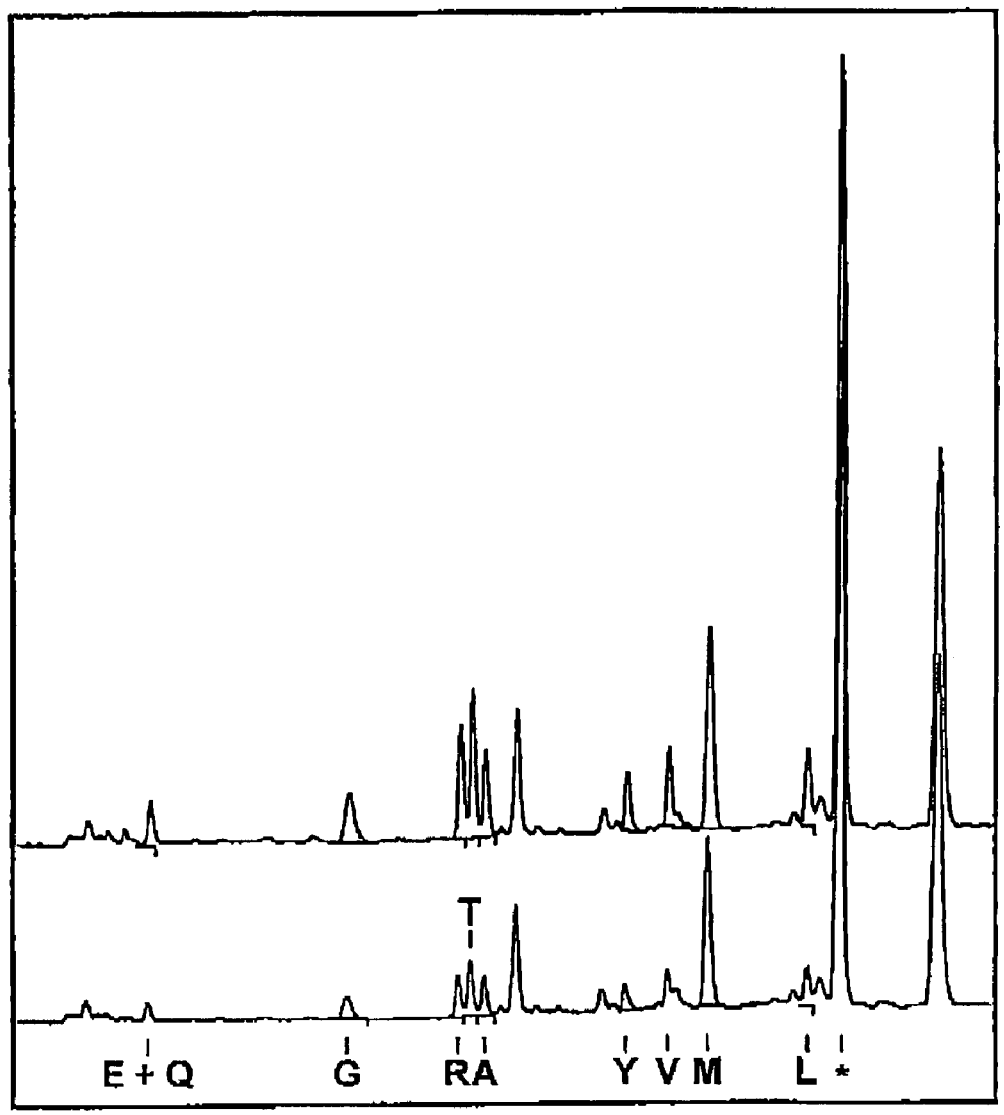
FIG. 10 illustrates that undisrupted ISCOM complexes according to the present invention protect embedded peptides from hydrolysis during the harsh conditions of the acidic hydrolysis during an amino acid analysis. This result emphasizes the high stability of the ISCOM structure and the difference in chemical environment within ISCOMs.

An alternative method is standard amino acid analysis like the Pico-Tag System® from Waters Corporation base on acidic hydrolysis, derivatization by phenyisothiocyanate (PITC) and reverse-phase HPLC-chromatography. Total peptide contents can be calculated from each amino acid and the anticipated relative amino acid composition verified. We find lyophilized ISCOMs to be compatible with the Pico-Tag protocol although ISCOM-structure must be disrupted prior to analysis by dichloromethane (DCM) and acetonitril (ACN). Undisrupted ISCOMs protects embedded peptides from hydrolysis during the harsh conditions of the acidic hydrolysis during the amino acid analysis (FIG. 10), emphasizing the high stability of the ISCOM structure and the difference in chemical environment within ISCOMs.

Lövgren et al. have previous proposed immunization with lipid-tailed peptides inserted into ISCOMs [10]. In this study an amide-linked lipopeptide originating from foot-and-mouth disease virus (VP1 144-159) was embedded into ISCOMs after dissolving lipopeptide in DMSO. ISCOMs were used for immunization, but showed inefficient in inducing antibodies (personal communication) indicating the embedding approach to be inapplicable for peptide vaccines. Consequently other methods have been investigated including the use of preformed ISCOMs as peptide carriers. Immunization with a 17-mer porcine growth hormone peptide conjugated to influenza virus ISCOMs by the bi-functional coupling agent maleimidohexanoyl-N-hydroxy-succinimide ester showed efficient [11], establishing ISCOMs as an alternative to the protein carriers like keyhole limpet haemocyanin (KLH). However, in resent experiments with thioester-linked lipopeptide including mouse CTL-epitopes derived from influenza virus (like $NP_{147}$-S-Pam) and a protective epitope from Canine Parvo Virus (CPV) lipopeptide embedded into ISCOMs were efficient in priming immunological response [12;13]. These findings may shown important for future combinations of peptides and ISCOMs and do support the theory stated by Beekman et al. that the low immunogenicity of amide-linked lipopeptides in ISCOMs is due to the high chemical stability of the amide bond rather the embedment into the structure of ISCOMs itself [14].

Preparation of Dyed ISCOMs.

The use of organic dissolvent was advantageous when incorporating sparingly water-soluble lipopeptides into ISCOMs. In order to investigate if this method was applicable for other compounds than lipopeptides, ISCOMs containing the long-chain dialkylcarbocyanine dye DiI was prepared. Labeling of pre-formed ISCOMs and ISCOM-matrix with DiI has previously been described by Claassen et al. [15] by adaptation of methods developed for labeling of liposomal membranes [16]. DiI was added to ISCOMs at a concentration of 160 µg/ml (equivalent to 200 µg/mg ISCOM) whereby up to 80% of the label was incorporated into the ISCOM-structures while unincorporated dye did precipitate due to low solubility in the aqueous buffer.

In the present study DiI was embedded into ISCOMs by adding DiI dissolved in DMF or EtOH to cholesterol and phophatidylcholine in Mega 10 followed by addition of Quil A. The concentration of DiI was 150 µg/ml giving rise to a DMF/EtOH concentration of 15% v/v in the reaction mixture.

In order to prevent precipitation of the dye the concentration of Mega 10 was adjusted to 5% w/v before the addition of DiI. After addition of DiI and Quil A (1.3 mg/ml) the concentration of detergent was 4%.

Independently of organic solvent used (DMF or EtOH) no precipitations of dye were observed during the formation reaction or after dialysis indicating quantitative incorporation of DiI. This was confirmed by density centrifugation on sucrose-gradients showing a distinct yellow band of ISCOMs with no staining outside of the ISCOM fraction (data not shown). Maximum absorption of DiI inserted into ISCOMs is observed at 552 nm [17] and the amount of dye incorporated was compared to a standard solution of DiI in methanol using a Shimadzu UV-150-02 spectrophotometer:

|  | Percent incorporation |
|---|---|
| DiI in DMF | 93/104 |
| DiI in EtOH | 97/85 |

Analysis of the Content of Detergent in ISCOMs

In the first experiment the kinetics of the Mega 10-dialysis was investigated. ISCOM-matrix was formed in the presence of 7% w/v $^{12}C/^{14}C$-Mega 10 and Quil A at a concentration of 0.9 mg/ml. From a total volume of 18.3 ml sixteen aliquots of 1 ml were taken and set up for dialysis against water in 8 beakers of 1000 ml (2×1 ml bags per 1000 ml water). Four beakers were placed at room temperature and four at 4° C. with stirring. On each of the following days one beaker from both temperatures were taken and the contents of the individual dialysis bags (2×2 bags) counted after addition of water in order to compensate for differences in volume. Table 1 lists the amount of $^{14}C$-Mega 10 remaining in each bag after dialysis for a certain period of time given as the percentage of cpm (counts per minute) relative to the initial $^{14}C$-contents. The results show that dialysis at room temperature is approximately one day ahead of dialysis at 4° C. However, the same end-point concentration of $^{14}C$-Mega 10 was reached within four days (0.4-1%) despite of temperature. Anticipating that Mega 10 diffuses freely across the dialysis membrane one would expect the contents of dialysis bags to represent 0.51% of the total $^{14}C$-Mega 10, as the volume of two bags (from one beaker) at equilibrium was 5.1 ml leaving approx. 995 ml in the beaker (5.1 ml/995 ml*100%=0.51%). And it is concluded that although dialysis at room temperature is faster than dialysis at 4° C. both methods are equally efficient in removing Mega 10 from ISCOM-matrix.

TABLE 1

Equilibrium-dialysis of $^{14}C$-Mega 10. Amount of detergent remaining in dialysis bags at different time points given as percentage of initial cpm. Dialysis buffer (water) was not replaced.

|  | Time of dialysis | | | |
|---|---|---|---|---|
|  | 1 day | 2 days | 3 days | 4 days |
| Room temperature | 2.1 | 0.9 | 0.9 | 0.4 |
|  | 2.1 | 0.9 | 0.9 | 0.7 |
| 4° C. | 14.5 | 2.2 | 1.0 | 0.7 |
|  | 13.5 | 2.3 | 1.3 | 1.1 |

In order to further investigate if Mega 10 could be completely removed from ISCOM-matrix a second experiment was designed. Here, four dialysis bags containing 1 ml of ISCOM-matrix prepared with 3.3% w/v $^{12}C/^{14}C$-Mega 10 was placed in individual beakers containing 1000 ml of water. Dialysis was performed at room temperature with stirring. Each day one beaker was taken and the contents of the dialysis bag counted after which the dialysis buffer (water) of the remaining beakers was replaced. The measured contents of $^{14}C$-Mega 10 relative to the concentration before dialysis was initiated are given in Table 2.

It is concluded, that only two days of dialysis with one replacement of the water is required in order to obtain equilibrium. This is significantly faster than in the previous experiment where equilibrium was reached within 3-4 days. Furthermore, the efficiency by which Mega 10 was removed increased by a factor of approx. 10, as only 0.07% of the original amount of detergent remains within the dialysis bag. This finding indicates that only a negligible amount of detergent remains associated with the ISCOM-structure after dialysis.

TABLE 2

End-point-dialysis of $^{14}C$-Mega 10. Amount of detergent remaining in bags after daily replacement of dialysis buffer (water).

|  | Time of dialysis | | | |
|---|---|---|---|---|
|  | 1 day | 2 days | 3 days | 4 days |
| Room temperature | 0.23 | 0.07 | 0.06 | 0.07 |

REFERENCES

[1] Kersten, G. F., Spiekstra, A., Beuvery, E. C., & Crommelin, D. J. (1991) On the structure of immune-stimulating saponin-lipid complexes (iscoms). *Biochim. Biophys. Acta,* 1062, 165-171.
[2] Villacres, M. C., Behboudi, S., Nikkila, T., Lovgren-Bengtsson, K., & Morein, B. (1998) Internalization of iscom-borne antigens and presentation under MHC class I or class II restriction. *Cell Immunol.,* 185, 30-38.
[3] Watson, D. L., Lovgren, K., Watson, N. A., Fossum, C., Morein, B., & Hoglund, S. (1989) Inflammatory response and antigen localization following immunization with influenza virus ISCOMs. *Inflammation,* 13, 641-649.
[4] Morein, B., Ekstrom, J., & Lovgren, K. (1990) Increased immunogenicity of a non-amphipathic protein (BSA) after inclusion into iscoms. *J. Immunol. Methods,* 128, 177-181.
[5] Heeg, K., Kuon, W., & Wagner, H. (1991) Vaccination of class I major histocompatibility complex (MHC)-restricted murine CD8+ cytotoxic T lymphocytes towards soluble antigens: immunostimulating-ovalbumin complexes enter the class I MHC-restricted antigen pathway and allow sensitization against the immunodominant peptide. *Eur. J. Immunol.,* 21, 1523-1527.
[6] Dalsgaard, K. (1974) Saponin adjuvants. 3. Isolation of a substance from *Quillaja saponaria* Molina with adjuvant activity in food-and-mouth disease vaccines. *Arch. Gesamte Virusforsch.,* 44, 243-254.
[7] Chanas, A. C. & Johnson, B. K. (1980) Sucrose density gradient formation by freezing and thawing. *Med. Lab Sci.,* 37, 89-90.
[8] Beekman, N., Kamstrup, S., & Dalsgaard, K. (1995) Method for monitoring ultracentrifuge gradients using a high-performance liquid chromatographic diode array detector. *Anal. Biochem.,* 228, 168-169.
[9] Stewart-Tull, D. E., Dalsgaard, K., Lovgren, K., & Lindblad, E. B. (1995) The *Theory and Practical Application of Addjuvants*. John Wiley & Sons Ltd.
[10] Lovgren, K. & Morein, B. (1988) The requirement of lipids for the formation of immunostimulating complexes (iscoms). *Biotechnol. Appl. Biochem.,* 10, 161-172.

[11] Lovgren, K. & Larsson, M. (1994) Conjugation of synthetic peptides to carrier iscoms: factors affecting the immuhogenicity of the conjugate. *J. Immunol. Methods,* 173, 237-243.

[12] Kirkby, N., Schaaper, W. M., Fomsgaard, A., & Dalsgaard, K. (2000) Vaccination by lipopeptides. Synthetic T-cell epitopes palmitoylated by thioester linkage induce CTLs in vivo by subcutaneous injection. Submitted for publication.

[13] Kirkby, N. & Dalsgaard, K. (2000) Comparison of different adjuvant systems for immunization with Canine Parvovirus. Submitted for publication.

[14] Beekman, N. J., Schaaper, W. M., Turkstra, J. A., & Meloen, R. H. (1999) Highly immunogenic and fully synthetic peptide-carrier constructs targetting GnRH. *Vaccine,* 17, 2043-2050.

[15] Claassen, I., Osterhaus, A., Boersma, W., Schellekens, M. & Claassen, E. (1995) Fluorescent labelling of virus, bacteria and iscoms: in vivo systemic and mucosal localisation patterns. *Adv. Exp. Med. Biol.,* 371B, 1485-1489.

[16] Claassen, E. (1992) Post-formation fluorescent labelling of liposomal membranes. In vivo detection, localisation and kinetics. *J. Immunol. Methods,* 147, 231-240.

[17] Claassen, I. J., Osterhaus, A. D., & Claassen, E. (1995) Antigen detection in vivo after immunization with different presentation forms of rabies virus antigen: involvement of marginal metallophilic macrophages in the uptake of immune-stimulating complexes. *Eur. J. Immunol.* 25,1446-1452.

Example 2

Preparation of DNA-binding Complexes According to the Invention

This example demonstrates how to prepare micro-particles with the capability of forming an association with DNA by means of an electrostatic interaction The complexes were prepared by substituting a fraction of cholesterol for DC-cholesterol during the formation of the complexes.

Stock solution of sterol and phospholipid. Three lipid stock solutions was prepared by dissolving Cholesterol, 3β-[N-(N', N'-Dimethylaminoethane)-Carbamoyl] Cholesterol (DC-Cholesterol, Avanti Polar Lipids) and phophatidylcholine (Epikuron 200S, Lucas Meyer Gmbh, Germany) in 20% w/v Mega 10 (N-Decanoyl-N-methyl-glucamide, Sigma-Aldrich). The concentration of the three stocks were (w/v):

|         | DC-Cholesterol | Cholesterol | Phosphaditylcholine |
|---------|----------------|-------------|---------------------|
| Stock A | 0.5%           | 0.5%        | 1.0%                |
| Stock B | 0.25%          | 0.75%       | 1.0%                |
| Stock C | 0.13%          | 0.87%       | 1.0%                |

Lipids were dissolved by agitation and heating to 40° C. Stock solutions were stored at −20° C. until used.

Complex formation. A reaction mixture containing Quil A (Quillaja saponin) at a concentration of 1.7 mg/ml and 0.034% w/v phophatidylcholine in 5% w/v Mega 10 was prepared by diluting lipid stock A, B or C with 10% w/v Mega 10 and water. The final concentration of DC-cholesterol and cholesterol varied due to the composition of the selected lipid stock solution:

| Final conc. | DC-Cholesterol | Cholesterol | Phosphadltylcholine |
|-------------|----------------|-------------|---------------------|
| Stock A     | 0.017%         | 0.017%      | 1.0%                |
| Stock B     | 0.0085%        | 0.026%      | 1.0%                |
| Stock C     | 0.0043%        | 0.030%      | 1.0%                |

Complex formation was initiated by the addition of Quil A and the reaction mixtures were incubated with magnetic stirring for 2 hours at 30° C. by which the microparticles form.

Complex purification. Following incubation the microparticle suspensions were dialyzed against phosphate buffered saline (PBS) using dialysis tubing with a molecular weight cut-off at 10,000 (Pierce, Slide-A-Lyzer, MWCO 10,000). Dialysis is continued for 24 hours at room temperature, with one replacement of dialysis buffer after 12 hours.

Evaluation of micro-particle structure. After dialysis ISCOMs were passively absorbed on electron microscopy grids, dried and negatively stained with uranylacetate. All preparations yielded particles with characteristic cage-like structures know to ISCOMs.

Example 3

Degradation of Linear Plasmid DNA Bound to DNA-binding ISCOMs

The aim of the present example is to examine whether DNA associated with DNA-binding ISCOMs are protected from degradation by DNase I. Lineraized plasmid DNA was enzymatically labeled with $^{32}P$. Labeled DNA was allowed to bind to ISCOMs and treated with or without DNAse I. ISCOMs were colleted by filtration and the amount of label retained was used as a measurement of the amount of DNA protected from degradation.

Labeling of DNA. Plasmid pUC18 digested with BamH1 (Amersham-Pharmacia, pUC18 BamH1/BAP) was labeled using DNA polymerase I Kienow Fragment by adding 10 μCi [α-$^{32}P$]dGTP (Amersham-Pharmacia, AA0066) to 1 μg of DNA in 25 μl EcoPol Buffer (New England BioLabs, 10 mM Tris-HCl, 5 mM $MgCl_2$, 5 mM DTT, pH 7.5). By further addition of 1 unit Kienow Fragment (New England BioLabs, M0212S) the reaction was initiated. After incubation for 15 minutes at room temperature the reaction was stopped by heating for 5 minutes at 70° C. The volume was adjusted to 50 μl with water and unincorporated nucleotides was removed by spin-column purification using MicroSpin S-400 HR Columns (Amersham-Pharmacia, 27-5140-01) as described in the instructions manual.

After removal of unincorporated $^{32}P$ the plasmid was further diluted to 400 μl by Eco-Pol Buffer (New England BioLabs) and the incorporation checked by Cerenkov counting using a Packard Tri-Card 4000 scintillation counter.

Binding of labeled DNA to ISCOMs. ISCOMs containing DC-cholesterol/cholesterol at a ration of 1:1 was allowed to associate with labeled DNA. In two separate tubes (A. B) 100 μl of labeled linear plasmid (corresponding to approx. 150 ng) was mixed with 10 μg of ISCOMs (30 μl of ISCOMs phosphate buffered saline, pH 7.2) and incubated for 1 h at room temperature. As a control experiment ordinary ISCOMs containing no DC-cholesterol (10 μg in phosphate buffered saline) was mixed with an equal amount of labeled DNA and the volume adjusted to 130 μl. This sample (C) was incubated in parallel to the samples containing DC-cholesterol ISCOMs.

Degradation of DNA. After incubation of labeled DNA with ISCOMs, 10 units DNase I (Stratagene, 600031) was added to tubes A (DNA-binding ISCOMs) and C (control ISCOMs). Before addition enzyme was diluted 10-fold to 10 units/μl in DNase reaction buffer (40 mM Tris-HCl, 6 mM $MgCl_2$, 2 mM $CaCl_2$, pH 7.5). DNase was allowed to digdiest DNA for 1 hour at 37° C., after which the reaction was stopped by addition of 5 μl 500 mM EDTA pH 8.0.

Separation of degraded DNA and ISCOM-bound DNA. Both the DNase treated samples (A, C) and the non-digested sample (B) was transferred to micro-centrifuge filters (Millipore, Ultrafree-MC, 30,000 NMWL Filter Units) and forced through the filter membrane by centrifugation for 10 minutes at 4.000 xg. The effluent was discarded while the filter-cups were transferred to scintillation-vials. The amount of label retained in the filters was measured by adding 2 ml of scintillation fluid (Packard, Opti-Flour O) to each filter followed by counting on $^{32}$P-programme in Packard Tri-Carb 4000 scintilation counter.

Results. It is anticipated that a linear correlation between the measured amount of counts per minute (cpm) and the amount of intact DNA entrapped by the filters exists. The specific activity measured for the control reaction (C) was 1525±305 cpm which, when compared to the 18,235±456 cpm of the non-digested DNA in combination with DC-cholesterol (B) verifies the capacity of these ISCOMs to bind DNA.

Futhermore, when DNase was used to degrade DNA prior to filtration the activity measured on the filter (A) was reduced to 7,315±183 cpm. This is lower than the un-digested sample (B) indicating that some of the label was released from the ISCOMs due to degradation of DNA by DNase I.

However, as the measurement of the digested sample (A) is at least a factor of 4 higher than the control (C) a substantial amount of the DNA is retained on the filters despite the DNase treatment. It is concluded that the ISCOMs contaning DC-cholesterol not only binds DNA but also protects DNA, when bound, from degradation by DNase I.

Example 4

Determination of Zeta-potentials of DNA-binding ISCOMs

The parameter of zeta potential is a measure of the magnitude of the repulsion or attraction between particles. Its measurement relates to some extent to the overall charge of particles but also to the stability of particles in dispersion. The surface charge of particles in polar liquids dose not directly correlate to the electrical potential at the surface of the particle but to the potential that in the close vicinity of the particle.

The Zeta-potential of three different compositions of ISCOMs were analyzed using Zetasizer 1000 HS from Malvem Instruments Ltd, UK.

Preparation of ISCOMs. Following the procedure in Example no. 2, ISCOMs were prepared as 25% or 50% of the cholesterol were substituted by DC-cholesterol during the formation of the particles. Also ISCOMs in which no DC-cholesterol were prepared by the analogous protocol. ISCOMs were purified by dialysis against phosphate buffered saline (0.85% NaCl, 0.01M phosphate buffer, pH 7.2) and stored at −20° C. until used.

Measurement of Zeta-potential Prior to measurement ISCOMs were diluted to a final concentration of 5-20 μg/ml with phosphate buffered saline (as above). For each measurement approx. 5 ml of diluted ISCOMs were injected into the measuring chamber.

Zeta-potentials were measured using standard procedures as described in the instruments manual. For each injected sample the Zeta potential were measured five consecutive times (5×1 minute).

Figure 8:
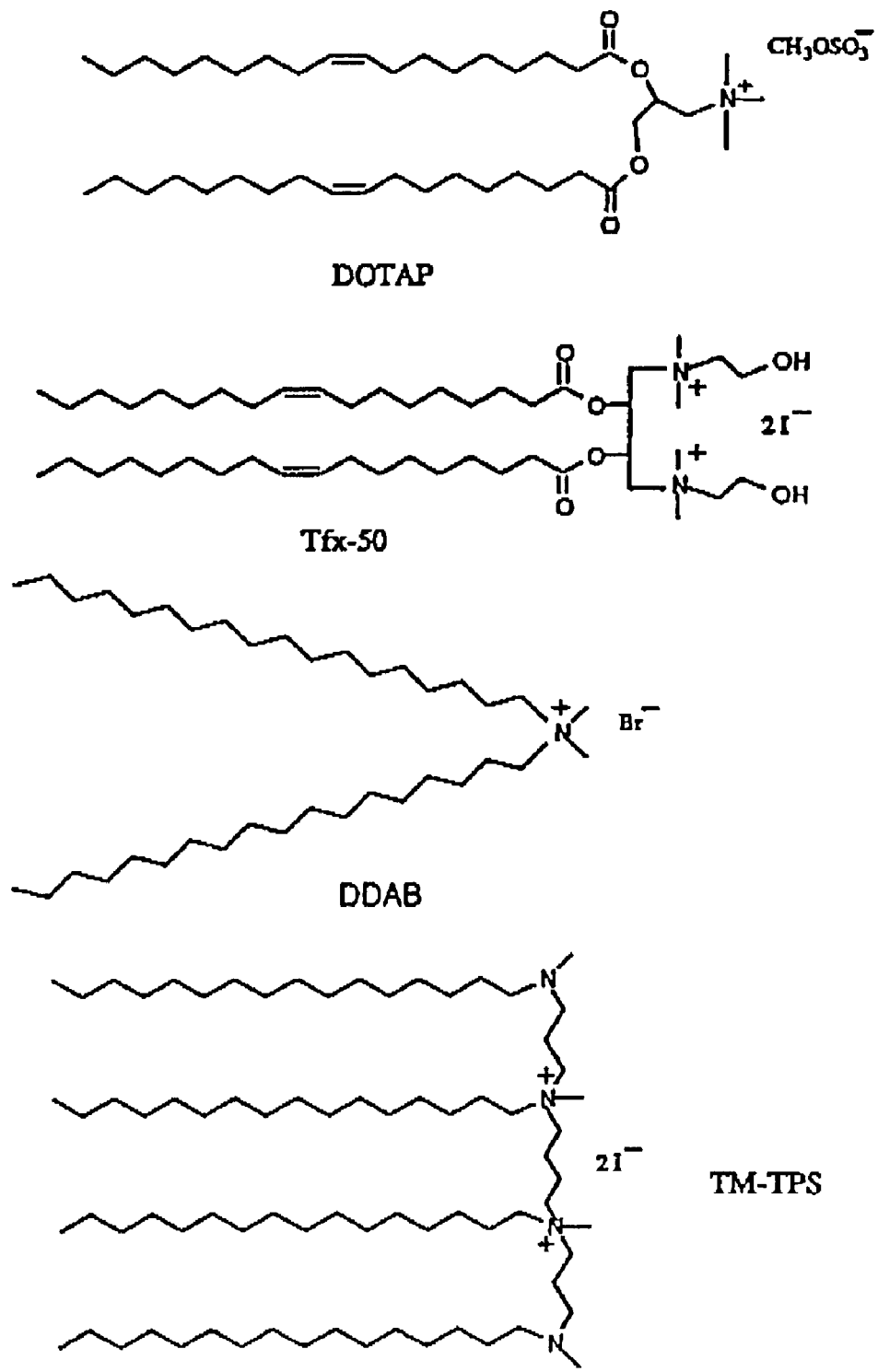
FIG. 8 Illustrates even further preferred lipophilic moieties capable of being incorporated into the complexes according to the present invention. The listed compounds are DOTAP, or (N[1-(2,3-dioleoyloxy)propyl]-N,N,N-trimethylammonium-ethylsulfate; Tfx-50, or N,N,N',N'-tetramethyl-N,N'-bis(2-hydoxyethyl)-2,3-dioleoyloxy-1,4-butanediammoniumiodide; DDAB, or dimethyl-dioctadecylammonuimbromide; and TM-TPS, or tetrapaimitylspermine, FIG. 9 illustrates the influence of organic solvent on the formation of ISCOM-matrix as evaluated by visual inspection by electron microscopy (EM). The primary criterion was the shape and uniformity of the structures, secondary the number of ISCOM particles. The formation of ISCOM-matrix was unaffected by the presence of DMSO up to a concentration of 20% v/v as shown in panel A. Above this limit the yield was affected. With 25% DMSO intact structures could be observed but the number of ISCOMs were reduced. The same pattern was observed for DMF, as described in detail in Example 1 herein. Panel B in FIG. 9 demonstrates that EtOH was compatible with the process at concentrations up to approx. 15%. Some diverging structures appeared among intact structures prepared at this concentration.
Figure 11:
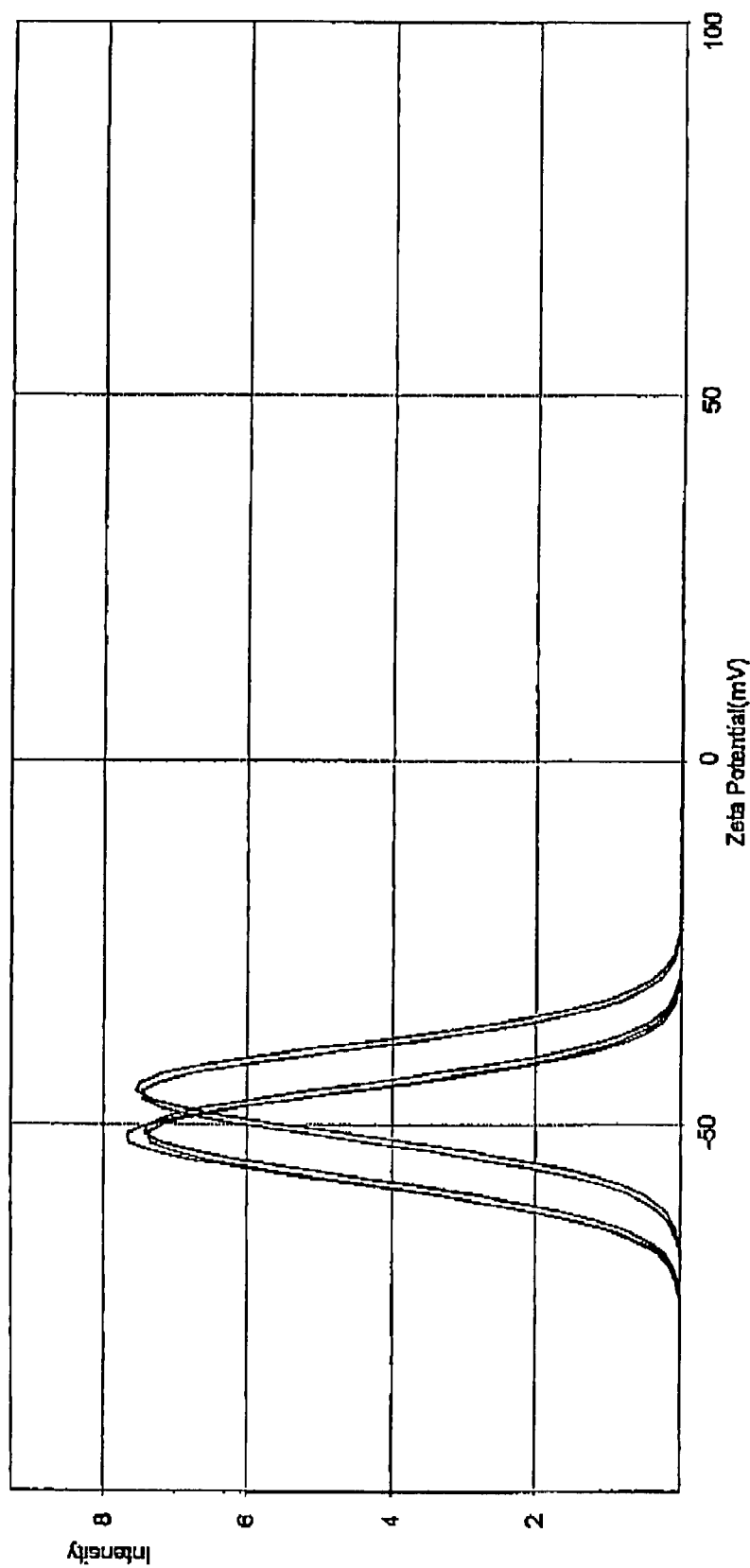
FIG. 11 illustrates measurement of zeta potentials for ISCOMs containing no DC-cholesterol performed as described in example 4. Similar to the experiments described in FIG. 12, the Zeta-potential was measured five times. The average Zeta-potential was found to be approx. −50 mV (see table below), which is significantly different from the ISCOMs containing DC-cholesterol (DC-cholesterol to cholesterol ratio 1:1 or 1:2), as demonstrated in FIG. 12.

FIG. 11 illustrates the measurement of ISCOMs containing no DC-cholesterol. Each curve represents one of five measurements. The average Zeta-potential was found to be approx. −50 mV, which is significantly different from the data obtained from measurements of ISCOMs containing DC-cholesterol (DC-cholesterol to cholesterol ratio 1:1 or 1:2) as illustrated in FIG. 8.

FIG. 12 illustrates the measurement of modified ISCOMs. DC-cholesterol to cholesterol ration was 1:1 (50% substitution). Similar to the experiments described above and in FIG. 7, the Zeta-potential was measured five times. The Zeta-potential was close to 0 mV with some variation between measurements. When ISCOMs with a DC-cholesterol to cholesterol of 1:2 (25%) were measured, an average Zeta-potential of approx. −25 mV was observed (data not shown).

Example 5

Transfection with Plasmid DNA in Combination with DNA-binding ISCOMs

To investigate if the hemolytic property of ISCOMs could increase the uptake of DNA in cultured cells a reporter plasmid expressing green flourescent protein (GFP) was transfected after binding to DC-cholesterol containing ISCOMs.

Preparation of DNA-ISCOM complexes. Plasmid DNA (2 μg) was combined with 2 μg of ISCOMs containing DC-cholesterol and cholesterol at a ratio of 1:1, as prepared in Example 2. This was done in a volume of 40 μl (10 mM Tris-HCl, pH 7.5) and complexes were allowed to form for 1 h at room temperature. The volume was adjusted to 100 μl.

Preparation of DNA-Lipofectin complexes. To compare the efficiency of ISCOMs versus a well-know and efficient transfection reagent (Lipofectamin Reagent, Gibgo BRL, 18292-011) was included in the experiment. Again, 2 μg of plasmid DNA was combined diluted to 50 μl with water and combined with a solution of 50 μl (15 μl Lipofectin Reagent diluted with 35 μl water).

Transfection of cells. RDM4 cells were cultured in RPMI 1640 medium supplemented with 10% fetal calf serum (FSC). Cells ($10^5$) were grown in small tissues culture dishes (ø40 mm) for 24-36 h prior to transfection. Before tansfection cells were washed three times with serum-free medium. The DNA suspensions were added to 2 ml of serum-free medium just prior to transfection and added to the cells. Cells were incubated for 4 hours and then washed with medium containing serum. After removal of the tansfection mixture cells were allowed to grow for 24 h before the GFP-activity were tested.

Result of transfection. Fluorescent cells were counted in a stero-microscope equipped with a ultraviolet light source and the fraction of transfected cells estimated. Transfection with Lipofectin were highly efficient, as more than 80% of the cells were clearly fluorescent. ISCOMs, where also capable to transfect cells, but with lower efficiency. Here, approx. 25% of the cells had the flourecent phenotype although the intensity of the fluorescent light was quiet varying from cell to cell.

The invention claimed is:

1. A complex comprising
   (i) a sterol selected from the group consisting of cholesterols, lanosterols, lumisterols, stigmasterols, sitosterols, mycosterols, ergosterols, and thiocholesterols,
   (ii) a sterol selected from the group consisting of 3β-[N-(Dimethylaminoethane)-carbamoyl]cholesterol (DC-cholesterol), N-(trimethylammonioethane)-carbamoyl-cholesterol (TC-cholesterol), and a combination thereof,
   wherein said sterols form a complex with a saponin; and
   (iii) a saponin comprising a triterpene glycoside isolated from a Quillaja plant species, wherein the saponin forms a complex with said sterols; and
   wherein the complex adopts a micro-particle structure in the form of a cage-like matrix.

2. The complex of claim 1, wherein the sterol of (i) comprises cholesterol.

3. The complex according to claim 1, wherein the saponin is isolated from a *Quillaja saponaria* species.

4. The complex according to claim 3, wherein the saponin is isolated from *Quillaja saponaria* Molina or *Quillaja saponaria* Officinalis.

5. The complex according to claim 4, wherein the saponin is Quil A.

6. The complex according to claim 1, further comprising an additional lipophilic moiety.

7. The complex according to claim 6, wherein the additional lipophilic moiety comprises a phospholipid.

8. The complex according to claim 7, wherein the phospholipid is selected from the group consisting of a phosphatidylcholine and a phosphatidylethanolamine.

9. The complex according to claim 8, wherein the phospholipid comprises phosphatidylethanolamine.

10. The complex according to claim 8, wherein the phospholipid comprises phosphatidylcholine.

11. A method of preparing the complex of claim 7 comprising mixing a) a sterol selected from the group of sterols consisting of cholesterols, lanosterols, lumisterols, stigmasterols, sitosterols, mycosterols, ergosterols, and thiocholesterols with b) a sterol selected from the group consisting of 3β-[N-(Dimethylaminoethane)-carbamoyl]cholesterol (DC-cholesterol), N-(trimethylammonioethane)-carbamoylcholesterol (TC-cholesterol), and a combination thereof, c) a saponin comprising a triterpene glycoside isolated from a Quillaja plant species, d) a phospholipid, and e) an organic solvent, wherein the components a) to e) may be mixed simultaneously, or sequentially, in any order.

12. The method of claim 11, wherein the phospholipid is selected from the group consisting of a phosphatidyicholine and a phosphatidylethanolamine.

13. The method of claim 11, wherein the organic solvent is selected from the group consisting of ethanol, DMSO, DMF, and a combination thereof 14. The method of claim 11, wherein the solvent is present in an amount of at the most 25% (vol/vol).

15. The method of claim 11, further comprising (f) removing surplus reactants and purifying the prepared complexes.

16. The complex of any one of claims 1, 2, 5, 8, or 10, further comprising a bioactive agent.

17. The complex of any one of claims 1, 2, 5, 8, or 10, further comprising a polynucleotide.

18. The complex according to claim 17, wherein the polynucleotide encodes a therapeutic protein.

19. The complex any one of claims 1, 2, 5, 8, or 10, further comprising a polypeptide.

20. The complex of claim 19, wherein the polypeptide is a therapeutic polypeptide.

21. The complex of any one of claims 1, 2, 5, 8, or 10, further comprising an immunogenic determinant.

22. The complex of claim 21, wherein the immunogenic determinant is selected from the group consisting of a bacterial immunogenic determinant and a viral immunogenic determinant.

23. The complex of claim 21, wherein the immunogenic determinant is selected from the group consisting of polynucleotides, polypeptides, lipids, saccharides, and any combination thereof.

24. A pharmaceutical composition comprising the complex of claim 21, in combination with a pharmaceutically acceptable carrier.

25. The complex of any one of claims 1, 2, 5, 8, or 10, wherein the complex has a spherical shape and a diameter in the range of from 25 nm to 75 nm.

26. The complex of claim 16, wherein the complex has a spherical shape and a diameter in the range of from 25 nm to 75 nm.

27. A method of preparing the complex of claim 16 comprising mixing a) a sterol selected from the group of sterols consisting of cholesterols, lanosterols, lumisterols, stigmasterols, sitosterols, mycosterols, ergosterols, and thiocholesterols with b) a sterol selected from the group consisting of 3β-[N-(Dimethylaminoethane)-carbamoyl]cholesterol (DC-cholesterol), N-(trimethylammonioethane)-carbamoylcholesterol (TC-cholesterol), and a combination thereof, c) a saponin comprising a triterpene glycoside isolated from a Quillaja plant species, d) a phospholipid, e) a bioactive agent and f) an organic solvent, wherein the components a) to f) may be mixed simultaneously, or sequentially, in any order.

28. The method of claim 27, wherein the phospholipid is selected from the group consisting of a phosphatidyicholine and a phosphatidylethanolamine.

29. The method of claim 27, wherein the organic solvent is selected from the group consisting of ethanol, DMSO, DMF, and a combination thereof.

30. The method of claim 27, wherein the solvent is present in an amount of at the most 25% (vol/vol).

31. The method of claim 27, further comprising (g) removing surplus reactants and purifying the prepared complexes.

32. A pharmaceutical composition comprising the complex of claim 16, in combination with a pharmaceutically acceptable carrier.

* * * * *